US006485413B1

United States Patent
Boppart et al.

(10) Patent No.: US 6,485,413 B1
(45) Date of Patent: *Nov. 26, 2002

(54) METHODS AND APPARATUS FOR FORWARD-DIRECTED OPTICAL SCANNING INSTRUMENTS

(75) Inventors: Stephen A. Boppart, Boston; Gary J. Tearney, Cambridge; Brett E. Bouma, Boston; Mark E. Brezinski, Malden; James G. Fujimoto, Cambridge; Eric A. Swanson, Acton, all of MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,283

(22) Filed: Mar. 6, 1998

Related U.S. Application Data

(63) Continuation-in-part of application No. 08/916,759, filed on Aug. 19, 1997, now Pat. No. 5,784,352, which is a continuation-in-part of application No. 08/607,787, filed on Feb. 27, 1996, now Pat. No. 6,134,003, which is a continuation-in-part of application No. 08/577,366, filed on Dec. 22, 1995, now Pat. No. 5,748,598, which is a continuation of application No. 08/492,738, filed on Jun. 21, 1995, now abandoned, which is a continuation-in-part of application No. 08/252,940, filed on Jun. 2, 1994, now abandoned, which is a continuation-in-part of application No. 08/033,194, filed on Mar. 16, 1993, now Pat. No. 5,459,570, which is a continuation of application No. 07/692,877, filed on Apr. 29, 1991, now abandoned.

(60) Provisional application No. 60/054,163, filed on Jul. 29, 1997, and provisional application No. 60/038,047, filed on Mar. 6, 1997.

(51) Int. Cl.[7] ............................. A61B 1/06; A61B 6/00
(52) U.S. Cl. .................. 600/160; 600/129; 600/477; 600/478; 356/345; 356/349
(58) Field of Search .................. 600/160, 101, 600/109, 129, 310, 342, 473, 476, 478, 173, 477; 356/345, 349

(56) References Cited

U.S. PATENT DOCUMENTS 3,532,037 A * 10/1970 Auphan ..................... 600/173

(List continued on next page.)

FOREIGN PATENT DOCUMENTS

DE 3527245 2/1987

(List continued on next page.)

OTHER PUBLICATIONS

Bail, M. et al., "Optical coherence tomography by "spectral radar" for the analysis of human skin", *SPIE*, vol. 3196, 1997.

(List continued on next page.)

*Primary Examiner*—John P. Leubecker
(74) *Attorney, Agent, or Firm*—Testa, Hurwitz & Thibeault, LLP

(57) ABSTRACT

An imaging system for performing forward scanning imaging for application to therapeutic and diagnostic devises used in medical procedures. The imaging system includes forward directed optical coherence tomography (OCT), and non-retroreflected forward scanning OCT. Also interferometric imaging and ranging techniques and fluorescent, Raman, two-photon, and diffuse wave imaging can be used. The forward scanning mechanisms include a cam attached to a motor, pneumatic devices, a pivoting device, piezoelectric transducers, electrostatic driven slides for substantially transverse scanning; counter-rotating prisms, and offset lenses are used for arbitrary scanning. The imaging system of the invention is applied to hand held probes including probes integrated with surgical probes, scalpels, scissors, forceps and biopsy instruments. Hand held probes include forward scanning lasers. The imaging system is also applicable to laparoscopes and endoscopes for diagnostc and therapeutic intervention in body orifices, canals, tubes, ducts, vessels and cavities of the body. The imaging system includes application to surgical and high numerical aperture microscopes. An important application of the invention is implantation of the optical probe for periodic or continuous extraction of information from the tissue site where implanted.

9 Claims, 33 Drawing Sheets

NON-RETROREFLECTION OCT EMBODIMENT

U.S. PATENT DOCUMENTS

| | | | |
|---|---|---|---|
| 3,549,239 A | 12/1970 | Brienza et al. | 350/162 |
| 3,556,079 A | 1/1971 | Izumi-Otsu | 128/2 |
| 3,710,798 A | 1/1973 | Bredemeier | 128/303.1 |
| 3,769,963 A | 11/1973 | Goldman et al. | 128/2 R |
| 3,821,510 A | 6/1974 | Muncheryan | 219/121 L |
| 3,905,703 A | 9/1975 | Matsumoto | 356/106 R |
| 3,906,953 A | 9/1975 | Wallace et al. | 128/303.1 |
| 3,961,621 A | 6/1976 | Northeved | 128/2 |
| 3,961,841 A | 6/1976 | Giordmaine | 350/160 |
| 4,058,114 A | 11/1977 | Soldner | 128/2 |
| 4,091,814 A | 5/1978 | Takashi | 128/303.1 |
| 4,141,362 A | 2/1979 | Helmut | 128/303.1 |
| 4,171,159 A | 10/1979 | White | 356/349 |
| 4,336,809 A | 6/1982 | Clark | 128/665 |
| 4,420,260 A | 12/1983 | Martinelli | 356/351 |
| 4,545,390 A | 10/1985 | Leary | 128/772 |
| 4,554,929 A | 11/1985 | Samson et al. | 128/772 |
| 4,596,466 A | 6/1986 | Ulrich | 356/345 |
| 4,612,938 A | 9/1986 | Dietrich et al. | 128/665 |
| 4,619,274 A | 10/1986 | Morrison | 128/772 |
| 4,638,800 A | 1/1987 | Michel | 128/303.1 |
| 4,648,892 A | 3/1987 | Kittrell | 65/4.21 |
| 4,652,129 A | 3/1987 | Martinelli | 356/345 |
| 4,669,465 A | 6/1987 | Moore et al. | 128/303.1 |
| 4,669,467 A | 6/1987 | Willett et al. | 128/303.1 |
| 4,718,417 A | 1/1988 | Kittrell et al. | 128/303.1 |
| 4,721,117 A | 1/1988 | Mar et al. | 128/772 |
| 4,748,986 A | 6/1988 | Morrison et al. | 128/772 |
| 4,796,994 A | 1/1989 | Bager | 356/358 |
| 4,819,632 A | 4/1989 | Davies | 128/303.1 |
| 4,834,102 A | 5/1989 | Schwarzchild et al. | 128/662.06 |
| 4,844,062 A | 7/1989 | Wells | 128/303.1 |
| 4,873,989 A | 10/1989 | Einzig | 128/692 |
| 4,887,606 A | 12/1989 | Yock et al. | 128/662.05 |
| 4,899,733 A | 2/1990 | DeCastro et al. | 128/7 |
| 4,900,314 A | 2/1990 | Quackenbush | 604/282 |
| 4,913,142 A | 4/1990 | Kittrell et al. | 606/7 |
| 4,928,005 A | 5/1990 | Lefévre et al. | 250/227.23 |
| 4,958,930 A | 9/1990 | Robertson, Jr. | 356/357 |
| 4,969,736 A | 11/1990 | Slotwinski | 356/4.5 |
| 5,005,584 A | 4/1991 | Little | 128/748 |
| 5,032,722 A | 7/1991 | Boesle et al. | 250/287 |
| 5,034,613 A | 7/1991 | Denk et al. | 250/458.1 |
| 5,053,033 A | 10/1991 | Clarke | 606/3 |
| 5,094,534 A | 3/1992 | Cole et al. | 356/345 |
| 5,104,392 A | 4/1992 | Kittrell et al. | 606/15 |
| 5,106,387 A | 4/1992 | Kittrell et al. | 606/15 |
| 5,110,211 A | 5/1992 | Niki et al. | 326/346 |
| 5,114,403 A | 5/1992 | Clarke et al. | 604/96 |
| 5,133,598 A | 7/1992 | Badeau | 356/345 |
| 5,155,549 A | 10/1992 | Dhadwal | 356/336 |
| 5,157,457 A | 10/1992 | Taylor | 356/345 |
| 5,196,004 A | 3/1993 | Sinofsky | 606/3 |
| 5,197,470 A | 3/1993 | Helfer et al. | 128/634 |
| 5,201,317 A | 4/1993 | Kanazawa et al. | 128/665 |
| 5,202,745 A | 4/1993 | Sorin et al. | 356/73.1 |
| 5,217,456 A | 6/1993 | Narciso, Jr. | 606/15 |
| 5,251,198 A | 10/1993 | Strickler | 369/110 |
| 5,257,991 A | 11/1993 | Fletcher et al. | 606/17 |
| 5,268,738 A | 12/1993 | Baney et al. | 356/345 |
| 5,268,741 A | 12/1993 | Chou et al. | 356/351 |
| 5,291,267 A | 3/1994 | Sorin et al. | 356/345 |
| 5,303,026 A | 4/1994 | Strobl et al. | 356/318 |
| 5,305,759 A | 4/1994 | Kaneko et al. | 128/665 |
| 5,318,024 A * | 6/1994 | Kittrell et al.. | 600/478 |
| 5,321,501 A | 6/1994 | Swanson et al. | 356/345 |
| 5,325,177 A | 6/1994 | Peterson | 356/357 |
| 5,343,543 A | 8/1994 | Novak et al. | 385/31 |
| 5,354,294 A | 10/1994 | Chou | 606/16 |
| 5,365,335 A | 11/1994 | Sorin | 356/345 |
| 5,366,456 A | 11/1994 | Rink et al. | 606/16 |
| 5,370,649 A | 12/1994 | Gardetto et al. | 606/17 |
| 5,383,467 A | 1/1995 | Auer et al. | 128/664 |
| 5,390,023 A | 2/1995 | Biegen | 356/359 |
| 5,401,270 A | 3/1995 | Müller et al. | 606/13 |
| 5,421,337 A | 6/1995 | Richards-Kortum | 128/665 |
| 5,421,339 A | 6/1995 | Ramanujam et al. | 128/665 |
| 5,428,699 A | 6/1995 | Pon | 385/31 |
| 5,434,669 A * | 7/1995 | Tabata et al. | 600/160 |
| 5,439,000 A | 8/1995 | Gunderson et al. | 128/664 |
| 5,459,570 A | 10/1995 | Swanson et al. | 356/345 |
| 5,465,147 A | 11/1995 | Swanson | 356/345 |
| 5,490,521 A | 2/1996 | Davis et al. | 128/662.02 |
| 5,495,541 A | 2/1996 | Murray et al. | 385/33 |
| 5,501,226 A | 3/1996 | Petersen et al. | 128/691 |
| 5,501,599 A * | 3/1996 | Rechmann | 433/215 |
| 5,509,917 A | 4/1996 | Cecchetti et al. | 606/15 |
| 5,537,499 A | 7/1996 | Brekke | 385/31 |
| 5,555,087 A | 9/1996 | Miyagawa et al. | 356/345 |
| 5,562,100 A | 10/1996 | Kittrell et al. | 128/665 |
| 5,562,657 A | 10/1996 | Griffin | 606/17 |
| 5,570,182 A * | 10/1996 | Nathel et al. | 356/345 |
| 5,571,099 A | 11/1996 | Purcell et al. | 606/17 |
| 5,589,938 A | 12/1996 | Deck | 356/359 |
| 5,601,087 A | 2/1997 | Gunderson et al. | 128/664 |
| 5,612,540 A | 3/1997 | Richards-Kortum et al. | 250/461.2 |
| 5,623,932 A | 4/1997 | Ramanujam et al. | 128/665 |
| 5,697,373 A | 12/1997 | Rcihards-Kortum et al. | 128/664 |
| 5,699,795 A | 12/1997 | Richards-Kortum et al. | 128/634 |
| 5,715,825 A | 2/1998 | Crowley | 128/602.06 |
| 5,748,598 A | 5/1998 | Swanson et al. | 369/94 |
| 5,752,518 A | 5/1998 | McGee et al. | 128/662.06 |
| 5,762,613 A | 6/1998 | Sutton et al. | 600/564 |
| 5,772,657 A | 6/1998 | Hmelar et al. | 606/15 |
| 5,784,352 A | 7/1998 | Swanson et al. | 369/94 |
| 5,787,890 A * | 8/1998 | Reiter et al. | 600/558 |
| 5,815,611 A | 9/1998 | Dhadwal | 385/12 |
| 5,921,926 A * | 7/1999 | Rolland et al. | 600/407 |
| 6,111,645 A | 8/2000 | Tearney et al. | 356/354 |
| 6,134,003 A | 10/2000 | Tearney et al. | 356/345 |
| 6,160,826 A | 12/2000 | Swanson et al. | 372/20 |

FOREIGN PATENT DOCUMENTS

| | | |
|---|---|---|
| DE | 3627420 A1 | 2/1987 |
| DE | 4309056 | 9/1994 |
| EP | 60235005 A | 11/1985 |
| EP | 04135552 A | 9/1990 |
| EP | 0501034 A1 | 9/1992 |
| EP | 0825464 A1 | 2/1998 |
| FR | 2734914 | 12/1996 |
| GB | 2191855 | 12/1987 |
| JP | 6-35946 | 6/1994 |
| WO | 92/14399 | 9/1992 |
| WO | 92/19930 | 11/1992 |
| WO | 95/28129 | 10/1995 |
| WO | WO9533970 A | 12/1995 |
| WO | 97/32182 | 9/1997 |
| WO | 97/41767 | 11/1997 |
| WO | 98/27865 | 7/1998 |
| WO | 98/38907 | 11/1998 |
| WO | 00/42906 | 7/2000 |

OTHER PUBLICATIONS

Beaud, P. et al. "Optical reflectometry with micrometer resolution for the investigation of integrated optical devices", *IEEE Journal of Quantum Electronics*, vol. 25, No. 4, pp. 755–759 (Apr. 4, 1989).

Boppart, et al., "High–resolution optical coherence tomography–guided laser ablation of surgical tissue." *Journal of Surgical Research*, vol. 82, No. 2, pp. 275–284 (Apr. 1999).

Boppart, et al., "Imaging developing neural morphology using optical coherence tomography" *Journal of Neuroscience Methods*, vol. 70, No. 1, pp. 65–72 (Dec. 1996).

Boppart, et al., "In vivo cellular optical coherence tomography imaging," *Nature Medicine*, vol. 4, No. 7, pp. 861–865 (Jul. 1988).

Boppart, et al, "Intraoperative assessment of microsurgery with three–dimensional optical coherence tomography", *Radiology*, vol. 208, No. 1, pp. 81–86 (Jul. 1998).

Boppart, et al., "Optical coherence tomography for neurosurgical imaging of human intracortical melanoma." *Neurosurgery*, vol. 43, No. 4, pp. 834–841 (Oct. 1998).

Bouma, B. et al., "High–resolution optical coherence tomographic imaging using a mode–locked Ti:Al$_2$O$_3$ laser source", *Optics Letters*, vol. 22, No. 13, pp. 1486–1488 (Jul. 1, 1995).

Brezenski, Mark E., et al., "Optical Coherence Tomography for Optical Biopsy Properties and Demonstration of Vascular Pathology", *Circulation*, vol. 93, No. 6, pp. 1206–1213 (Mar. 15, 1996).

Brezinski, et al., "Assessing atherosclerotic plaque morphology: comparison of optical coherence tomography and high frequency intravascular ultrasound." *Heart*, vol. 77, No. 5, pp. 397–403 (May 1997).

Brezinski, et al., "Optical Biopsy with optical coherence tomography: feasibility for surgical diagnostics." *Journal of Surgical Research*, vol. 71, No. 1, pp. 32–40 (Jul. 15, 1997).

Brezinski, et al., "Optical biopsy with optical coherence tomography" *Advances in Optical Biopsy and Optical Mammography*, vol. 838, pp. 68–74 (1998).

Brezinski, M. E., et al. "Imaging of coronary artery microstructure (in vitro) with optical coherence tomography", *The American Journal of Cardiology*, vol. 77 (Jan. 1, 1996).

Chinn, S. R. and E. A. Swanson, "Blindness limitations in optical coherence domain reflectometry", *Electronics Letters*, vol. 29, No. 23, pp. 2025–2027 (Nov. 11, 1993).

Chornenky, V. "Low–coherence interferometry in coronary arteries", *Coronary Artery Disease*, vol. 6, No. 5, pp. 377–380 (May 1995).

Clivaz, X. et al. "High Resolution reflectometry in biological tissues", *Optics Letters*, vol. 17, No. 1, pp. 4–6 (Jan. 1, 1992).

Clivaz, X., et al., "1.5 $\mu$m Resolution optical low coherence reflectometry in biological tissues", *SPIE Proc.*, vol. 2083, No. 19, pp. 1–9 (1994).

Danielson, B. and C. Wittenberg, "Guided–wave reflectometry with micrometer resolution", *Applied Optics*, vol. 26, No. 14, pp. 2836–2842 (Jul. 15, 1987).

De Souza, E. et al., "Spectrally sliced WDM using a single femtosecond source", *Applied Optics*, vol. 34, No. 25, pp.

Fercher, A. et al."Eye–length measurement by interferometry with partially coherent light", *Optics Letters*, vol. 13, No. 3, pp. 186–188 (Mar. 1988).

Fujimoto, et al., "High resolution in vivo intra–arterial imaging with optical coherence tomography." *Heart*, vol. 82, No. 2, pp. 128–133 (Aug. 1999).

Fujimoto, et al., "New technology for high–speed and high–resolution optical coherence tomography" *Advances in Optical Biopsy and Optical Mammography*, vol. 838, pp. 95–107 (1998).

Fujimoto, et al., "Optical biopsy and imaging using optical coherence tomography." *Nature Medicine*, vol. 1, No. 9: pp. 970–972 (Sep. 1995).

Gelikonov, V. et al. "Coherent optical tomography of microscopic inhomogeneities in biological tissues", *JETP*, vol. 61, No. 2, pp. 158–162 (Jan. 25, 1995).

Gilgen, H. et al. "Submillimeter Optical Reflectometry", *Journal of Lightwave Technology*, vol. 7, No. 8, pp. 1225–1233 (Aug. 1989).

He, Z. et al., "Selective image extraction by synthesis of the coherence function using two–dimensional optical lock–in amplifier with microchannel spatial light modulator", *IEEE Photonics Technology Letters*, vol. 9, No. 4, pp. 514–516 (Apr. 1997).

Hee, M. et al. "Quantitative assessment of macular edema with optical coherence tomography", *Archives of Ophthalmology*, vol. 113, pp. 1019–1029 (Aug. 1995).

Hee, M. et al., "Polarization–sensitive low–coherence reflectometer for birefringence characterization and ranging", *Journal Optical Society of America B*, vol. 9, No. 6, pp. 903–908 (Jun. 1992).

Herrmann, et al., "High resolution imaging of normal and osteoarthritic cartilage with optical coherence tomography" *The Journal of Rheumatology*, vol. 26, No. 3, pp. 627–635 (Mar. 1999).

Herrmann, et al., "Two– and three–dimensional high–resolution imaging of the human oviduct with optical coherence tomography" *Fertility and Sterility*, vol. 70, No. 1, pp. 155–158 (Jul. 1998).

Hillerich, "Shape analysis and coupling loss of microlenses on single–mode fiber tips", *Applied Optics*, vol. 27, No. 15, pp. 3102–3106 (Aug. 1988).

Hitzenberger, C. "Optical measurement of the axial eye length by laser doppler interferometry", *Investigative Ophthalmology & Visual Science*, vol. 32, No. 3, pp. 616–624 (Mar. 3, 1991).

Hitzenberger, C. K. et al., "Measurement of Corneal Thickness by Laser Doppler Interferometry", *Investigative Ophthalmology & Visual Science*, vol. 33, No. 1, pp. 98–103 (Jan. 1, 1992).

Huang, D. et al. "Micron–resolution ranging of cornea anterior chamber by optical reflectometry", *Lasers in Surgery and Medicine*, vol. 11, pp. 419–425 (May 19, 1991).

International Search Report PCT/US00/40599 (7 pgs).

International Search Report PCT/US00/01228 (8 pgs).

Izatt, J. "Micrometer–scale resolution imaging of the anterior eye in vivo with optical coherence tomography", *Archives of Ophthalmology*, vol. 112, pp. 15841589 (Dec. 1994).

Izatt, J. A. et al. "Optical coherence microscopy in scattering media", *Optics Letters*, vol. 19, No. 8, pp. 590–592 (Apr. 15, 1994).

Kinsel et al. "Design and Calibration of an Electrostatic Energy Analyzer– Time–of–Flight Mass Spectrometer for Measurement of Laser–Desorbed Ion Kenetic Energies", *Journal American Society for Mass Spectrometry*, vol. 6, pp. 619–622 (1995).

Kobayashi, M. et al. "Optical fiber component characterization by high–intensity and high–spatial–resolution interferometric optical–time–domain reflectometer", *IEEE Photonics Technology Letters*, vol. 3, No. 6, pp. 564–566 (Jun. 6, 1991).

Kobayashi, M. et al. "Polarization–independent interferometric optical–time–domain reflectometer", *Journal of Lightware Technology*, vol. 9, No. 5, pp. 623–628 (May 5, 1991).

Mallery, J. et al. "Assessment of normal and atherosclerotic arterial wall thickness with an intravascular ultrasound imaging catheter", *American Heart Journal*, vol. 119, No. 6, pp. 1392–1400 (Jun. 1990).

Morioka, T. "Nearly penalty–free, <4 ps supercontinuum WDM pulse generation for Tbit/s TDM–WDM networks", *Proc. Optical Fiber Comm*, paper PD21–1–PD21–4 (1995).

Pitris, et al., "High resolution imaging of gynecologic neoplasms using optical coherence tomography." *Obstetrics & Gynecology*, vol. 93, No. 1, pp. 135–139 (Jan. 1999).

Pitris, et al., "High resolution imaging of the upper respiratory tract with optical coherence tomography." *Respiratory and Critical Care Medicine*, vol. 157, No. 5, pp. 1640–1644 (May 1998).

Potkin, B. et al., "Coronary artery imaging with intrvascular high–frequency ultrasound", *Circulation*, vol. 81, No. 5, pp. 1575–1585 (May 1990).

Prince, et al. "Ball–tipped fibers for laser angioplasty with the pulsed–dye laser",,,*Journal of Quantum Electronics*, vol. 26, No. 12, pp. 2297–2306 (Dec. 1990).

Puliafito, C. "Imaging of macular diseases with optical coherence tomography", *Ophthamology*, vol. 102, No. 2, pp. 217–229 (Feb. 1995).

Roper, et al. "In vivo detection of experimentally induced cortical dysgenesis in the adult rat neocortex using optical coherence tomography" *Journal of Neuroscience Methods*, vol. 80, No. 1, pp. 91–98 (Mar. 13, 1998).

Schmitt, J. et al. "Measurement of optical properties of biological tissues by low–coherence reflectometry", *Applied Optics*, vol. 32, No. 30, pp. 6032–6042 (Oct. 20, 1993).

Scmitt, J. et al. "Optical–coherence tomography of a dense tissue: statistics of attenuation and backscattering", *Phys. Med. Biol.*, vol. 39, pp. 1705–1720 (1994).

Sergeev, A. et al. "In vivo optical coherence tomography of human skin microstructure", *SPIE Proc.*, vol. 328, pp. 144–153 (1994).

Sergeev, et al. "High–spatial–resolution optical–coherence tomography of human skin and mucus membranes", *Conference on Lasers and Electro–Optics*, (May 1995).

Sorin, W. V., "Simultaneous Thickness and Group Index Measurement Using Optical Low–Coherence Reflectometry", *IEEE Photonics Technology Letters*, vol. 4, No. 1, pp. 105–107 (Jan. 1, 1992).

Swanson, E. A. et al. "High–speed optical coherence domain reflectometry", *Optics Letters*, vol. 17, No. 2, pp. 151–153 (Jan. 15, 1992).

Takada, et al., "New measurement system for fault location in optical waveguide devices based on an interferometric technique," *Applied Optics*, vol. 26, No. 9, pp. 1603–1605 (May, 1987).

Takada, et al., "Phase–noise and shot–noise limited operations of low coherence optical time domain reflectometry," *Appl. Phys. Lett.*, vol. 59, No. 20, pp. 2483–2485 (Nov., 1991).

Takada, K. et al. "Rayleigh backscattering measurement of single–mode fibers by low coherence optical time–domain reflectometer with 14 μm spatial resolution", *Appl. Phys. Letters*, vol. 59, No. 2, pp. 143–145 (Jul. 8, 1991).

Takada, K. et al. "Resolution control of low–coherence optical time–domain reflectometer between 14 and 290 μm", *IEEE Photonics Technology Letters*, vol. 3, No. 7, pp. 676, 678 (Jul. 1991).

Tateda, "Water penetration Sensing Using Wavelength Tunable OTDR,*" *IEEE Photonics Technology Letters*, vol. 3, No. 1, Jan. 1991, pp. 1–3.

Tearney, et al. "Optical Coherence Tomography in multiply scattering tissue," *SPIE* vol. 2389, pp. 29–34.

Tearney, et al. "In vivo endoscopic optical biopsy with optical coherence tomography", *Science*, vol. 276, pp. 2037–2039 (Jun. 1997).

Tearney, et al., "Optical biopsy in human gastrointestinal tissue using optical coherence tomography." *The American Journal of Gastroenterology*, vol. 92, No. 10, pp. 1800–1804 (Oct. 1997).

Tearney, et al., "Optical biopsy in human pancreatobiliary tissue using optical coherence tomography." *Digestive Diseases and Sciences*, vol. 43, No. 6, pp. 1193–1199 (Jun. 1998).

Tearney, et al., "Optical biopsy in human urologic tissue using optical coherence tomography." *The Journal of Urology*, vol. 157, No. 5, pp. 1915–1919 (May 1997).

Tearney, G. J., et al. "High–Speed phase–and–group–delay scanning with a grating–based phase control delay line", *Optical Letters*, Vo. 22, No. 23, pp. 1811–1813 (Dec. 1, 1997).

Vaidya, et al. "Sculpted optical silica fiber tips for use in Nd: YAG contact tip laser surgery: Part 1—Fabrication Techniques", *Optical Engineering*, vol. 31, No. 7, pp. 1404–1409 (Jul. 1992).

Weiner, A. M. et al. "High–resolution femtosecond pulse shaping", *Journal of Optical Soc. Am. B.*, vol. 5, No. 8, pp. 1553–1572 (Aug. 1998).

Yadlowsky, M. et al., "Multiple scattering in optical coherence microscopy", *Applied Optics*, vol. 34, No. 25, pp. 5699–5707 (Sep. 1, 1995).

Yock, P. et al. "Intravascular ultrasound guidance for catheter–based coronary interventions", *Journal of American College of Cardiology*, vol. 17, No. 6, pp. 39B–45B (May 1991).

Youngquist, et al., "Optical coherence–domain reflectometry: a new optical evaluation technique," *Optics Letters*, vol. 12, No. 3, pp. 158–160 (Mar., 1987).

Adamson et al., "A New Wave Guide for Use with a $CO_2$ Delivery System for Laparoscopic Surgery", The Journal of Reproductive Medicine : 875–878, Nov. 13–17, 1991.

Bail et al., "Optical Coherence Tomography with the "Spectral Radar"—Fast Optical Analysis in Volume Scatters by Short Coherence Interferometry", Proceedings of the European Biomedical Optics, BIOS Europe 96, paper 2925–30, Vienna Austria.

Bauer et al, "Small Diameter Laparoscopy using a Microlaparoscope", Human Reproduction, 10:1461–1464, 1995.

Chinn et al., "Optical Coherence Tomography using a Frequency–Tunable Optical Source", Optics Letters, 22: 340–342, Mar. (1997).

Dickensheets et al., "Micromachined Scanning Confocal Microscope", Opt. Lett., 21:764–766, 1996.

Dunn et al., "Multifiber Gradient–Index Lens Laser Angioplasty Probe", Lasers in Surgery and Medicine, 10:85–93, 1990.

Edelstein et al., "Rapid programmable 300 ps optical delay scanner and signal–averaging system for ultrafast measurements", 62: 579–583, Mar. 1991.

Eigensee et al., "A New Method of Short–Coherence–Interferometry in Human Skin (in vivo) and in Solid Volume Scatters", Proceedings of the European Biomedical Optics, BiOS Europe 96, paper 2930–28, 1996..

Evans et al., "Arterial Imaging with a New Forward–Viewing Intravascular Ultrasound Catheter: Initial Studies", Circulation, 89:712–717, 1994.

Fercher, "Optical Coherence Tomography", Journal of Biomedical Optics, 1:157–173 (1996).

Fork et al., "Real–time intensity autocorrelation interferometer", 17:3534–3535, Nov. 15, 1978.

Giniuas et al., "Endoscope with Optical Sectioning Capability", Applied Optics, 32, 2888–2890, (1993).

Gmitro et al., "Confocal microscopy through a fiber–optic imaging bundle", Optics Letter 19: 565–567, Apr. 15, 1993.

Goldberg et al., "Sonographically Guided Laparoscopy and Mediastinoscopy Using Miniature Catheter–Based Transducers", Ultrasound Med 12: 49–54, 1993.

Haberland et al., "Investigation of Highly Scattering Media Using Near–Infrared Continuous Wave Tunable Semiconductor Laser", SPIE Proceedings, 2389:1–10 (1995).

Hammer, D.X. et al., "Intraocular Laser Surgical Probe (ILSP) for Membrane Disruption by Laser–Induced Breakdown", Applied Optics, 36:1684–1693, 1997.

Heritage et al., "Picosecond pulse shaping by spectral phase and amplitude manipulation", Optics Letters 10: 609–611, Dec. 1985.

Hilleges et al., "Femtosecond laser pulse shaping by use of microsecond radio–frequency pulses", Optics Letters 19: 737–739, May 15, 1994.

Huang et al., "Optical Coherence Tomography", Science, 254:1178–1181 (1991).

Kohso et al., "An Investigation of an Infrared Ray Electronic Endoscope with a Laser Diode Light Source," Endoscopy, 22:217–220, 1990.

Kwong et al., "400–Hz mechanical scanning optical delay line", Optics Letters 18: 558–560, Apr. 1, 1993.

Martinez, "3000 Times Grating Compressor with Positive Group Velocity Dispersion: Application to Fiber Compensation in 1.3–1.6 $\mu$m Region", IEEE 23: 59–64, Jan. 1987.

Ng, K–H. et al., "Arterial Imaging with a New Forward–Viewing Intravascular Ultrasound Catheter: Three–Dimensional Reconstruction and Display of Data," Circulation, 89:718–723.

Pankatrov, M.M. et al,. "A Step–Zoom Probe for Laser Endophotocoagulation: Design", Ophthalmic Surgery, 18:61–65, 1987.

Park, M. Chodorow et al., "High Resolution Optical Ranging System", Applied Optics, 20: 2389–2394 (1981).

Piyaket et al., "Programmable ultrashot optical pulse delay using an acousto–optic deflector", Applied Optics 34: 1445–1453, Mar. 10, 1995.

Salathe, R.P. et al. "Coupled–mode propagation in multicore fibers characterized by optical low–coherence reflectometry," Opt. Lett., 21:1006–1008, 1996.

Schaub et al., "A New Fiber Optic Probe for Cellular Visualization", ASAIO Journal, 41:M665–M669, 1995.

Swanson et al., "Optical Coherence Tomography: Principles, Instrumentation, and Applications", XXIst Australian Conference on Optical Fibre Technology, Dec. 1–4.

Tearney et al., "Scanning Single–Mode Fiber Optic Catheter–Endoscope for Optical Coherence Tomography", 21:543–545 (1996).

Thurston et al., "Analysis of Picosecond Pulse Shape Synthesis by Spectral Masking in a Grating Pulse Compressor", IEEE 33: 682–695, May 1986.

Tomkinson et al., "Rigid endoscopic relay systems: a comparative study", Applied Optics 35: 6674–6683, Dec. 1, 1996.

Turnbull et al., "A 40–100 Mhz B–Scan Ultrasound Backscatter Microscopy for Skin Imaging", Ultrasound in Medicine and Biology 21: 79–88, Nov. 1, 1995.

Wang et al., "Characterization of Fluid Flow Velocity by Optical Doppler Tomography," Opt. Lett., 20:1337–1339, 1995.

Webb, "Optics for laser rasters", Applied Optics 23: 3680–3683, Oct. 15, 1984.

Weiner et al, "Programmable femtosecond pulse shaping by use of a multielement liquid–crystal phase modulator", Optics Letters 15:326–328, Mar. 15, 1990.

Yasa et al., "A Rapid–Scanning Autocorrelation Scheme for Continuous Monitoring of Picosecond Laser Pulses", Optics Communications 36:406–408, Mar. 1981.

* cited by examiner

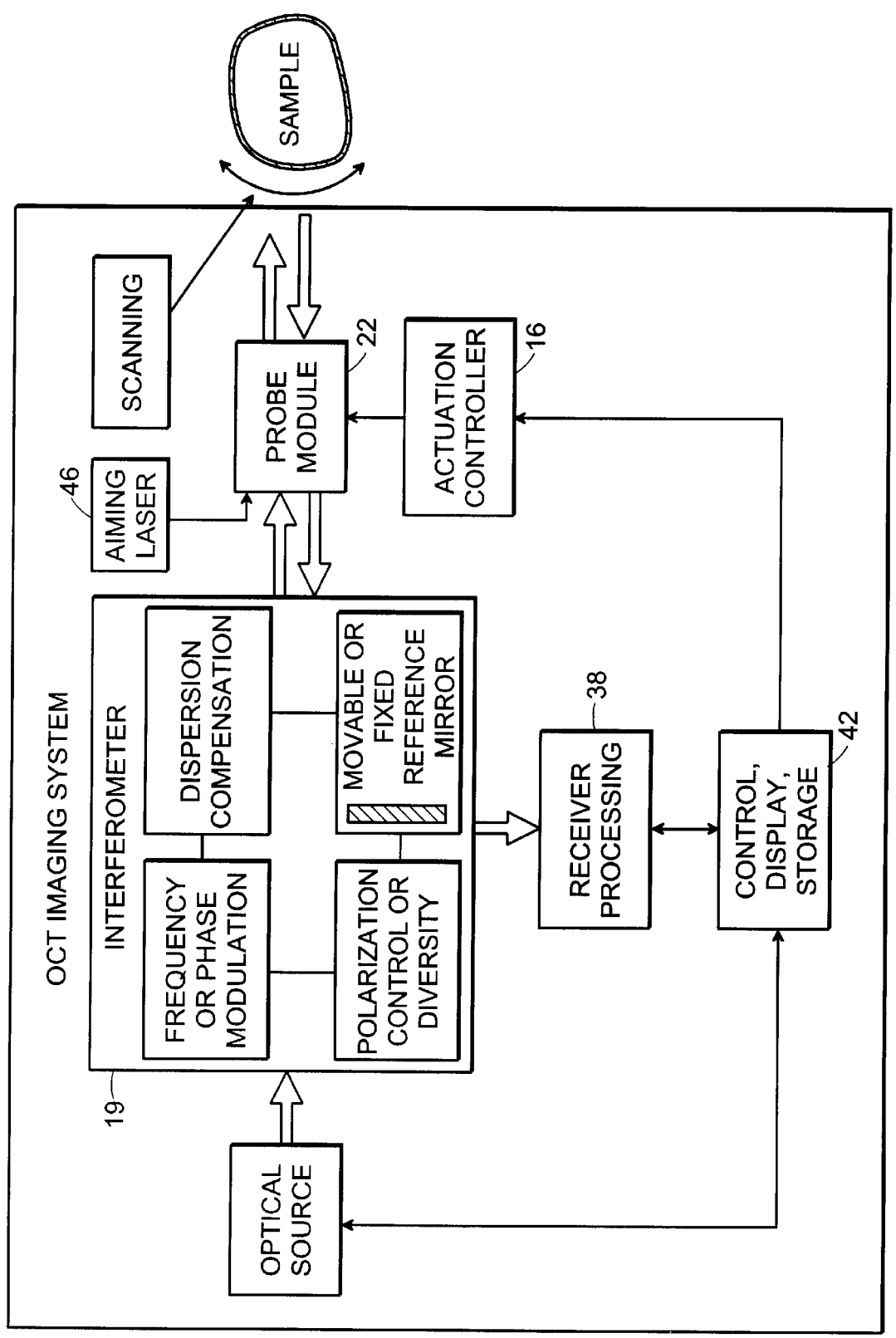
FIG. 1 EXAMPLE OCT IMAGING SYSTEM

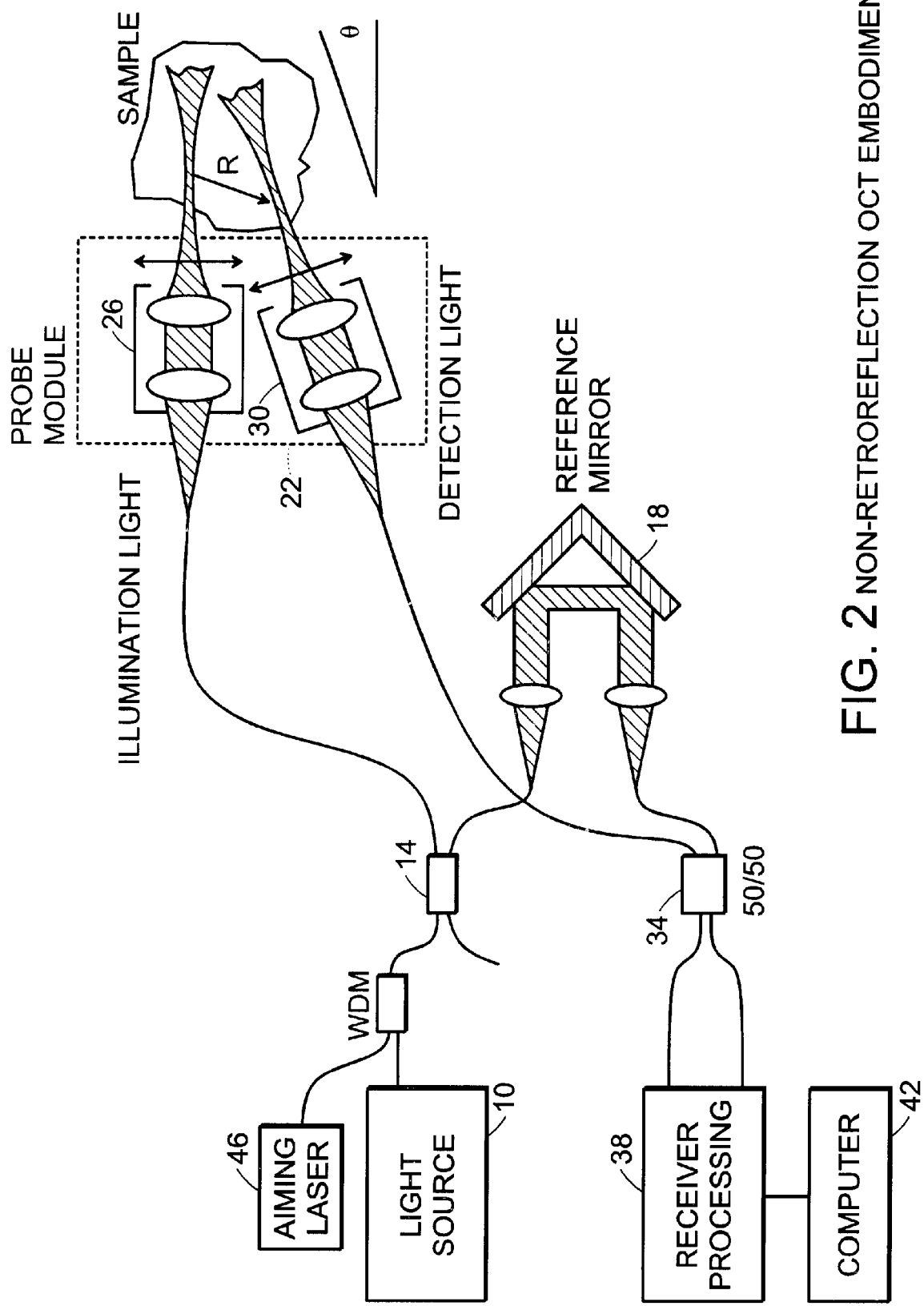
FIG. 2 NON-RETROREFLECTION OCT EMBODIMENT

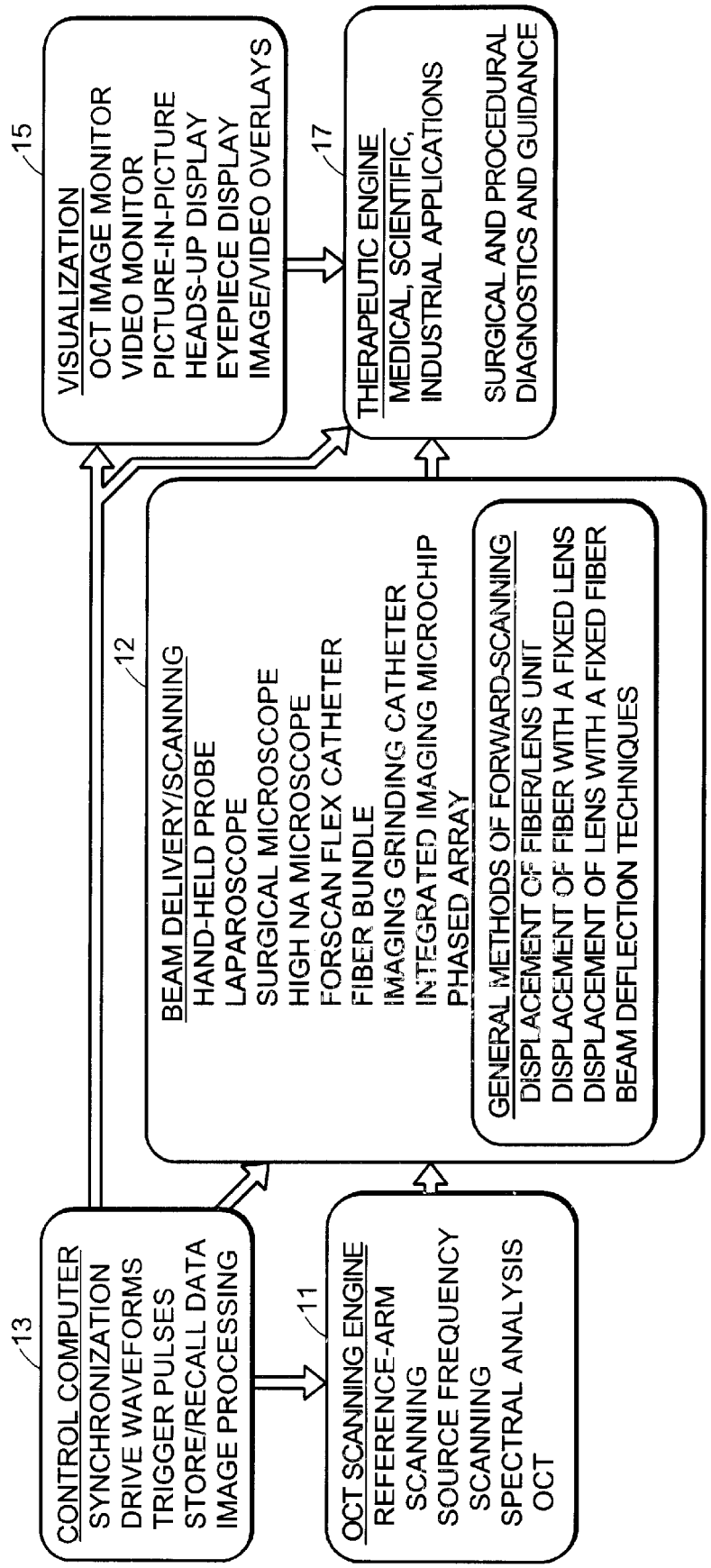
FIG. 3 MODULAR SYSTEM CONFIGURATION

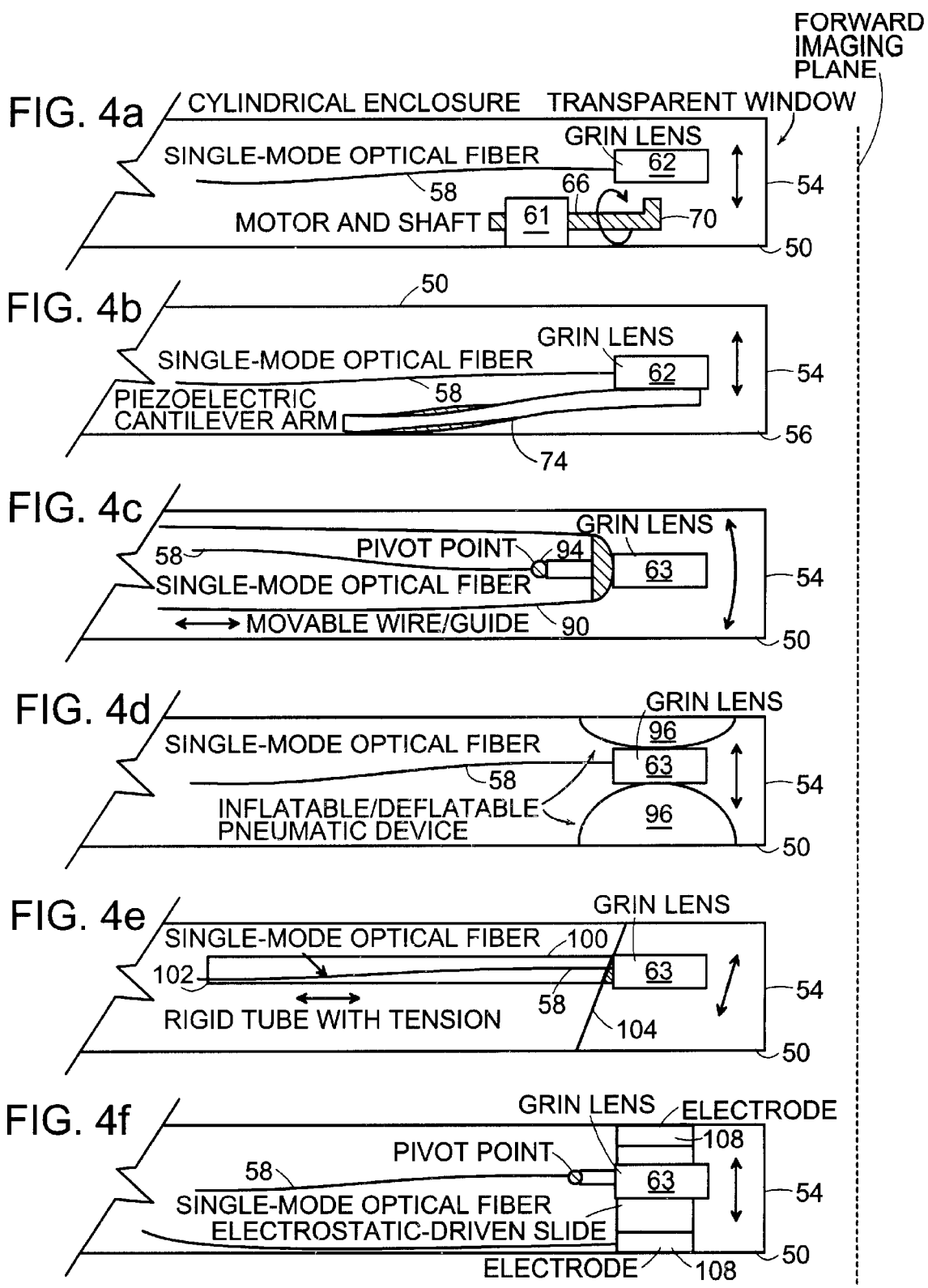
GENERAL METHODS TO MOVE FIBER/LENS UNIT

GENERAL METHODS CANTILEVER-BASED DISPLACEMENT

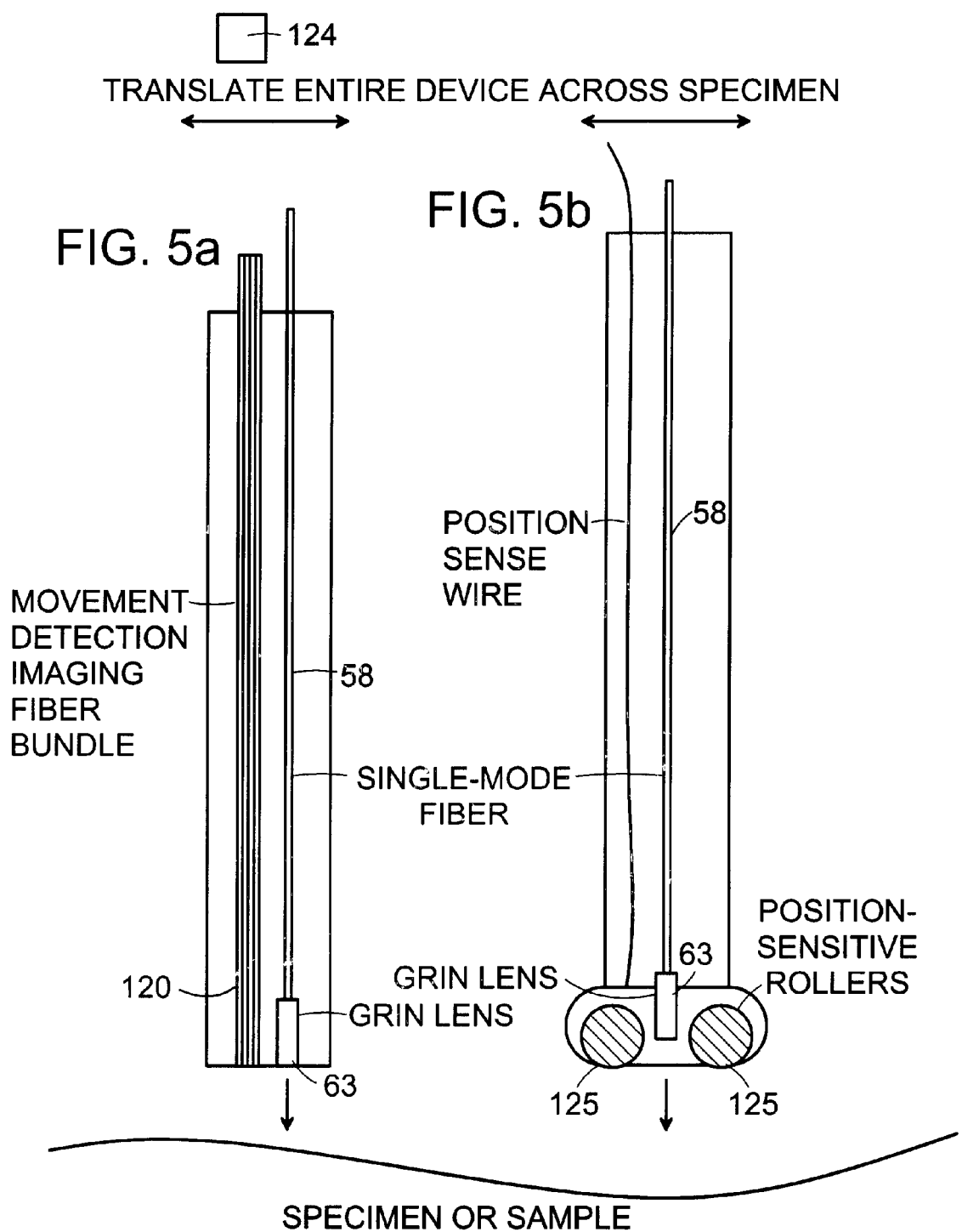

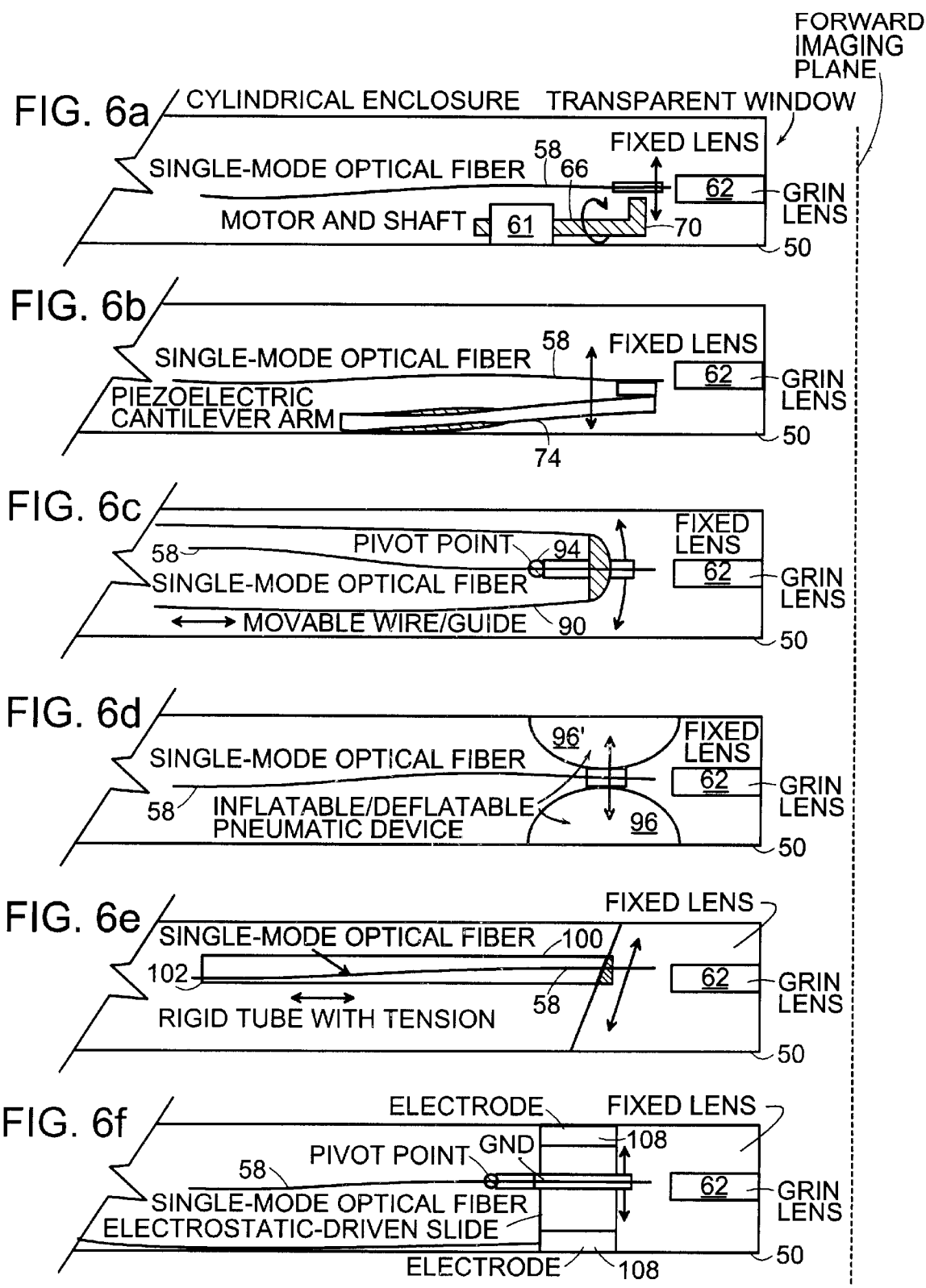
GENERAL METHODS TO MOVE FIBER WITH FIXED LENS

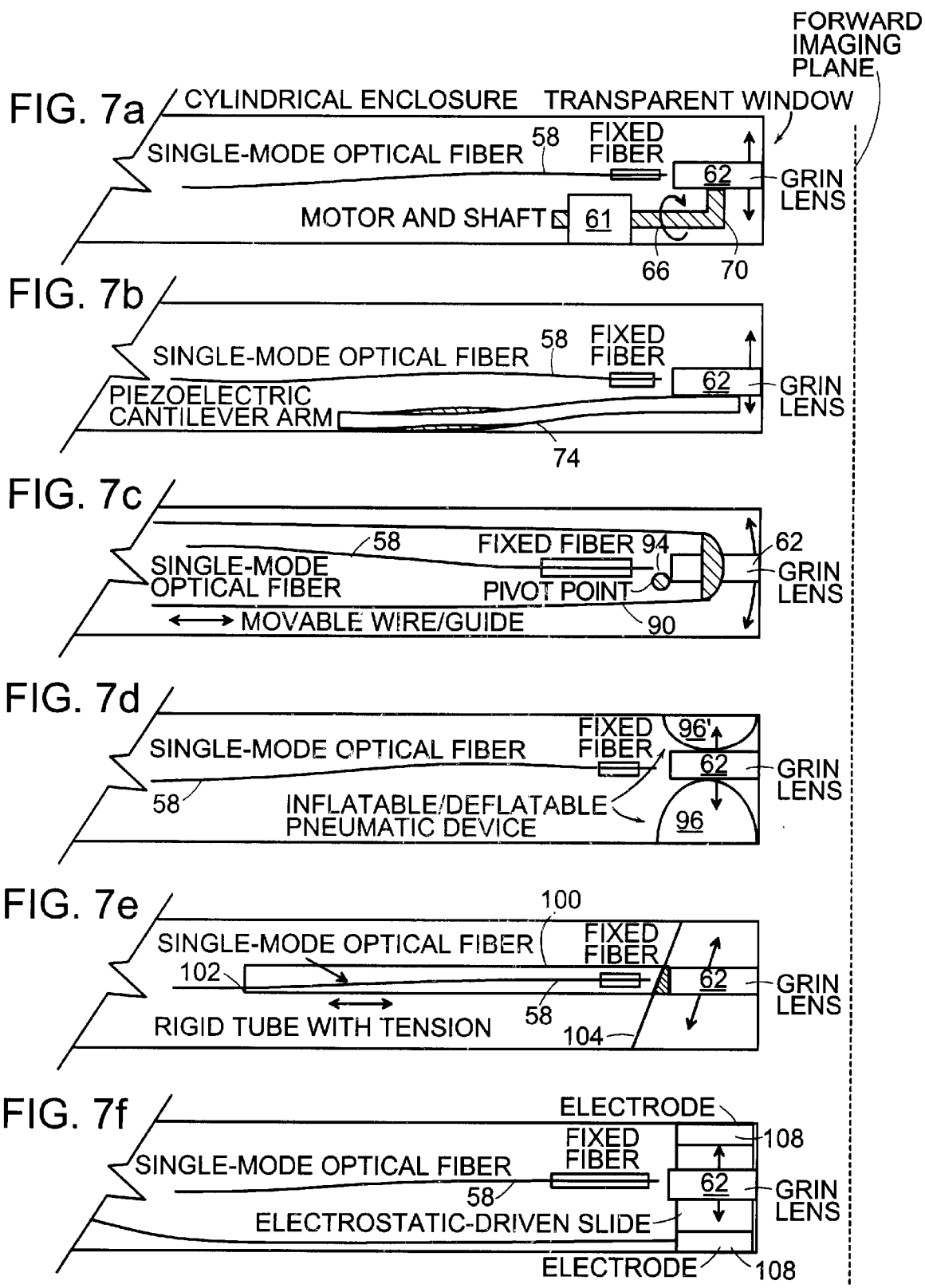
GENERAL METHODS TO MOVE LENS WITH FIXED FIBER

GENERAL METHODS FOR DEFLECTING IMAGING
BEAM IN FORWARD DIRECTION

GENERAL METHODS FOR DEFLECTING IMAGING
BEAM IN FORWARD DIRECTION

FIG. 9a

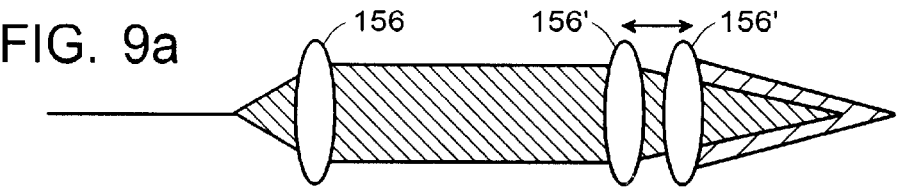

EXAMPLE OF FOCUS POSITIONING: MAINTAINS FOCUSING BEAM PARAMETERS SUCH AS SPOT SIZE, DEPTH-OF-FIELD, ETC. APPROACH SHOWN USES A TELESCOPE. SEVERAL ALTERNATIVE EMBODIMENTS ARE POSSIBLE SUCH AS MOVING THE ENTIRE PROBE MODULE

FIG. 9b

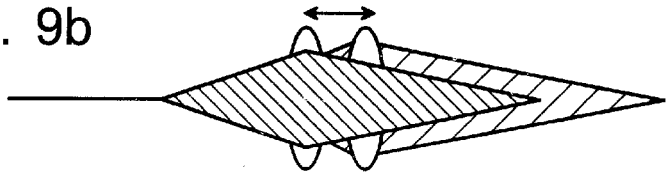

EXAMPLE OF FOCUS VARYING: CHANGES SPOT SIZE, DEPTH-OF-FIELD, AND WORKING DISTANCE. SEVERAL ALTERNATIVE EMBODIMENTS ARE POSSIBLE SUCH AS ZOOM LENS CONFIGURATIONS THAT DO NOT MOVE THE FOCAL POSITION.

FIG. 9c

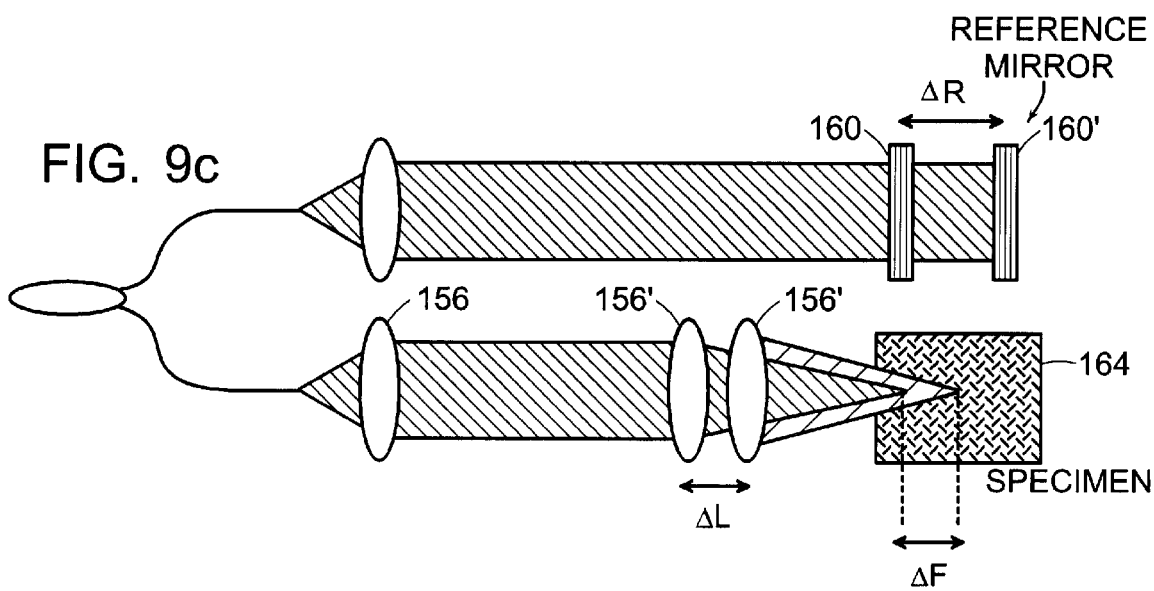

EXAMPLE OF FOCUS TRACKING: TO MAINTAIN HIGH LATERAL RESOLUTION IMPLIES A SHORTER DEPTH-OF-FOCUS. FOCUS TRACKING ADJUSTS THE REFERENCE ARM PATH LENGTH TO KEEP THE OVERLAP OF THE COHERENCE REGION WITHIN THE DEPTH-OF-FOCUS WITHIN THE SAMPLE. SEVERAL OTHER EMBODIMENTS ARE ALSO POSSIBLE.

FOCUS POSITIONING, VARYING, AND TRACKING

FORWARD-SCANNING HAND-HELD PROBE

FORWARD-SCANNING HAND-HELD PROBE WITH INTERCHANGABLE MAGNIFICATION

INTEGRATION OF HAND-HELD PROBE WITH SURGICAL SCALPEL FOR IMAGE-GUIDED SURGERY

FIG. 13 FORWARD-SCANNING HAND-HELD IMAGE/LASER SURGICAL PROBE

FORWARD-SCANNING LASER SURGICAL LAPAROSCOPE

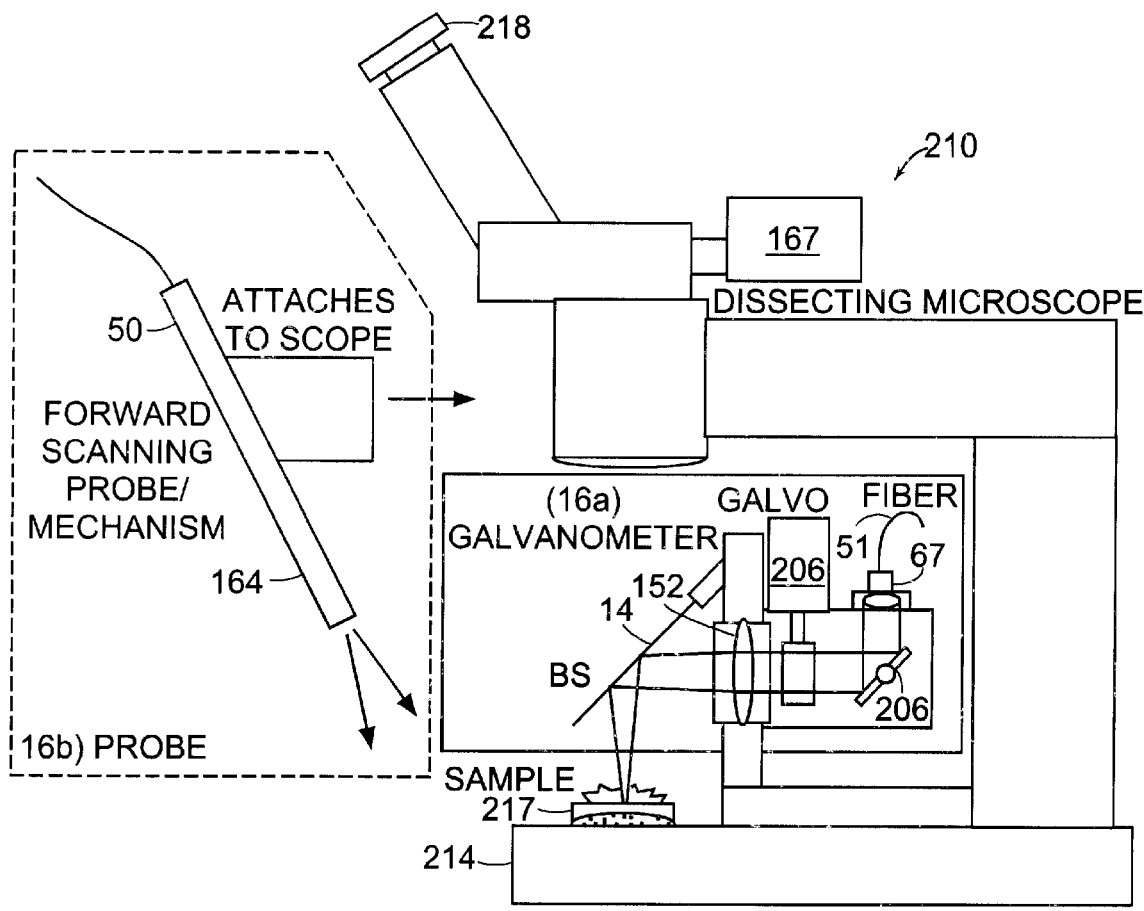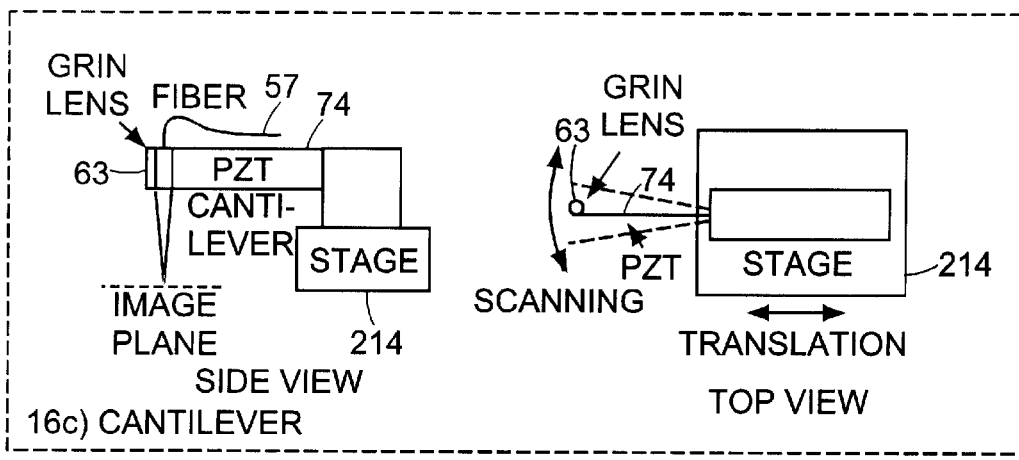
FIG. 16

HIGH NUMERICAL APERTURE OCT MICROSCOPE
17a) CAMERA/ILLUMINATION PORT ACCESS
17b) OBJECTIVE LENS ADAPTER ACCESS

IMAGING SURGICAL GRINDING CATHETER
21a) SIDE IMAGING/GRINDER

IMAGING SURGICAL GRINDING CATHETER
21b) FORWARD IMAGING/GRINDER

INTEGRATED MICROCHIP FOR IMAGE ACQUISTION

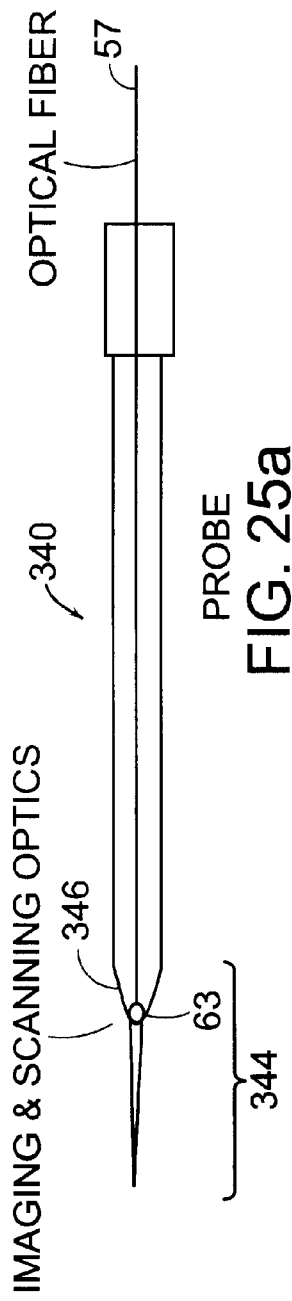
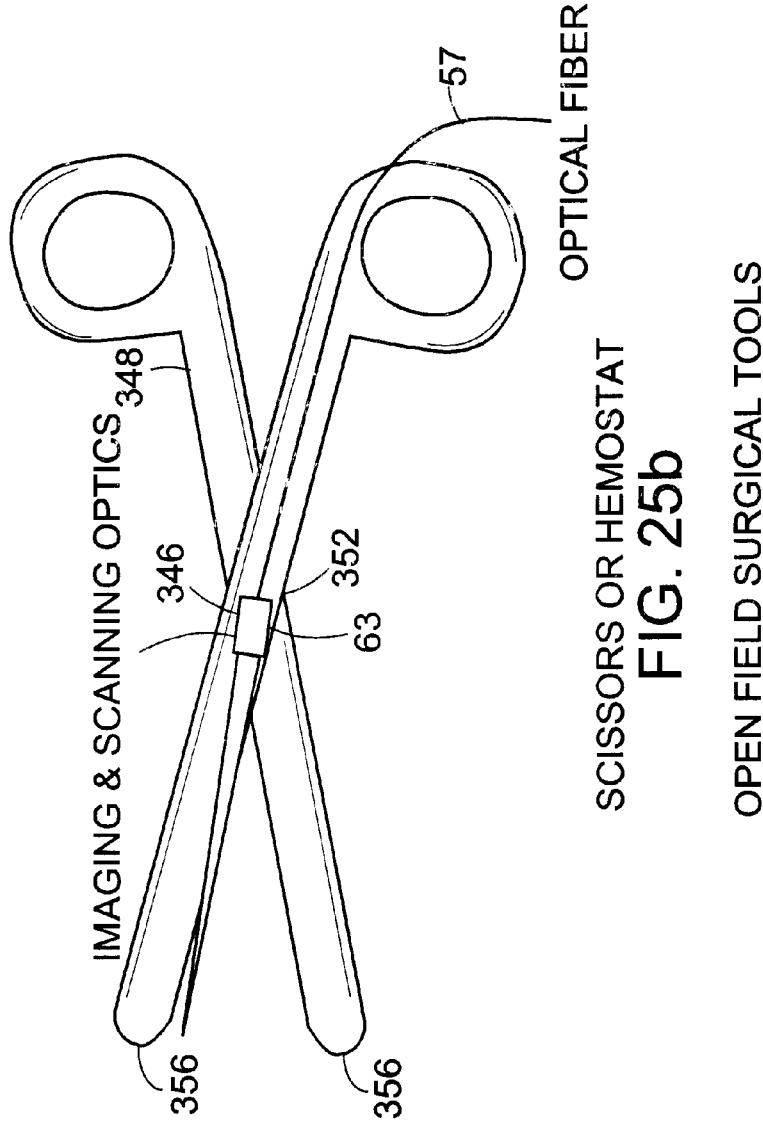
FIG. 25a PROBE
FIG. 25b SCISSORS OR HEMOSTAT
OPEN FIELD SURGICAL TOOLS

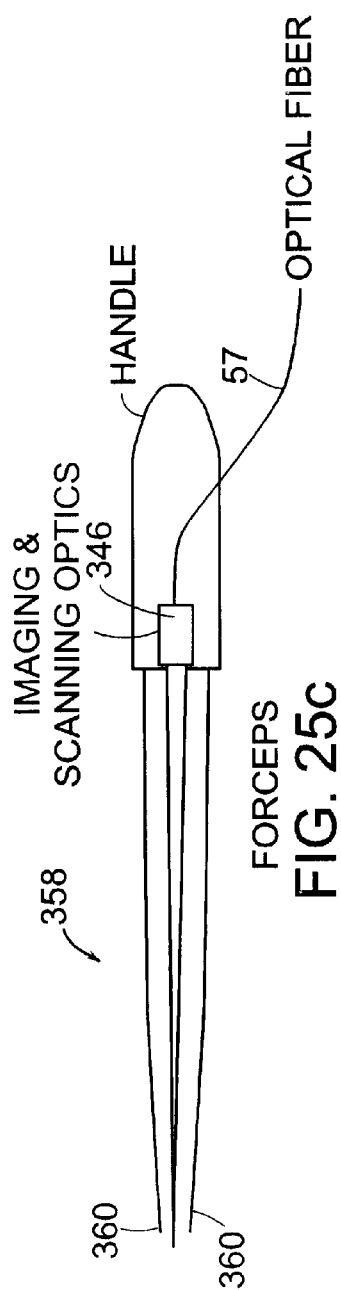
FIG. 25c FORCEPS
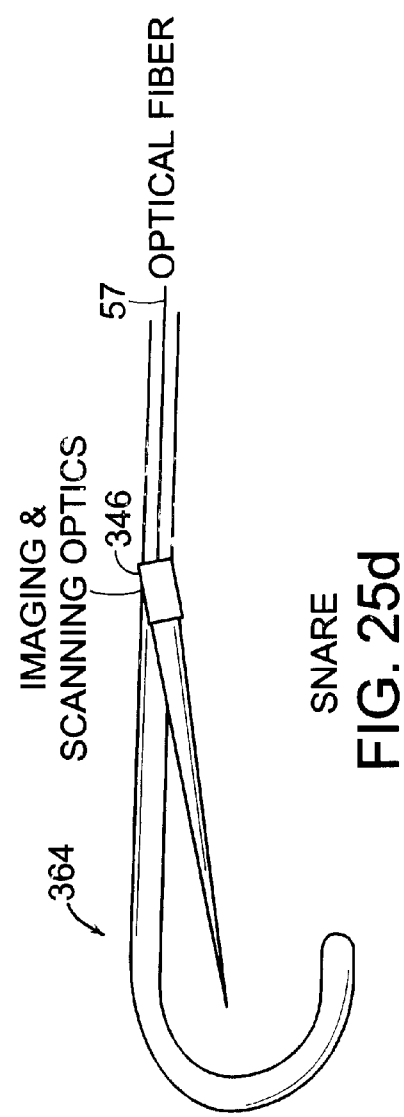
FIG. 25d SNARE
OPEN FIELD SURGICAL TOOLS

DISSECTING TOOLS/TISSUE PROBE

FORCEPS

SCISSORS

ENDOSCOPE SURGICAL TOOLS

PUNCH BIOPSY TOOL

SIDE VIEW    END VIEW
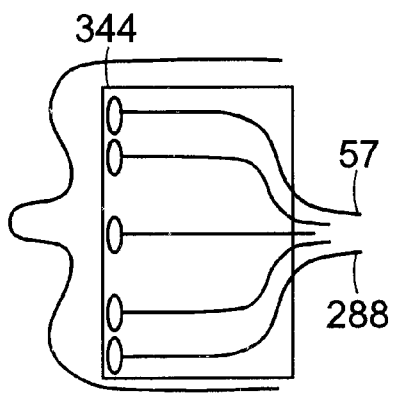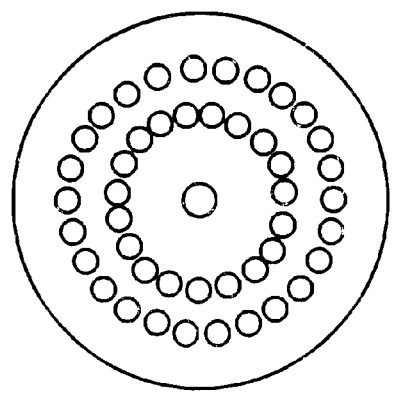
FIG. 28a
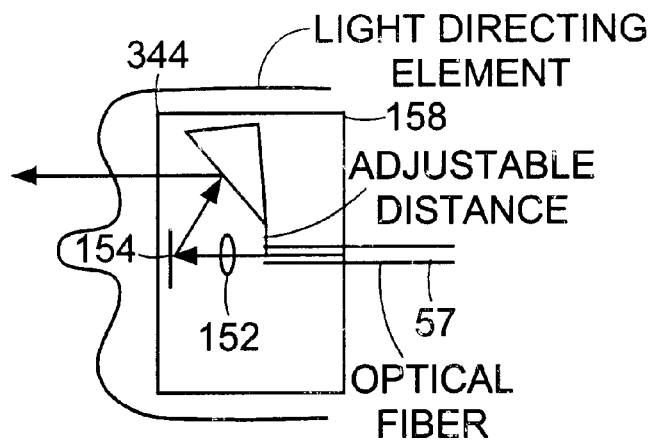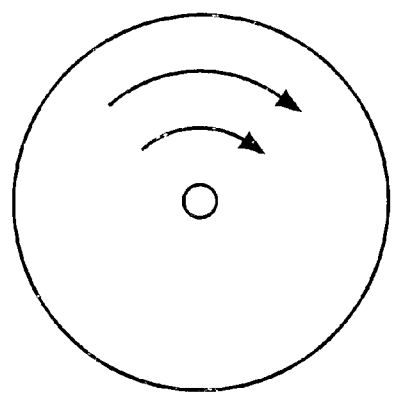
FIG. 28b
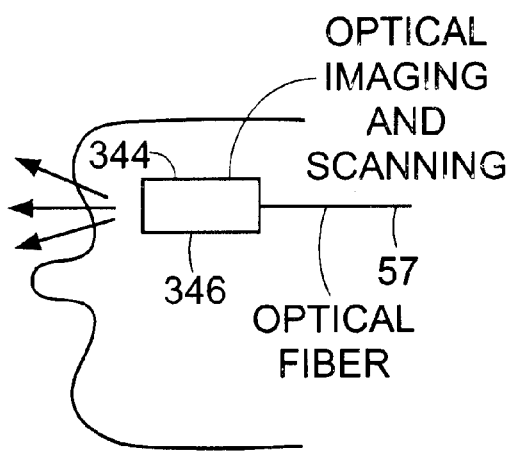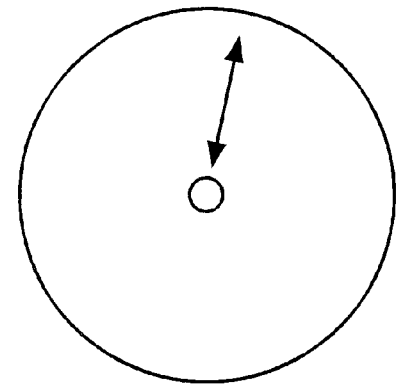
FIG. 28c

METHODS AND APPARATUS FOR FORWARD-DIRECTED OPTICAL SCANNING INSTRUMENTS

CROSS-REFERENCE TO RELATED APPLICATIONS

This is based on and claims priority to provisional U.S. patent application Ser. No. 60/038,047 which was filed on Mar. 6, 1997 and to provisional U.S. patent application Ser. No. 60/054,163 which was filed on Jul. 29, 1997.

This application also claims priority under 35 U.S.C. §120 as a continuation-in-part application to U.S. patent application Ser. No. 08/607,787, filed Feb. 27, 1996 now issued as U.S. Pat. No. 6,134,003, which is a continuation-in-part application of U.S. patent application Ser. No. 08/577,366, filed Dec. 22, 1995, now U.S. Pat. No. 5,748,598, and is also a continuation-in-part application of U.S. patent application Ser. No. 08/916,759, filed Aug. 19, 1997, now issued as U.S. Pat. No. 5,784,352, which is an FWC application of U.S. patent application Ser. No. 08/492,738, filed Jun. 21, 1995, now abandoned, and is also a continuation-in-part application of U.S. patent application Ser. No. 08/252,940, filed Jun. 2, 1994, now abandoned, which is a continuation-in-part of U.S. patent application Ser. No. 08/033,194, filed Mar. 16, 1993, now U.S. Pat. No. 5,459,570, which is a continuation of U.S. patent application Ser. No. 07/692,877, filed Apr. 29, 1991, now abandoned.

GOVERNMENT SUPPORT

This invention was made with government support under Grant Number N00014-94-1-0717 awarded by the Department of the Navy and Grant Number NIH-5R01-EY1189 awarded by the National Institutes of Health. The government has certain rights in this invention.

FIELD OF INVENTION

This invention relates generally to the field of optical imaging and more specifically to the field of optical image guided procedures.

BACKGROUND OF THE INVENTION

There is a pressing need for new high-resolution (~10 $\mu$m) imaging and visualization technology across a wide range of fields including medicine, medical and biological research, and materials and packaging research, development, and manufacturing. Improved visualization can enable new diagnostic capabilities such as in diagnostic screening of the esophagus for adenocarcinoma or in locating voids in multi-layer polymer packages. In addition, improved visualization enables new image guided procedures such as guiding an atherectomy catheter to remove small unstable plaques from a coronary artery without puncturing the arterial wall.

MRI, x-rays, ultrasound, and optics have all found important roles in imaging applications. In many applications optical imaging offers certain advantages over other approaches because it is non-ionizing, non-contact, and can achieve high resolution. There are a variety of types of optical imaging techniques concurrently available including optical coherence tomography (OCT) and other interferometric imaging techniques, fluorescence and other spectroscopic imaging techniques, Raman imaging, diffuse-wave optical imaging, and two-photon imaging techniques.

OCT is an interferometric imaging technology and thus has the properties of very high sensitivity and large dynamic range. OCT achieves depth resolution via a combination of the focal properties of the imaging optics used and the coherence properties of the optical source used. The use of OCT and other interferometric imaging modalities has three fundamental advantages over standard direct detection optical imaging techniques: 1) the ability to achieve nearly shot-noise-limited detection and thus high sensitivity (>140 dB), 2) the ability to achieve high dynamic range (>100 dB) as the received signal is proportional to the electric field, not the intensity as in direct detection, and 3) the ability to perform high-resolution phase-sensitive temporal gating yielding significantly improved depth discrimination (~1 $\mu$m).

Most previous work on scanning methods used in probe modules that attach to OCT or other optical imaging systems have focused on utilizing galvanometric or stepper based transverse scanning to produce multi-dimensional images. For instance, U.S. Pat. Nos. 5,459,570 and 5,321,501 describe several OCT imaging embodiments and their application in ophthalmology. These patents include methods which scan a beam in transverse patterns on the retina or on the anterior eye using galvanometer controlled mirrors or rotating mirrors. For endoscopes and catheters, methods have been described which scan a beam in a circumferential transverse direction perpendicular to the longitudinal axis of the catheter or endoscope. For example U.S. Pat. Nos. 5,393,467, 5,459,570 and 5,321,501 describe forms of these techniques.

SUMMARY OF THE INVENTION

It is an object of this invention to provide a forward directing imaging system that is useful for diagnostic and therapeutic intervention during medical procedures. The imaging system described has application to hand-held probes, laparoscopes, endoscopes, catheters, guidewires, trocars, microscopes, tissue probes, needles, scissors, scalpels, and other instruments either as "stand-alone" implementation or as a new implementation used in conjunction within, or external to, an existing instrument.

In one embodiment, the present forward directing imaging system includes forward directed optical coherence tomography (OCT) in a probe including a scanning mechanism. In another embodiment the system uses non-retroreflected OCT and includes a light source, a sample illuminator, a reference arm, a beam splitter, a sample light collector, a detector to generate a signal in response to incident light, and a beam combiner positioned to direct light from a sample light collector and a reference arm to a detector where output from the detector is analyzed by a computer.

In another embodiment the optical probe imaging system includes a scanning mechanism capable of causing a lens and optical fiber to move substantially orthogonally to the longitudinal axis of the housing. In one embodiment, the scanning mechanism includes a motor and a cam attached to the motor. The motor causes rotation of the cam moving the lens and optical fiber to orthogonally to the longitudinal axis of the probe housing to scan a sample. Other embodiments of the scanning mechanism which cause the lens and fiber to move orthogonally to scan a sample include a piezoelectric transducer, or by a wire around a pivot, pneumatic devices, or by an electrostatically driven slide.

In another embodiment of the optical imaging system, the scanning mechanism includes counter rotating prisms or rotating offset lenses that generate arbitrary scanning patterns on a sample.

In another embodiment of the invention the forward scanning OCT imaging system may be applied in a handheld probe, or surgical tools such as probes, scalpels, scissors, forceps and biopsy instruments. Embodiments of these devices include the application of surgical laser fibers.

In yet another embodiment, the optical probe is an endoscope used to examine natural orifices, canals, tubes, ducts and vessels of the body. The invention contemplates a surgical grinding endoscope which uses a cutting element in the forward or side direction combined with the forward imaging capabilities of the optical probe.

In another embodiment of this invention, the OCT imaging system is used with a laparoscope to perform diagnostics and surgical procedures within body cavities. The laparoscope embodiment also contemplates the use of forward scanning lasers.

In still another embodiment of the invention, the imaging system is applied to a surgical microscope for procedures requiring an en face as well as a cross sectional view into the tissue. The imaging system is also applied to a high numerical aperture microscope in yet another embodiment of the invention Another important embodiment of the invention is for therapeutics such as atherectomy, transurethral prostatectomy, and cervical imaging. It is contemplated that the optical probes of this invention are implantable to allow for continuous or periodic extraction of information from the tissue site where implanted.

BRIEF DESCRIPTION OF DRAWINGS

FIG. 1 is a block diagram of an embodiment of an OCT imaging system.

FIG. 2 is a block diagram of an embodiment of a Non-Retroreflected OCT configuration.

FIG. 3 is a block diagram of the modular system configuration.

FIGS. 4a–i are crossectional views of embodiments of a catheter with forward scanning capabilities.

FIGS. 5a and 5b are longitudinal sectional views of embodiments of devices which permit forward scanning by translation.

FIGS. 6a–f are longitudinal sectional views of embodiments of a catheter that utilizes a fixed lens and movable fiber for forward scanning.

FIGS. 7a–f are longitudinal sectional views of embodiments of a catheter that utilizes a fixed fiber and movable lens for forward scanning.

FIGS. 9a–c are longitudinal sectional views of embodiments of imaging beam characteristics.

FIG. 16 is a longitudinal sectional view of an embodiment of a surgical/dissecting microscope with multiple scan methods.

FIGS. 25a–d are longitudinal sectional views of embodiments of surgical tools and probes.

FIGS. 28a–c is a longitudinal and cross-sectional view of embodiments of devices for cervical imaging.

DETAILED DESCRIPTION OF THE INVENTION

Figure 4G:
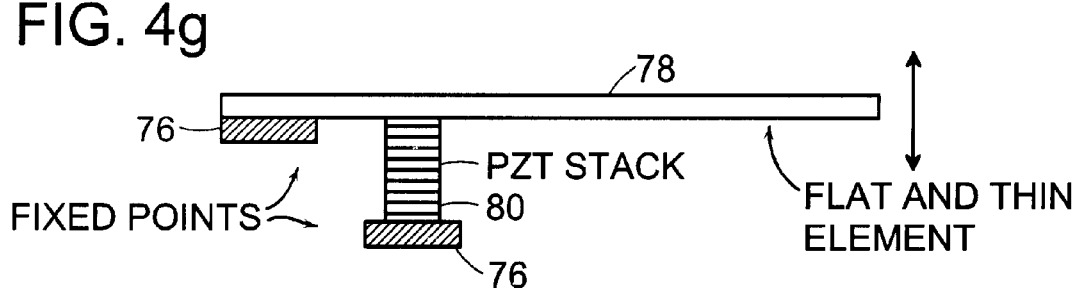

The imaging engine can be of a variety of embodiments including optical coherence tomography or other interferometric imaging systems, fluorescence and other spectroscopic imaging systems, Raman imaging, diffuse wave optical imaging, two photon imaging systems or combinations thereof. The imaging engine includes the associated imaging system sub-systems such as optics, electronics, motors, computers, and controls necessary to generate high resolution images, control image acquisition, and to process, quantitate, and display images, and manage databases.

As illustrated in FIG. 1 light from an optical source 10 is directed to a given position on a specimen to be imaged, ranged, or otherwise measured via a probe module. Interferometric techniques 19 can be used to collect and detect light altered by the internal microstructural features in the specimen in addition to the other techniques mentioned above. The interferometric imaging technique is often of an embodiment where the optical beam directed onto the specimen is spatially coherent, having a single-spatial mode, and thus the delivery system can be from a single-mode fiber. The detected light is processed in a receiver processor 38 to extract information on the specimens optical properties as a function of depth or other spatial metrics (e.g. location of incident beam on the sample). For instance, a reflectivity profile, or plot of the sample reflectivity as a function of depth, can be obtained. The probe module may include methods for performing scanning of the radiation pattern. Thus, by performing repeated measurements while scanning the incident optical beam at a plurality of points on the specimen image information can be obtained. Alternatively, images can be acquired in parallel.

Three basic types of OCT imaging engines are known in the art and include: reference-arm scanning, frequency tunable optical source, and optical spectral analysis imaging. In each of these embodiments the interferometer 19 and associated optics are used to couple light from the optical source onto the sample and optical reference. The interferometer 19 also couples light after being altered by the sample and optical reference (either delayed, transmitted, reflected, or scattered) onto the receiver processing unit 38 in such a way that optical interference between the sample and reference light occurs and is detected and converted to electronic signal(s). The interferometer may contain free-space optics and/or optical fibers. In one embodiment the fibers are single-mode fibers. The interferometer may be of a variety of embodiments including Michelson or Mach-Zehnder configurations. Within the interferometer frequency or phase modulation elements enable en face imaging or enhanced signal processing; dispersion balancing and compensation elements maintain high longitudinal resolution; and polarization controllers, polarization-maintaining or single-polarization fiber, or polarization diversity techniques maintain good signal-to-noise ratio or provide information concerning the birefringence of the sample.

Transverse (including lateral, axial, or radial) scans are acquired using the actuator to scan the optical radiation emitted from the probe unit into the sample and from the sample into the probe unit. For OCT imaging engines, depth (or longitudinal) scans are acquired using one of the three methods mentioned above and described below. The computer controls the interaction between transverse and depth scanning to generate 1,2 or 3 dimensional images. The OCT images represent information on the microstructural optical properties of a sample. These include index-of-refraction discontinuities, scattering, absorption, birefringence, dispersion, and spectra-scopic properties of a sample. The properties can be spatially resolved using a variety of scanning techniques. Such techniques include performing sequential depth scans interlaced with transverse scans or vise versa or the images can be acquired in parallel. Because rapid images can be obtained, the extensions beyond 1, 2, or 3-D imaging are possible with this invention. In particular, by visualizing images over time, functional imaging is possible. For example, the visualization of a beating embryo heart in response to various stimulants can be achieved.

In the reference arm scanning OCT embodiment, a mode-locked, superluminescent or other suitably broad-bandwidth optical source is used and coupled to the interferometer. By mechanically scanning the reference arm path length, reflectivity profiles of the sample can be obtained. There are a variety of known methods for reference arm scanning including linear translators, galvanometers, fiber stretching, rotating elements (mirrors, cams, and glass blocks), and grating based delay line scanning. Only when the reflections from the sample and reference arm path lengths are equal to within the source coherence length is optical interference detected. Thus by scanning the reference arm path length, depth resolved interferometric profiles of the samples optical properties can be obtained. The receiver processing unit 38 can consist of a single detector, dual-balanced detectors, or an array of photo-detectors followed by appropriate amplification and signal processing.

In another embodiment, a frequency tunable optical source is coupled to the interferometer. The receiver processing unit 38 includes photo-detectors which receive signals from the sample and reference reflections and detects any optical interference. The slight time delay between the arrival of these two signals, combined with frequency tuning, results in a beat signal from which the reflectivity or other interferometric profile of the sample's optical properties can be derived using rf spectral analysis techniques. There are several methods for performing a wide frequency sweep including mechanically or electronically tuned external cavity lasers, current or temperature tuned semiconductor lasers, multi-section semiconductor lasers, and broadband amplified spontaneous emission sources combined with tunable optical filters.

In another embodiment of optical spectrum analysis OCT, the source is again a broad bandwidth source coupled to an interferometer. Reflections from the sample/specimen and reference reflection(s) will optically interfere at the receiver, which is an optical spectrum analyzer. The optical spectrum will consist of fringe profiles, the contrast of which is proportional to the reflection coefficients within the sample and the period of which is proportional to the relative distance between the sample and the reference reflection(s). Using various signal processing algorithms such as Fourier analysis the reflectivity or other interferometric profile of the optical properties of the sample can be obtained. There are a variety of known methods for performing spectral analysis including single or multiple gratings or prisms combined with scanning detector systems or array detectors and narrow-band tunable filters.

Obtaining a high power and broad bandwidth source for OCT is difficult. In one embodiment, the source is a Raman pumped master-oscillator power amplifier (MOPA) source. Raman amplifiers are commonly used in Wavelength Division Multiplexing (WDM) optical communications systems and their use can be extended to OCT sources. Using a strong CW or pulsed pump laser one can create a broadband optical power amplifier at the Stokes shift away from the pump laser (~13 THz). If this amplifier is seeded with a lower power semiconductor, fiber, or other broadband master oscillator source then it will be amplified to a higher power. If more than one Raman pump is used, and the Raman pumps are spaced by approximately the Raman gain bandwidth, then the bandwidth of the amplifier will be broadened, approximately, by a factor of two. Additional pumps can be used to further broadened the amplifier bandwidth and the gain spectra associated with the individual pumps can be tailored to shape the gain spectra by tailoring their respective pump powers.

The master oscillator can be tailored to be very broadband by using in-fiber Bragg or long period fiber gratings or using WDM multiplexing techniques. A Faraday isolator can be used between the master oscillator and the power amplifier to maintain good stability. The pump laser can be derived from a cladding pumped Yb or Nd fiber or other rare earth doped fibers pumped from broad area or other semiconductor lasers as is known in the art. These lasers lase at ~1.1 $\mu$m and they can be used to pump Er:Yb fiber to create a Raman pump laser at a wavelength around 1.55 $\mu$m. This is suitable for generating an OCT Raman source at ~1.6 $\mu$m, or it can be used to create multiple Stokes shifted pumps using a series of in-fiber Bragg gratings to create a OCT Raman source around 1.3 $\mu$m.

Referring again to FIG. 1 often in applications of this invention the optical source 10 used is invisible to the human eye. In order to aid in the utility of this invention it is necessary to add a visible aiming laser 46 that is co-aligned with the source. This co-alignment can be obtained using a dichroic multiplexer or other suitable beam combining techniques. This aiming laser can be directly visualized by a human operator using a hand-held probe or surgical microscope or other embodiments of this invention. Alternatively, a special imaging camera, capable of detecting radiation unseen by the human eye, can be used to visualize the optical source radiation. Either the visible aiming laser or the imaging from the special camera can be used to feed the visualization sub-system described in the next section and is key to performing several diagnostic and therapeutic medical procedures.

The OCT systems do not necessarily need to operate in direct retro-reflection off of the specimen/sample. Referring to FIG. 2, the optical source 10 is coupled to a 2:2 fiber optic splitter 14 containing paths to a reference mirror 18 (corner cube) and to a probe unit 22 that illuminates the sample. Additional sources or aiming laser could be connected to unused coupler 14 (not shown). The beam waist of the illumination port 26 of the probe unit 22 is offset from the beam waist of the receiver port 30 of the probe unit 22 by a three dimensional vector R and a two dimensional coordinate rotation $\Theta$. The light from the receivor port 30 is recombined with the light reflected from reference mirror 18 into a 50/50 optical combiner 34 to form signals that enter the receiver processor 38 whose output is analyzed by a computer 42.

In typical OCT systems, $R=\Theta=0$ and the path of light to the specimen is the path of light from the specimen. However, in certain applications it may be desirable to offset the illumination and detected light fields. Furthermore, the scanning of the two light fields can thus be independent. For example, to produce shadowgrams analogous to those produced in X-ray systems one can set the illumination 26 and receiver ports 30 of the probe unit 22 directly opposite one another ($\Theta=180°$ and $R=0$ so that the beam waists overlap) and laterally scan the specimen. Such an embodiment may be useful in microscopic and other applications. This information derived using the signal processing is now not a reflectogram but a measure of the time delay through the sample. Information on group delay, index of refraction, scattering, and absorption coefficient can be obtained. This embodiment can be readily integrated into the microscope and other devices described in the following sections.

One of the key distinctions of this embodiment of the invention is that the OCT system does not need to operate in retro-reflection mode which is implicitly or explicitly assumed in almost all prior art. Not only does this enable a new design alternative for OCT systems but it can enable extraction of new information. For example, in previous direct retro-reflected embodiments often a large surface reflection, at, for example, an air/skin interface, can mask all the weaker reflections from just below the surface; a condition known as a blindness limitation. By operating in non retro-reflection this surface reflection is eliminated. Scattering is dependent on angle. Thus by setting $\Theta \neq 0$ a new measurement of the sample's optical properties can be obtained. In fact, in one aspect of this invention, $\Theta$ could be scanned to produce an image of the interferometric optical properties of the sample as a function of scattering angle. All three of the OCT imaging engine embodiments described above as well as other optical imaging techniques can be used with this non-retroreflection feature. This non-retroreflection embodiment may be realized using two single-mode fibers side-by-side or twin-core optical fiber.

Although much of the discussion in this section has focused on OCT imaging engine embodiments, a variety of other optical imaging engines can be used with the scanning and probe modules described in this invention. These include: transillumination techniques, diffuse-wave imaging techniques, confocal microscopy, and various types of fluorescence discrimination and imaging techniques. Diffuse-wave imaging is a fairly new optical imaging technology that uses the diffusion properties of highly scattered light to perform imaging. Diffuse-wave imaging has demonstrated clinical applications for functional monitoring such as for the determination of oxygenation. An interferometer is not required for diffuse-wave imaging. The source is often a sinusoidally intensity modulated laser and the receiver is a direct detection receiver that measures the relative intensity and phase of the detected light with respect to the transmitted light. The delivery system need not be a single-mode fiber and often a multi-mode fiber offers superior signal collection. Images of the specimens' optical properties can be obtained by plotting the phase or magnitude of the detected optical intensity as a function of scan location. As with the OCT imaging engine, the images are displayed and used for diagnosis or in guiding therapeutic procedures.

Laser induced fluorescence imaging is another attractive imaging engine technology suitable to the probes and scanning techniques of this invention. Fluorescence based medical discrimination or imaging technology can be successful in a number of clinical diagnostic applications. Fluorescence imaging is based on using short wavelength visible light to excite native fluorescence (or fluorescence from selectively bound exogenous chromophores) in tissues. Differences in the biochemical constituents of the tissue will produce differences in fluorescence spectra. These differences in spectra are typically assessed either at a set of discrete points across the optically accessible tissue surface or as an image of the tissue surface. Differences in fluorescence are then interpreted with an algorithm in order to differentiate the pathology of the tissue. Typically, the desired endpoint is to assess the presence of dysplasia or cancer. An interferometer is not required for this engine technology nor are single-mode optical fibers. The source could consists of a short wavelength excitation laser and the receiver would consist of optical spectrum analysis of one or more regions tuned to the fluorescence wavelength. As the incident excitation radiation and collected fluorescence radiation is scanned, optical images of the specimen are obtained, displayed, and used for diagnosis or in guiding therapeutic procedures.

Similarly applications of the probe-module scanning designs and concepts described in this invention are applicable to other imaging engines such as Raman, two-photon, multi-photon, confocal microscopes, etc. Furthermore, these probe-module scanning designs can be use as stand alone therapeutic devices without the aid of an embedded imaging technology.

Most importantly, it is possible to utilize multiple imaging technologies sequentially, in parallel, or simultaneously over the same scanning probe module. For instance, an OCT and fluorescence imaging engine could be used simultaneously over the same single-mode probe module optics. The OCT source and the short wavelength excitation laser could be combined using a fiber optic wavelength division multiplexer (WDM) coupler and the collected OCT light and fluorescence light could be separated using another WDM coupler. Simultaneous images of fluorescence and OCT could be displayed. Alternatively, the probe module could contain two fibers, one single-mode fiber for OCT imaging and one single or multi-mode fiber for fluorescence imaging. Common or separate scanning elements could be used to direct the respective radiation patterns. As the two imaging technologies contain distinct information, improved decision making in diagnostic or therapeutic procedures would be obtained.

The apparatus of one embodiment of this invention provides optical imaging by way of scanning an optical beam in linear, circular, and arbitrary patterns. Scanning is performed using a probe module of various designs coupled to an imaging system. From a systems perspective, the invention can be described in terms of: 1) Actuation techniques which translate, direct, or deflect the optical beam for the purpose of collecting data and obtaining an optical image; 2) A probe module which utilizes the actuation technique and which contains various optical components necessary to deliver the beam to or receive the beam from the specimen or sample to be imaged; 3) An imaging system to which the probe module is attached and contains the source of the light beam, detection electronics or instrumentation, means and methods for displaying the obtained image data, and all associated imaging sub-systems including optics, electronics, motors, controllers, and computers to control the incident light, detect the image signal, process the incoming data, and assemble the data to form a one, two, three, or four dimensional data set and image; 4) Implementation methods which combine all the elements of this invention in a user-friendly, beam deliverable device—where such a device may be an independent instrument developed using this invention or the device may be an accessory to, or integrated with, an established research or clinical instrument, tool, or device; and 5) A therapeutic system which is coupled to the imaging system to perform minimally invasive imaging guided procedures.

A modular system as contemplated by the invention is diagrammed in FIG. 3. The Beam Delivery/Scanning Module 12 which includes the general forward-scanning (or other types of scanning e.g. radial, lateral, or axial) methods which are described in detail herein. Various methods are used to scan or translate the optical beam in order for the system to collect data and form an image. These general forward-scanning methods include any number of beam delivery or probe modules including, but not limited to hand-held probes, laparoscopes, surgical microscopes, high numerical aperture or standard microscopes, forward-scanning flexible catheters, fiber bundles, or phased arrays. For each of these implementations, the forward-scanning method may: be directly integrated with the existing optical system, as with the laparoscope and microscopes; function as an independent imaging device such as the hand-held probe; function as a flexible catheter; function as a phased array; or function as an attachment which inherently adds to the functionality of the research or clinical instrument or tool as in the hand-held probe attached to the surgical scalpel to perform image-guided surgery.

An OCT Scanning Engine Module 11 includes a light source, axial (depth or range) scanning, and detection sub-system. Just as the Beam Delivery/Scanning Module 12 represents a modular component with interchangeable devices, so too does the OCT Scanning Engine Block 11. The three engines described above permit axial ranging to be performed within the optical system and components. The reference-arm scanning, source frequency scanning, and spectral analysis OCT all permit axial ranging, but perform this by distinctly different methods. Each of the three methods may be used in conjunction with any of the beam scanning methods. As noted earlier, several other optical scanning engines can be used including other interferometric imaging systems, fluorescence and other spectroscopic imaging systems, Raman imaging, diffuse wave optical imaging, two photon imaging systems or combinations thereof.

The OCT Scanning Engine Module 11 and the Beam Delivery/Scanning Module 12 are controlled by a Control Computer Module 13 typically including a central computer which is responsible for synchronization, generating drive waveforms, generating necessary trigger pulses, storing and recalling data, and any necessary signal and image processing. The control computer may also function as part of the last module, the Visualization Module, although this may be a separate entity.

The Visualization Module 15 receives the image data from the Control Computer Module 13, OCT Scanning Engine Module 11, and/or directly from the Beam Delivery/Scanning Module 12. Visualization may be performed with an OCT image monitor and/or a standard video monitor and/or a CRT. Generally, three screens are required for complete visualization: 1) a screen containing all the system parameters and settings to control the operation of the system, 2) a screen containing the video image of the tissue about to be imaged with OCT, and 3) a screen containing the OCT image of the specimen/sample. The video image is the en face surface view of the specimen, tissue, or sample, while the OCT image is a cross-sectional profile, en face, or other tomographic slice of the sub-surface morphology or structure. For full visualization, all screens may be visualized simultaneously on one monitor or video technology can be applied to permit picture-in-picture displays with various windows being called up on demand. Additionally, the video technology can permit integration with heads-up display allowing the user to view these screens via a head-mounted or semi-transparent window. Virtual reality may be incorporated with the given data screens. Heads-up display concepts can be integrated within the eyepieces of the microscopes allowing the user to visualize the OCT image and the cross-sectional, sub-surface morphology of the specimen without having to remove his/her eyes from the microscope and hence the specimen. Video technology may also permit such images to be overlaid thereby permitting the OCT image to be superimposed or fused over the video image with proper registration and alignment. The visible aiming laser described previously 1 can also be displayed in the Visualization Module 15. This visible aiming beam can be displayed on the screen containing the video image to allow registration of the OCT and video images by the user.

In addition to the three screens associated with the OCT imaging system, such visualization techniques will permit other critical data such as retrieval of previously acquired images and access to patient records while the procedure is being performed. Such systems can be readily integrated with existing computer networks and more powerful computers which would enable computationally-intensive tasks, such as three-dimensional display and manipulation to be performed off-site and downloaded to the user for visualization.

The Therapeutic Engine Module 17 is associated with medical, scientific, and industrial applications where image guided procedures are required. This module 17 uses the information output from the Visualization Module 15 to guide therapeutic procedures. This guidance can be through a human feedback aided by the Visualization Module 15 or autonomous via computer or other control mechanism in the Control Computer Module 13 or within the Therapeutic Engine Module 17 itself. Example applications where this imaging guide therapy would be beneficial include guidance of mechanical or laser-based atherectomy catheters, placing stents, inflating balloons using percutaneous angioplasty catheters, operating microsurgical tools during laparoscopy procedures, etc.

This multi-module systems approach introduces the overall design of this system and the forward-directed scanning methods of this invention. The forward-scanning methods, their implementation, and application will be described in detail in the following sections.

Forward-directed optical scanning can be performed via a number of methods. These methods are then incorporated into various instruments. In the most general description, the optical device will involve one or more optical fibers to deliver the light to the sample, focusing optics to focus the beam to the desired spot with a predetermined spot size and confocal parameter, and a means of translation to enable the acquisition of adjacent axial scans for the purpose of assembling a multi-dimensional image. Scanning methods can be generally, categorized as one of five general principles: 1) methods which move the fiber/lens as a single unit, 2) methods which move a fiber with respect to a fixed lens, 3) methods which move a lens with respect to a fixed fiber, 4) methods which deflect the forward-directed beam after the beam has been emitted from the fiber and focusing optics, and 5) combinations thereof.

1) Methods to Move Fiber/lens as a Single Unit

Several embodiments for moving the fiber/lens as a unit are shown in FIGS. 4a–f. For all of these designs, the forward-scanning optics and mechanicals are contained within, but not limited to, a cylindrical enclosure 50 that is small in diameter (~1–10 mm) such as a catheter, endoscope or laparoscope. This enclosure 50 may be rigid or flexible and readily integrated into the instruments discussed in later sections. The distal end of the enclosure 50 consists of an optional transparent window 54 that permits the optical beam to be transmitted with little attenuation while protecting the optics and mechanics from fluids and contaminants. Such an enclosure allows easy cleaning and sterilization. Distal to the tip of the enclosure lies the optical imaging plane. In the case of a single-mode optical fiber delivery this image plane may be the plane where the optical beam is focused to a minimum spot size. This plane should fall within the region of interest for the sample or specimen.

FIG. 4a describes an apparatus for mechanical translation of the fiber/lens unit. A single-mode fiber 58 is fixed to a GRIN lens 62 or a small diameter lens such as a ball lens at a given separation. This separation specifies the working distance to the focal plane, the spot size, and hence, the confocal parameter. Alternatively, the lens can be fabricated directly into the fiber forming a single focusing unit. The fiber/lens unit lies within a track (not shown) which permits the unit to slide back and forth in a linear translation. Mechanical translation is accomplished by a motor 61 and rotating shaft 66. Affixed to the shaft is an elliptical knob 70 or cam which displaces the fiber/lens unit with each rotation. A spring-apparatus (not shown) returns the fiber/lens unit back to its original location when not displaced by the elliptical knob 70. Rotation of the motor shaft 66 translates the fiber/lens unit along its track while imaging is performed in the forward direction. The motor unit 61 may also be located at the proximal end of the device with the rotational torque transferred to the distal end and the transverse displacement mechanism via a shaft or a torque cable encased in a rigid or flexible hollow housing.

FIG. 4b translates the fiber/lens unit with a piezoelectric cantilever 74. Such a cantilever 74 bends when a voltage is applied across the cantilever materials. The applied voltage attempts to polarize the material with fixed dipoles. To align the dipoles, the material bends in response to the applied field. With the fiber/lens unit fixed to the cantilever 74, bending results in a lateral translation of the unit. If the unit is rigidly affixed to the cantilever 74, the translation is not truly transversely linear, but actually represents an arc. However, the deviation from a linear translation is negligible with respect to the translatable distance. Displacements of 1–2 mm is typical for bimorph cantilever 74 with 300 V applied. Displacements can also be increased by extending the arm of the cantilever 74 with a rigid tube. Displacements are increased linearly with increasing arm lengths. Other electromagnetic actuator means are also possible.

As shown in FIG. 4g, the cantilever 78 does not have to be made of piezoelectric material. Rather, piezoelectric stacks may be used in conjunction with a metal or flexible material cantilever. The cantilever 78 would be flat to prevent twisting and thin in the axis of flexure to facilitate bending. By fixing one end of the cantilever 78 to the fixed points (housing) 76 and placing the piezoelectric stack 80 under the cantilever, small stack displacements can be mapped into large transverse displacements of the cantilever. Displacements can be increased by progressively locating the piezoelectric stack closer to the cantilever site of attachment.

Figure 4H:
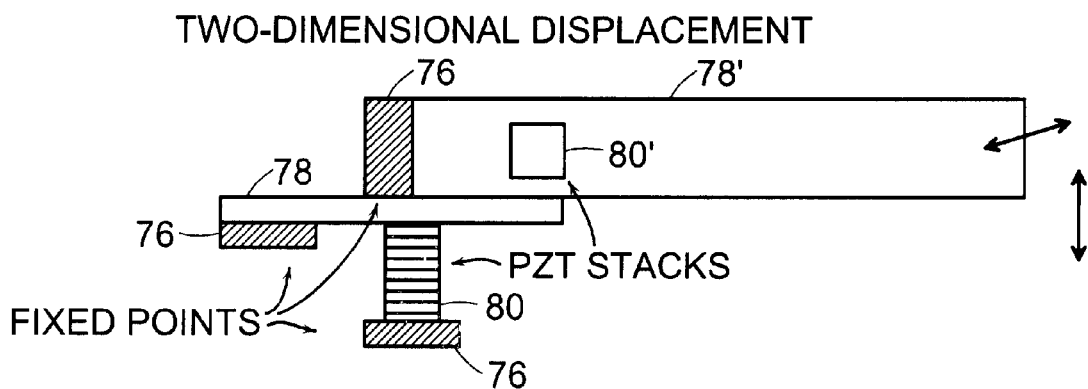
Figure 4I:
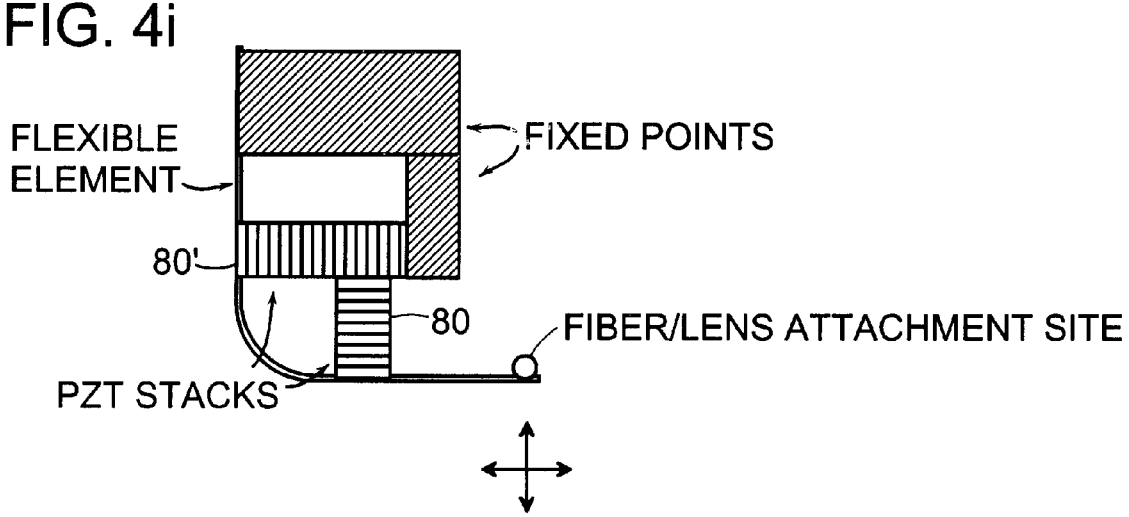

The use of a piezoelectric stack to displace a cantilever can be extended to two dimensions as shown in FIG. 4h. Using two PZTs, a second cantilever 78' is mounted on the first and oriented with its flexion axis perpendicular to the first and driven by another PCT 80'. Additionally, if the cantilevers (piezoelectric or otherwise) are small enough, they may be oriented transverse to the axis of the device as shown in FIG. 4i. In this FIG. 4i the horizontal PZT 80' deflects off fixed point 76 causing motion of the fiber/lens attachment horizontally and deflection of the vertical PZT flexes the fiber vertically. This design, also, permits two-dimension transverse scanning in the forward direction. Finally, the actuators used to move the cantilevers are not restricted to piezoelectrics, but may be magnetic, pneumatic, or other drives.

Referring to FIG. 4c, one or more movable wires or guides 90 are used to mechanically displace in a push/pull manner the fiber/lens unit in an arc about a pivot point 94. The movable wire 90 is housed within the cylindrical enclosure along with the single-mode optical fiber 58. The translation of the fiber/lens unit 63 is dependent on the point of attachment of the wire 90 with respect to the pivot point 94. If the wire 90 is attached close to the pivot point 94, then small movements of the wire 90 will result in large arc displacements of the fiber/lens unit 63. Such a design may suffer from bending of the cylindrical enclosure 50 if such a mechanism is employed in a flexible enclosure.

FIG. 4d utilizes pneumatic principles to displace the fiber/lens unit 63 within the enclosure. Here, two or more air/fluid-filled bags 96, 96' are used in a complementary fashion to hold the fiber/lens unit 63 and displace it in a transverse direction. By inflating one bag 96 while simultaneously removing air/fluid from the opposite-located bag 96', linear translation will result. If more than two bags 96, 96' are used, that transverse displacement can approach that of an arbitrary scan pattern. Typically, however, due to the necessary air/fluid conduits (not shown) needed to run between the bags 96, 96' and an external reservoir, the number of bags 96, 96' will probably be limited to two or four. Four bags will permit transverse scanning in two, orthogonal directions.

Within the outer cylindrical enclosure 50, a rigid tube 100 can house the fiber 58 and lens 63 as shown in FIG. 4e. In this method, a translation track 104 is located near the distal end of the enclosure. This track is offset at an angle with respect to the axis of the cylindrical enclosure 50. When tension is applied at the proximal end 102 of the rigid tube 100, this tension causes the fiber/lens unit 63 to be translated at an angle, as well as in the transverse direction. Such a scan method results in an angled image plane. Imaging however, is still largely performed in the forward-direction. An angled image plane is equivalent to using one of the previous methods where the enclosure is tilted at an angle with respect to the sample. This angled image plane can be compensated for by internally altering the angle of the track and the direction which the rigid tube projects through the cylindrical enclosure. In order to facilitate the restoration of the fiber/lens unit 63 a small spring mechanism can be added between the wall of the unit and the fiber/lens unit 63.

FIG. 4f illustrates how electrostatic/magnetic principles can be applied to laterally translating the fiber/lens unit. The lens 63 is coated with a metalized material which can be attracted to appropriately charged/magnetized contacts. For instance, in the distal end of the enclosure, electrostatically charged plates 108 can be used to translate the fiber/lens unit 63. By altering the voltage applied to the electrostatic plates or by moving an electrostatically charged region, the metalized lens 63 will be attracted to this region and hence, be displaced in the lateral direction. In one embodiment the metalized fiber/lens 63 unit is attached to a flexural pivot (not shown). Very high lateral velocities can be achieved by rapidly alternating the charges on the plates and by translating the fiber/lens 63 unit at a natural or modified resonant frequency. By transversely displacing the fiber/lens 63 at its resonant frequency, displacement becomes more sinusoidal rather than linear. However, data acquisition rates and image display can be compensated for this non-linear translation.

A second concept which involves the movement of the fiber/lens unit is illustrated in FIGS. 5a, b. The fiber/lens unit 63 is fixed within the forward-imaging device, but the entire device is translated in the transverse direction to obtain the cross-sectional image. While the device is stationary, single axial scans of the same location are repeatedly acquired. When the device is translated, this motion is sensed by a sensing mechanism which instructs the control computer at which position to place the axial scan within the image. If multiple axial scans are acquired at the same location, these scans can be averaged or summed as determined by the user. Two sensing mechanisms are shown in FIGS. 5a, b. The sensing mechanism in FIG. 5a utilizes a secondary imaging fiber bundle 120 an optical imaging processing mechanism at distal end 124 which image processes the acquired data to determine relative motion, direction, and velocity. This information is used to assemble the corresponding axial scans to form the OCT image. This design does not require physical contact with the sample or specimen. The sensing mechanism shown in FIG. 5b is a position sensing rolling mechanism 125 analogous to the computer mouse. The device is physically placed on the specimen or sample to be imaged and translated across the surface. Motion, direction, and velocity are recorded by the position-sensitive rollers 124 and is used to assemble acquired axial scans.

2) Methods to Move the Optical Fiber with a Fixed Lens

Similar methods of translation can be performed by moving the optical fiber while maintaining a fixed position for the lens. FIGS. 6a–f illustrate these principles. The fundamental displacement mechanisms were described above and in FIG. 4. With this method, a flat or angle-cleaved optical fiber 58 is located on the translation mechanism. The fiber 58 is then translated on one side (in the image plane) of the lens 62. A translation of the focal region on the opposite side of the lens (in the object plane) results. Magnification or demagnification of the fiber face and the transverse displacement occurs with this design based on the separations between the fiber face, specimen, and the lens. This magnification will vary the spot size (transverse resolution) and the confocal parameter (depth of focus) of the device which differs from the fixed parameters described in the previous methods. With this concept, the focal region will not lie in a single image plane, but will sweep out an arc. As the fiber is translated to the edge of the lens, the focal spot size will change. A lens system can be manufactured which reduces the aberrations which result from this method of imaging.

3) Methods to Move the Lens with a Fixed Optical Fiber

In FIGS. 7a–7f, the similar methods of translation are used to move the lens 62 in front of a fixed flat or angle-cleaved fiber 58. The fundamental displacement mechanisms were described above and in FIG. 4. As explained previously, translation of the lens 62 or fiber 58 will result in the same difficulties such as aberrations at the beginning/end of translation and an arced, non-flat imaging plane but these can be overcome with known optical design techniques.

4) Methods for Deflecting the Forward-Directed Beam

Figure 8A:
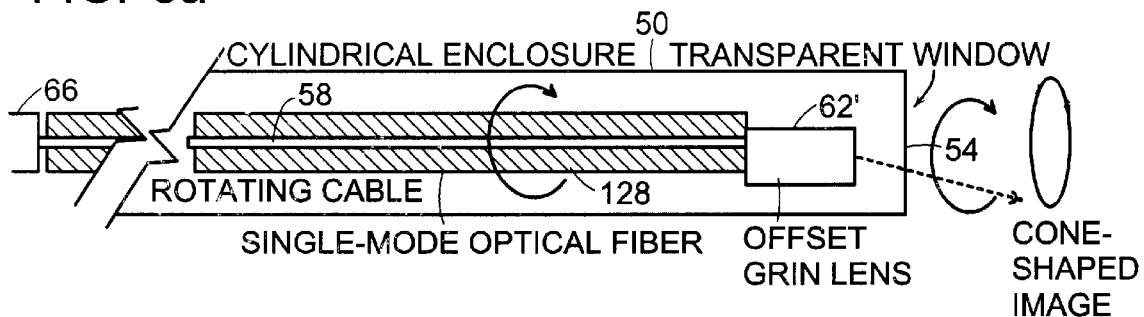
FIGS. 8a–d are crossectional views of general methods for deflecting imaging beam in a forward direction.

Four methods are shown in FIGS. 8a–d for deflecting or re-directing the optical beam in the forward-direction for the purpose of imaging. FIG. 8a utilizes a rotating cable 128 within the cylindrical enclosure 50. The optical fiber 58 is contained within and is protected by the cable 128. At the distal end, an offset GRIN lens 62 (or other type of lens) is metered with respect to the optical fiber 58. Because the lens axis is offset with respect to the optical fiber 58, the emitted beam is not focused on axis with the fiber. Instead, the focus occurs at an angle which is dependent on the degree of offset between the GRIN 62 and fiber 58. Within the outer cylindrical enclosure 50, the cable/fiber/GRIN lens 128, 58, 62 is rotated by a drive unit 60. Drive unit 60 may be implemented in a number of ways including mechanical linkage from a motor to a rotating torgue cable. As the unit rotates, a conical profile is traced out. Images acquired with this method represent a cone sample which can still be displayed in a 2-D manner similar to ultrasound. This forward-directed scanning method has the advantage that the device can be incorporated into flexible instruments or catheters. Alternatively, the lens can be mounted on-axis with the fiber and the fiber/lens combination can be slightly tilted with respect to the axis of rotation.

Figure 8B:
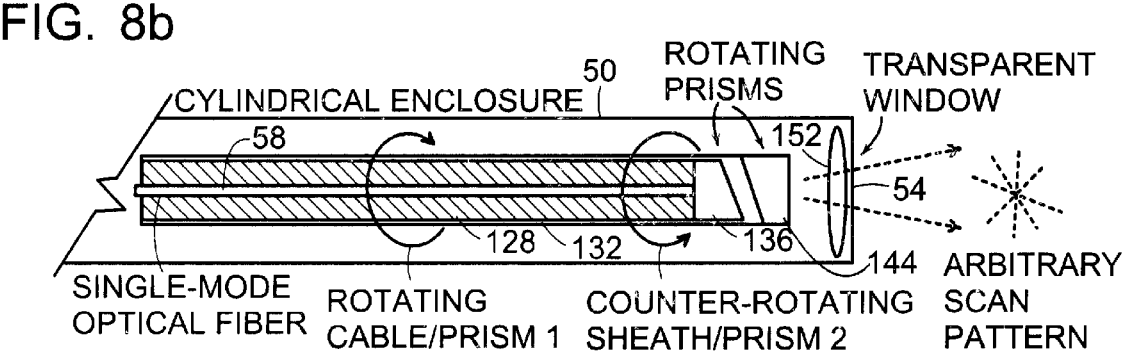

A second method, illustrated in FIG. 8b, describes a technique for arbitrary scan patterns in the forward direction. This method also utilizes an internal cable 128 and an additional internal sheath 132 which rotate in counter-directions with respect to one another. The outer cylindrical enclosure 50 remains fixed. The most inner element is a metal cable 128 which houses and protects an optical fiber 58 within its core. The distal end of this includes a circular prism 136 (trapezoidal in cross section). External to this cable/fiber/prism 128, 58, 136 is a counter-rotating sheath 132 that has a second prism 144 attached at the distal end. By rotating these elements in opposite directions and by varying their phases with respect to one another, arbitrary scan patterns can be produced. The emitted beam is focused by a lens 152 prior to exiting the cylindrical enclosure 50. Note that an alternate embodiment (not shown) is to have one drive cable and a small gearing mechanism for counter driving the second prism. Finally note that if the two prisms are driven in the same direction (as opposed to counter rotating) and their relative phase can be adjusted then a cone-shaped image pattern can be achieved similar to 8a) with a variable cone angle. Alternatively, the lens can be rigidly mounted to the fiber prior to transmission through the prisms or two lens could be used (not shown), before (to collimate) and after (to focus) the rotating prisms. This approach can yield better stability of the optical system.

Figure 8C:
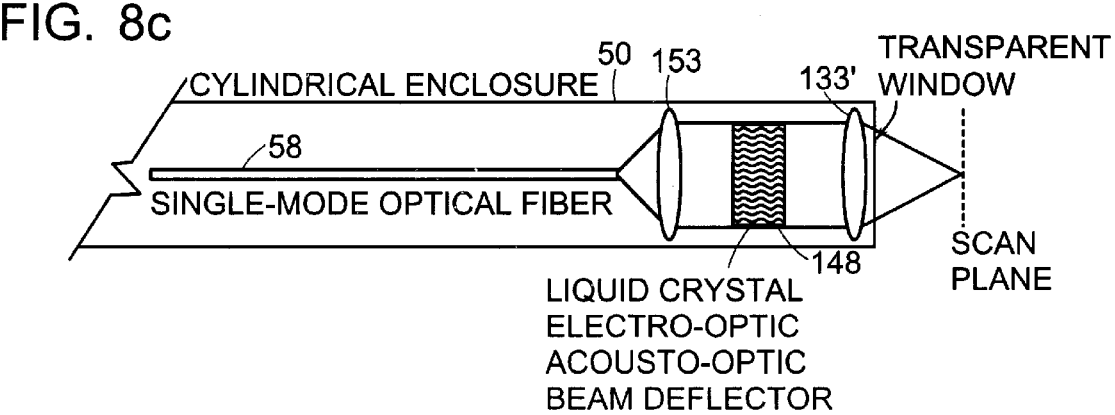
Figure 8D:
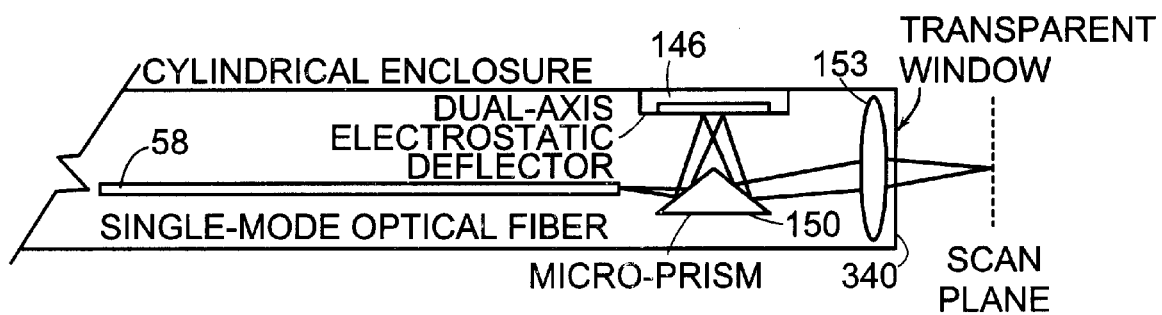

FIG. 8c illustrates the use of a beam-deflector element 148 placed between a pair of lenses 153, 153'. The proximal lens 153 directs the light from the fiber 58 through the beam-deflector element 148. After passing through the beam-deflector 148, a second lens 153' is used to focus the light into the image plane. The beam-deflecting element can consist of, but is not limited to, liquid-crystal, electro-optic, or acousto-optic modulators. Note that alternative embodiments can use different lens arrangements depending on the aperture size and type of beam-deflector used.

The design illustrated in FIG. 6d utilizes a two-dimensional miniaturized deflector 146 such as an electrostatic deflector that can be microfabricated on semiconductor or other substrates such as silicon mem's. The imaging beam exiting the fiber is reflected by a prism/mirror 150 on to the electrostatic deflector where it is redirected, reflected off of the other side of the prism, and then focused in the forward direction by a lens 153. This design has the potential for arbitrary scan patterns generated at high speeds. Other types of deflectors such as electromagnetic, piezoelectric, etc., can be use as well in this configuration.

Finally, beam deflection can be accomplished by translating or displacing a mirror in front of the imaging beam using any of the actuators (PZT, magnetic, electrostatic, pneumatic) described in FIGS. 4–8. All of the described forward-scanning mechanisms can be generalized to side-directed linear scanning or side-directed radial scanning simply by the addition of a fold prism or fold mirror (not shown) to direct the imaging beam at arbitrary angles from the axis of the device. Side-directed linear scanning can be performed by using a fold mirror and an electrostatic, mechanical, or other similar mechanism to rapidly move the device along the central axis of the device. Side-directed radial scanning can be performed by using a fold mirror and rotating the device about the central axis using a electrical motor or magnetic mechanism.

All of the designs described in FIGS. 4–8, except for the designs in FIG. 8a (and some operational modes of 8b), produce a linear scan in the forward direction. Multiple linear scans can be performed at other angles by incorporating these general methods into a second cylindrical unit. With this modification, the inner cylindrical unit may be rotated about the central axis while the outer cylindrical unit is held stationary. This permits linear scanning at arbitrary angles in order for the user to choose which angle is most suitable for a particular application. In addition, by precisely controlling the angle of rotation of the device, a series of linear scans can be acquired and later assembled to produce a three-dimensional reconstruction of the forward-imaged sample. The acquired linear scans would form a spoke-like pattern about a center point.

Although most of the methods described above only scan in one linear dimension, each can be modified by duplicating transverse displacement components to scan in two-dimensions (x/y). By controlling the scan pattern along each axis, arbitrary scan patterns can be achieved and three-dimensional data sets can be acquired.

Three key terms need to be introduced for future descriptions of imaging beam characteristics and are illustrated in FIG. 9. The first is called FOCUS POSITIONING (FIG. 9A) which is the axial displacement/adjustment of the beam focus without changing any of the beam parameters (focal spot size diameter, depth-of-focus, working distance). The second is FOCUS VARYING (FIG. 9b) which implies changes in spot size, depth of focus, and working distance, and finally, FOCUS TRACKING (FIG. 9c) which refers more specifically to the OCT imaging engine adjustments to permit the overlap of the coherence gating region within the imaging beam depth-of-focus.

For all the methods described above, the output optical beam characteristics were fixed and independent of the transverse displacement. A fixed focal spot and position was transversely translated through the sample or specimen. For each of these methods, a means of varying the separation between the fiber and the lens can be implemented which will serve to vary the imaging beam characteristics and hence, perform focus varying. This could be accomplished by using a cylindrical piezoelectric stack, mechanical displacements with small motorized positioners, inflatable balloons, or pneumatic/hydraulic devices. By varying the separation between the fiber and the lens, the beam spot size could be increased or decreased (hence the transverse resolution varied), as well as the confocal parameter or depth-of-field. Such implementation permits rapid imaging at lower resolutions and larger depths-of-field and later high resolution imaging at selected regions of interest.

Often it is desirable to maintain the beam characteristics (spot size, depth-of-field, working distance) while performing focus positioning. Accomplishing this is somewhat dependent on the optical configuration of the device. One method involves translating the entire apparatus in the z (depth) direction either toward or away from the specimen. This repositions the focus appropriately. Translation can be performed manually with a micrometer adjustment or via a electrical/mechanical drive mechanism. When a telescope configuration is used with a collimated beam between two lenses (156, 156') (for example as shown in FIG. 9a), the separation between the two lenses 156, 156' can be varied without affecting the beam characteristics. Such a telescopic arrangement is important for several implementations including endoscopes where it is desirable to be able to automatically adjust the focus positioning to compensate for varying distances to the luminal wall.

Both focus positioning and focus varying are likely to be used in combination. For instance, large regions of a specimen or sample may be scanned at lower resolutions and with a larger depth-of-field. Focus varying can be implemented to reduce the spot size (increase resolution) and hence, reduce the depth-of-field. At this point, focus positioning would be necessary to move the focus to a precise location in the specimen at a certain distance from the end of the imaging device.

Focus varying is illustrated in FIG. 9b. Here lens 156 is translated and changes spot size, depth field, and working distances. Several alternative embodiments are possible such as zoom lens configurations.

At high lateral resolutions (such as those required to achieve cellular or sub-cellular resolutions) a high numerical aperture objective or lens and a small beam spot diameter are required to achieve sufficient lateral resolution. This small spot diameter has a correspondingly small depth-of-field or depth-of-focus as is known in the art. Thus, focus tracking must also be employed to ensure the data is acquired and coherence gated from the short depth-of-focus of the lens. FIG. 9C illustrates an example of focus tracking. $\Delta L$ is the displacement of the focusing lens 156', $\Delta F$ is the displacement of the focusing spot within the specimen 164, and $\Delta R$ is the displacement of the optical path length of the reference mirror 160 (assumed to be in air) required to maintain the optical path length to the focusing spot within the specimen 164 equal to the optical path length to the reference reflection. There are several important factors to consider when designing focus tracking systems. One example is that the relationship between $\Delta L$, $\Delta F$, and $\Delta R$ can be a complicated non-linear equation depending on the index of refraction profile within the specimen 164 and the numerical aperture of the lens 156'. This equation can be solved and programmed into the computer controller subsystem to achieve very high lateral and longitudinal imaging with the specimen 164. For example, if the index profile of the sample is approximately uniform and given by $n_{sample}$, and small angle approximations to the focused light can be made (e.g. sin $\theta \approx \theta$) then $\Delta F \approx n_{sample} \Delta L$, and $\Delta R \approx (n_{sample})^2 \Delta L$ for the moving lens 156' configuration shown in FIG. 9c. Alternatively, if the sample 164 is moved toward a fixed lens 156' (as might be implemented in a microscope stage described herein, then $\Delta R \approx ((n_{sample})^2 - 1) \Delta L$. This equation also describes the situation where the reference mirror base is attached to the moving focusing lens and adjusted relative to the focusing lens base. The tolerance that the focus tracking must achieve over the scanning range within the sample is approximately equal to the depth-of-focus of the focusing lens. In many instances this simple approximation is sufficient to achieve the required result. In situations where very high numerical aperture lenses are used the more exact expressions or algorithms must be programmed into the computer controller subsystem to maintain focus tracking.

Another approach to focus tracking, for specimens that can be approximated as having a uniform refractive index, is to use an index matching liquid between the focusing lens 156' and the sample 164. Thus as the focusing lens 156' is moved toward the sample 164 or the sample 164 is moved toward the focusing lens 156', the liquid volume will adjust to maintain a constant focal point relative to the pupil of the focusing lens 156'. This makes for a particularly simple algorithm for moving the reference mirror 160 location $\Delta R$. If the lens 156' is moved then the mirror 160 is moved 1:1. If the sample 164 is moved toward the lens 156' then the reference mirror 160 can remain stationary.

In focus tracking systems, it may also be necessary to implement dynamic dispersion compensation to adjust for the sample/specimen-induced dispersion. This will permit the high axial resolution provided by the broad bandwidth source to be effective even at significant depths within highly dispersive material or tissue.

Another approach for focus tracking that can easily accommodate more complex sample index profiles is to perform transverse priority scanning and adjust the reference mirror location to maximize image quality. This works well if the optical path length variation to the focus within the sample is less than the depth-of-focus. The adjustment can be manual in response to a human operator visualizing the real-time OCT image or it can be automated by maximizing the detected signal power averaged across the transverse scan or by maximizing other detected parameters.

In some applications of this invention such as imaging thick specimens (e.g. histological sections) under a high NA microscope, it may be possible to manually or in an automated way derive the relationship between $\Delta L$, $\Delta F$, and $\Delta R$. For example, one algorithmn is to block the reference optical signal and use the OCT system in a direct detection confocal microscope. With the sample placed on a highly reflecting substrate (e.g. a mirror), the operator first locates the specimen's front surface reflection by bringing the sample into the field-of-view and searching for the first maximum in detected signal power. The specimen is then scanned manually or in an automated way to profile the back scattered signal power in search for the weaker reflection off of the more distant mirror. The two positions for the focusing lens (or samples translation stage) are recorded. The focusing lens is then placed at the front surface reflection. The OCT system is placed into its interferometric mode and the reference reflection optical path length is scanned and the position of maximum interferometric signal is recorded. This locates the focusing lens and reference arm path length to the front surface reflection. The focusing lens is then placed at the back surface (mirror) reflection and the OCT reference reflection optical path length is again scanned and the position of maximum interferometric signal is again recorded. This locates the focusing lens and reference arm path length to the back surface reflection. An approximate (linearized) relationship between $\Delta R$ and $\Delta L$ can be found by the difference in the reference mirror locations divided by the difference in the focusing lens locations. This linearized approximation will be sufficient for many specimens of interest. In situations where the back surface reflection cannot be seen or located in direct detection mode this algorithm can be extended by searching for the samples back surface reflection (that is the mirror substrate reflection) in an iterative fashion in the coherent detection mode. The lens location is stepped and the reference arm is swept and this process is repeated until the mirror location is identified. Knowing the samples approximate index and thickness can greatly reduce the search time and increase the reliability of finding the back surface location. Several other algorithms, that are extensions of these basis concepts, for manual or automated calibration of the focus tracking algorithm can also be used.

There are many equivalent embodiments to achieve focus tracking that are variations on this basic theme: that to maintain high lateral resolution within a sample requires a high NA lens which implies a short depth-of-focus, which necessitates the need to adjust the reference mirror location as the focusing lens is moved to image different depths within a specimen.

While the concept of focus tracking is important for many of the applications to be described in the following sections it is particularly relevant to the surgical and high NA microscope embodiments described below.

Hand-Held Forward-Scanning Probe

Figure 10:
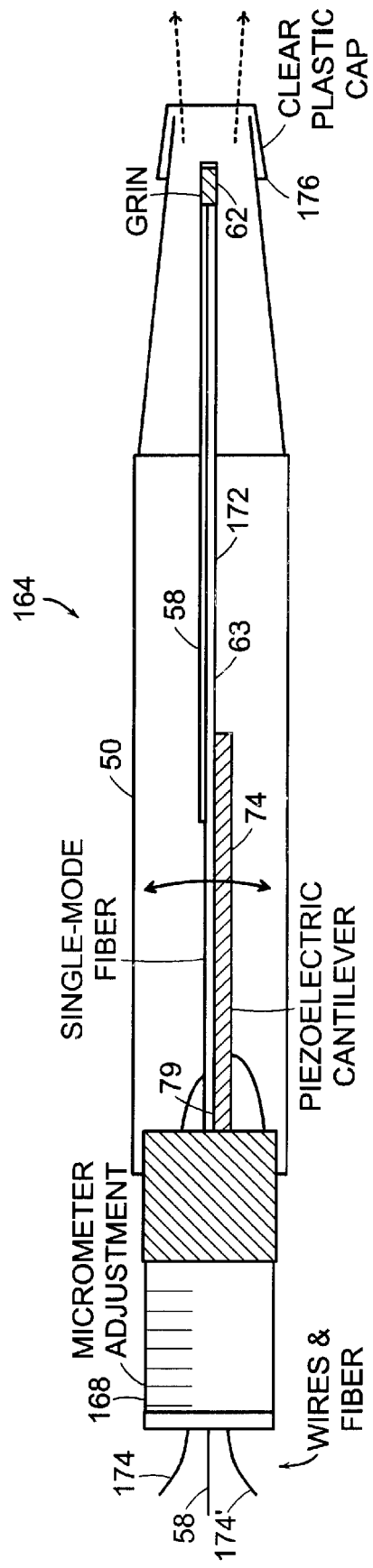
FIG. 10 is a longitudinal sectional view of an embodiment of a forward-scanning hand-held probe.

As shown in FIG. 10, the general methods of forward-directed scanning can be implemented in a hand-held device 164 that performs forward-directed optical imaging of biological specimens or material samples. The ability to have forward-directed imaging in an instrument having a size that can be conveniently hand held no larger than a pen offers the advantages of data and image acquisition at locations remote to the OCT computer control and imaging engines. This is largely due to the fiber-optic and micro-optic technology utilized by this invention. Contained within the hand-held probe 164 is all the translation mechanics, microoptics, and fiber-optic interconnect necessary for transverse displacement and forward-directed scanning.

A hand-held probe has applications in, but is not confined to, the medical field, materials investigation, and the military. The medical field can utilize its compact profile in the open-field surgical setting to image sub-surface tissue morphology prior to disrupting, incising, or resecting the tissue. A forward-directed imaging probe offers the advantage that no portion of the instrument has to come in contact with the tissue prior to obtaining imaging data. This is in contrast to devices that image in the radial or transverse direction. Here, the catheter or device must be inserted into the tissue prior to obtaining an image. Within the open-surgical field, space is at a premium. Therefore, an additional instrument must be compact and easily manipulated by the surgeon. For medical applications not involving open-field surgery, the hand-held probe can be used to access any external region of the human body, or any external orifice, without have the patient be placed in uncomfortable positions. For OCT imaging to occur, the fiber path lengths between the sample and reference arms must be matched or otherwise compensated for dispersion balancing. Because long fiber lengths can be contained within small volumes, the sample arm of the OCT imaging engine, to which is connected the hand-held probe, can be of any reasonable length. Therefore, a hand-held probe can be used to image any external region of the human body while the patient stands, sits, or lies in a bed. In addition, because of the use of micro-optics, the distal portion of the device can be made very small and able to be inserted short distances into body orifices and canals such as the external ear canal, nasal passage, or mouth.

The compact nature of the OCT imaging engine coupled with the small hand-held probe permits the entire system to be portable for materials investigation around a factory or at remote job sites. The concept of a pen-like device requires little training in its use and alignment as this style has been readily implemented in technologies such as pen-style bar code readers. Finally, advantages such as compact profile and portability are attractive options for military use of medical imaging at forward battlefield locations for the in-field assessment and potential treatment of injury.

One implementation of a forward-scanning hand-held probe is shown in FIG. 10. This design utilizes a piezoelectric cantilever 74 to displace the fiber/lens unit 63 in an arc, however, the design is not limited to the use of cantilevers and may incorporate any of the general methods described herein. The overall dimensions of this device are no larger than a standard ink pen, making the instrument fit comfortably in the operator's hand. The cylindrical enclosure 50 is made of a protective and insulating plastic that shields the cantilever 74, fiber 58, and lens 62 from contaminants and liquids. The use of an insulating plastic material also prevents injury to the user as a result of shorting between the voltage applied to the piezoelectric cantilever 74 and the user's hand.

The piezoelectric bimorph material is centered within the cylindrical enclosure 50 probe barrel to allow bending displacement during scanning. The proximal end 79 of the cantilever 74 is fixed to a micrometer 168 to vary the location of the imaging beam focus with respect to the distal end of the probe and with respect to the tissue specimen or sample. To increase the lateral displacement of the fiber/lens unit 63, a tube 172 is fixed at the end of the cantilever 74. This increases the distance of the fiber/lens unit 63 from the bending cantilever 74 and linearly increases the displacement. The tube also protects the small lens 62 and single-mode fiber 58. The lens 62 used in this design is a GRIN (GRadient INdex) lens which allows effective focusing of the light emitted from the fiber while maintaining a small outer diameter. The small cylindrical GRIN lens 62 easily fits within the cylindrical tube 172. To reduce the degree of optical back-reflections which occur from the normal-incident faces of the fiber and GRIN, the fiber can be angle-cleaved and the GRIN can be angle-polished. The fiber is attached to the GRIN lens using ultraviolet cured optical cement at a pre-determined distance. This distance determines the focusing properties of the emitted light such as working distance, spot size, and confocal parameter. Alternate lens embodiments include using fiber up-tapers with an integrated polished lens or other lenses that are known in the art.

The distal end of the cylindrical enclosure has a clear plastic cap 176 that is removable after contact with biological tissue. This cap serves four major purposes: 1) to allow the probe to be placed in contact with the tissue specimen or material sample thereby fixing the image plane at a fixed distance within the specimen, 2) on contact, motion artifacts are minimized because the probe can move with the tissue or sample, 3) the clear plastic permits the user to visualize where scanning is occurring when a visible aiming beam is coincident with the OCT imaging beam, and 4) the replaceable cap maintains cleanliness and avoids transmission of bacteria or viruses between patients.

The only interconnections required with the use of this design include the single optical fiber and two wires 174, 174' necessary to drive the piezoelectric cantilever. Typically, voltages of several hundred volts are necessary to displace the cantilever 1 mm. The use of the extension arm 172 increases the displacement to 2 mm. Larger displacements can be achieved by increasing the applied voltage (while remaining below the damage threshold of the material) and increasing the length of the extension arm.

Figure 11:
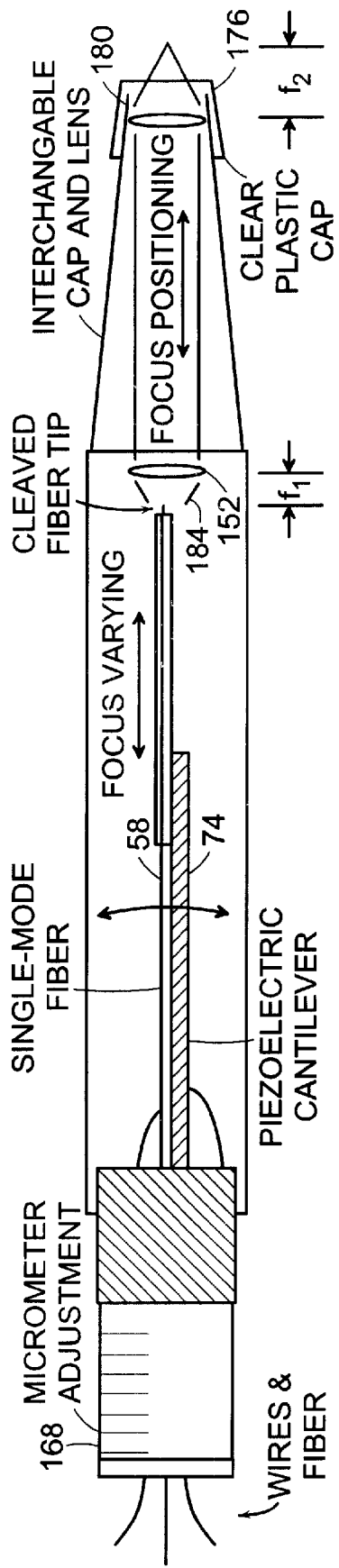
FIG. 11 is a longitudinal sectional view of an embodiment of a forward-scanning hand-held probe with interchangeable magnifications.

A second hand-held probe design is illustrated in FIG. 11. This design utilizes similar cantilever-displacement principles, but offers an interchangeable lens 180 to vary the magnification of the device. Instead of affixing a GRIN lens to the fiber, the fiber 58 alone is attached to the cantilever 74 and displaced at the focus of a fixed lens 152. This design, however, is not limited to the use of piezoelectric cantilevers, but may utilize any method which produces suitable x and y displacement of the fiber in the focal plane. The light emitted from the cleaved fiber 184 is collimated by lens 152 and directed toward a second, more distal lens 180 where it is focused at a forward imaging plane, within the sample to be imaged. The pair of lenses 152, 180 represents a telescope design where magnification is determined by the ratio of the focal lengths of the two lens: magnification=$f_2/f_1$. Other imaging systems may also be used. The distal cap 176 and lens 180 are interchangeable by replacing unit 190 or 176 thereby permitting various magnifications and scan lengths to be obtained. The interchangeable cap 176 and lens 180 are disposable and serves to protect the remainder of the probe from liquids and contaminants. This design has different optical properties than the scanning fiber/lens design in FIG. 10. The previous design has resolution and depth of field determined by a fixed fiber/lens separation with transverse translation determined directly by displacement. The design in FIG. 11, however, has resolution and depth of field determined by the fiber mode size and the numerical aperture of the lenses. Both the mode size exiting the fiber and the transverse displacement are scaled by the magnification of the two-lens optical system. The micrometer 168 represented in FIG. 11 is only one means to adjust the separation between the fiber 58 and the proximal lens 152 and other techniques can be incorporated. Because of the magnification factor associated with the two lenses, the displacement of the fiber tip via the micrometer or other technique does not result in a 1:1 mapping of the displacement of the focus within the sample.

Figure 12:
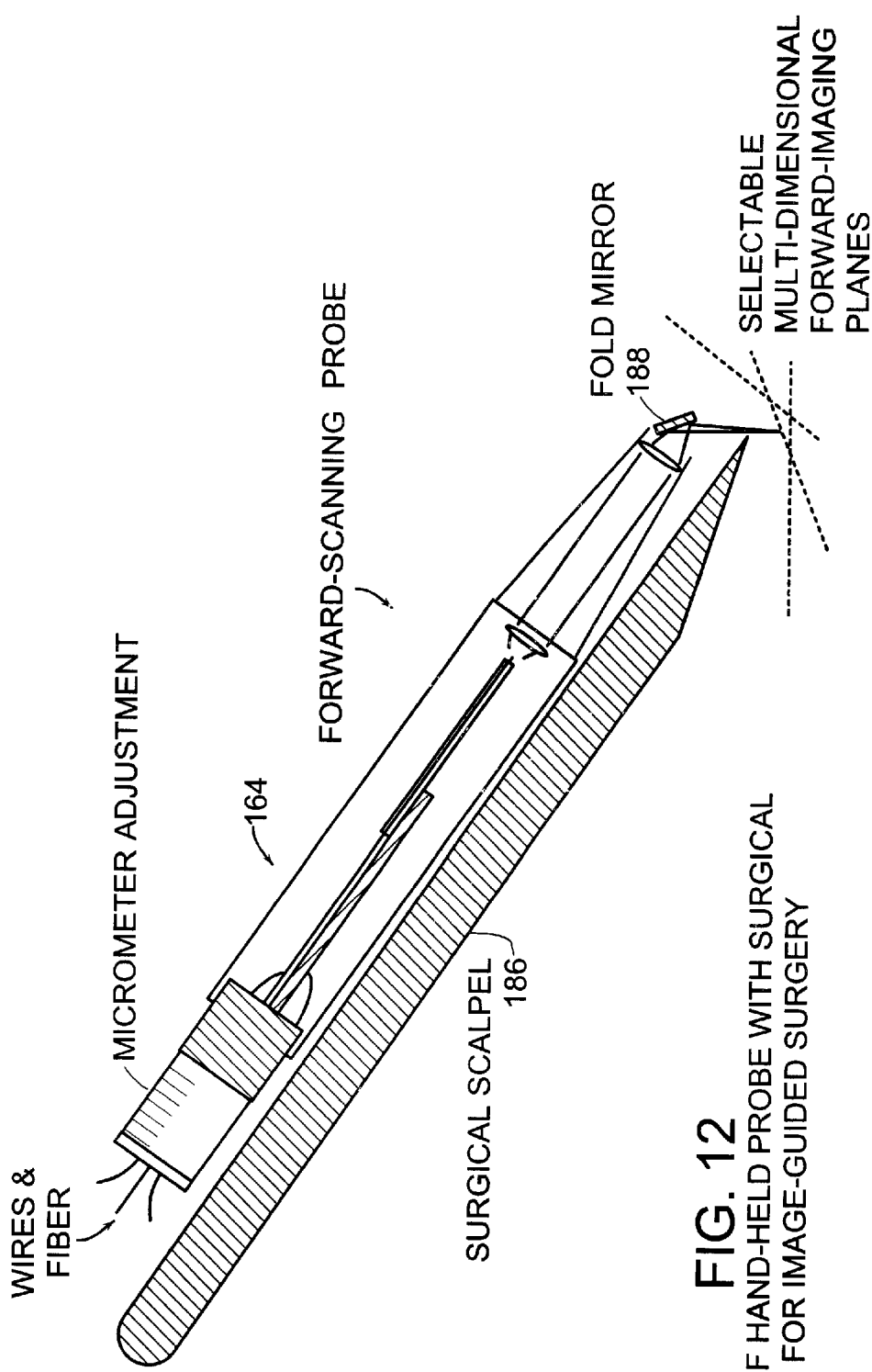
FIG. 12 is a longitudinal sectional view of an embodiment of the integration of a hand-held probe with a surgical scalpel for image-guided surgery.

The use of the hand-held probe 164 in the surgical setting offers simple integration with existing surgical devices such as a scalpel 186 as is shown in FIG. 12. Because the forward-directed imaging probe 164 is comparable in size to a surgical scalpel 186, the two can be attached in a manner to permit forward-directed imaging to be performed prior to incision with the scalpel and at arbitrary angles with respect to the surgical blade. Two-dimensional imaging can be integrated or multiple image planes can be imaged simultaneously by interweaving the scan pattern or by using two translation modules. These two or more planes can be simultaneously displayed. Images obtained with the imaging probe will permit the surgeon to view the sub-structure and avoid sensitive structures such as nerves or vessels or assist in determining locations of tumors and identifying tumor margins prior to resection. In addition, OCT may be configured to perform laser Doppler velocimetry of the tissue prior to incision. Images can be generated which detect and display any sub-surface movement, such as flowing blood, which would indicate the presence of an artery or vein. Several design options exist which can direct the light more closely to the tip of the scalpel. For instance a small fold mirror 188 or appropriate metering between the scalpel 186 and probe 164 could angle the beam more closely to the tip of the scalpel 186. Also the scalpel blade could be rotated 90° with respect to the axis of imaging, and the probe could be located below the scalpel so that the cutting axis is imaged prior to incision. Finally, one or more optical fibers can be positioned within the scalpel blade itself (for example in a blade made of optically translucent material or in a more conventional metal blade with appropriate imaging ports) (not shown) with the tip of the fiber located at the tip or along the edge of the scalpel blade. With high densities of fibers, imaging can be performed whereas with lower numbers of fibers, isolated depth information can be acquired. Single axial scans can be performed which can provide depth ranging information of the tissue prior to scalpel blade insertion. If the fibers are in near contact with the specimen or sample, the lenses to focus the light may be low power or may not be needed at all. Such fibers may be located within a blunt-tipped probe (see FIG. 25*a*) which is commonly used during surgical procedures to move tissue and clear regions of interest. The blunt probe is typically held in the opposite hand as the scalpel and frequently used to point to and identify tissue. The coincident visible aiming beam and the use of sub-surface imaging with the probe will extend its application in the surgical environment. Alternatively, an entire micro-scanning device can be incorporated onto the end of the scalpel which scans the beam in an angular pattern along the incision plane. In this design as well as all others, the use of a coincident visible aiming beam permits the user to visualize the location of the infrared or invisible imaging beam. This feature allows precise placement and alignment of the imaging beam on the sample or specimen.

Figure 13:
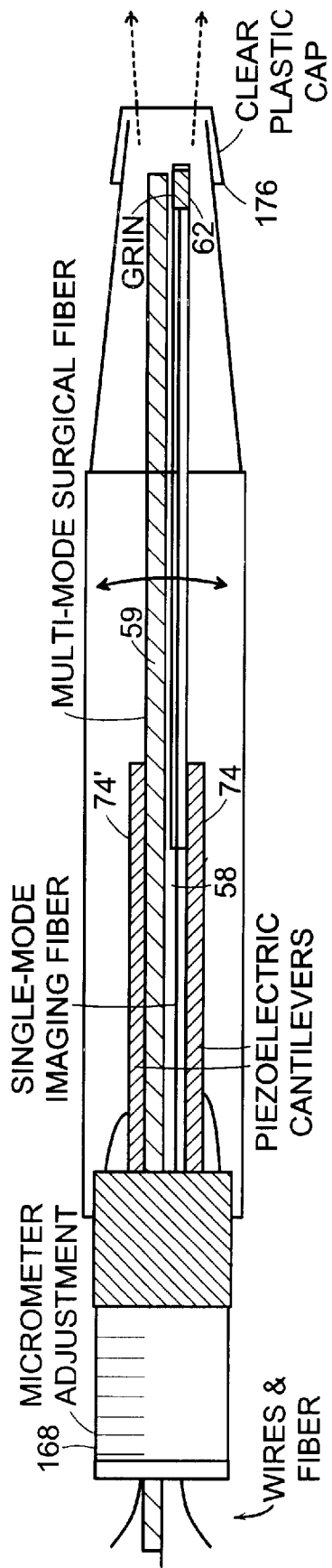
FIG. 13 is a longitudinal sectional view of an embodiment of a forward-scanning hand-held imaging/laser surgical probe.

Alternatively, high power continuous wave lasers or high energy pulsed lasers can be integrated with the OCT imaging system to replace the surgeons scalpel. These concepts have been demonstrated in the past as workable means of thermally incising, coagulating, or mechanically disrupting biological tissues. High power or high energy laser light can effectively be delivered with single-mode or multi-mode optical fibers. FIG. 13 illustrates the concept of integrating both a single-mode optical fiber 58 for OCT imaging with a single- or multi-mode fiber 59 for tissue incision or disruption. Each fiber 58, 59 could be translated with a piezoelectric cantilever 74, 74' either synchronized or independently. Alternatively, each of the fibers 58, 59 could be attached to the same piezoelectric cantilever 74, 74' or the surgical laser fiber 59 could remain stationary and the OCT system would scan through and about the point of surgical incision. Both the OCT imaging beam and the high power/energy laser radiation may be propagated down the same optical fiber permitting precise registration between OCT image and location of laser surgical procedures. This design will enable a single, integrated hand-held device which utilizes OCT imaging as a guide for laser surgery. This configuration also permits the acquisition of images prior to, during, and immediately following the delivery of the laser power/energy to immediately confirm the location and extent of the damage. If the high power laser could be delivered using the same single mode fiber used for OCT, then wavelength selective beam splitters/couplers (not shown) or fast optical switches (not shown) could be used to combine/separate the two light sources. The fine control of the laser could be controlled from the optical image by the therapeutic interface described in reference to FIG. 3.

The designs discussed and shown for the hand-held probe (FIGS. 10–13) all utilized the general forward-scanning method of a piezoelectric cantilever. As shown in FIGS. 4–8, other methods are possible which permit the forward-directed scanning in a compact, portable, and potentially remote hand-held instrument for optical imaging. A small pair of orthogonal galvanometers (not shown) can also be incorporated at the proximal end of the hand-held probe to direct the imaging beam off of rotating mirrors. This design will permit rapid two- and three-dimensional scanning as well. In addition, the internal scanning mechanism can be configured to rotate about the axis of the instrument. This would permit linear scanning at arbitrary angles. Multiple axes can be incorporated to allow two- and three-dimensional scanning. By varying the fiber/lens separation either manually with a micrometer 168 or dynamically with a PZT, motor, and a feedback system, focus varying may be performed. For the design shown in FIG. 11, displacement of the second, distal lens 180 effectively can allow focus positioning without affecting the beam parameters. It is possible to construct a highly flexible device with variable beam parameters and focal positions.

Rigid Endoscope/Laparoscope

Figure 14:
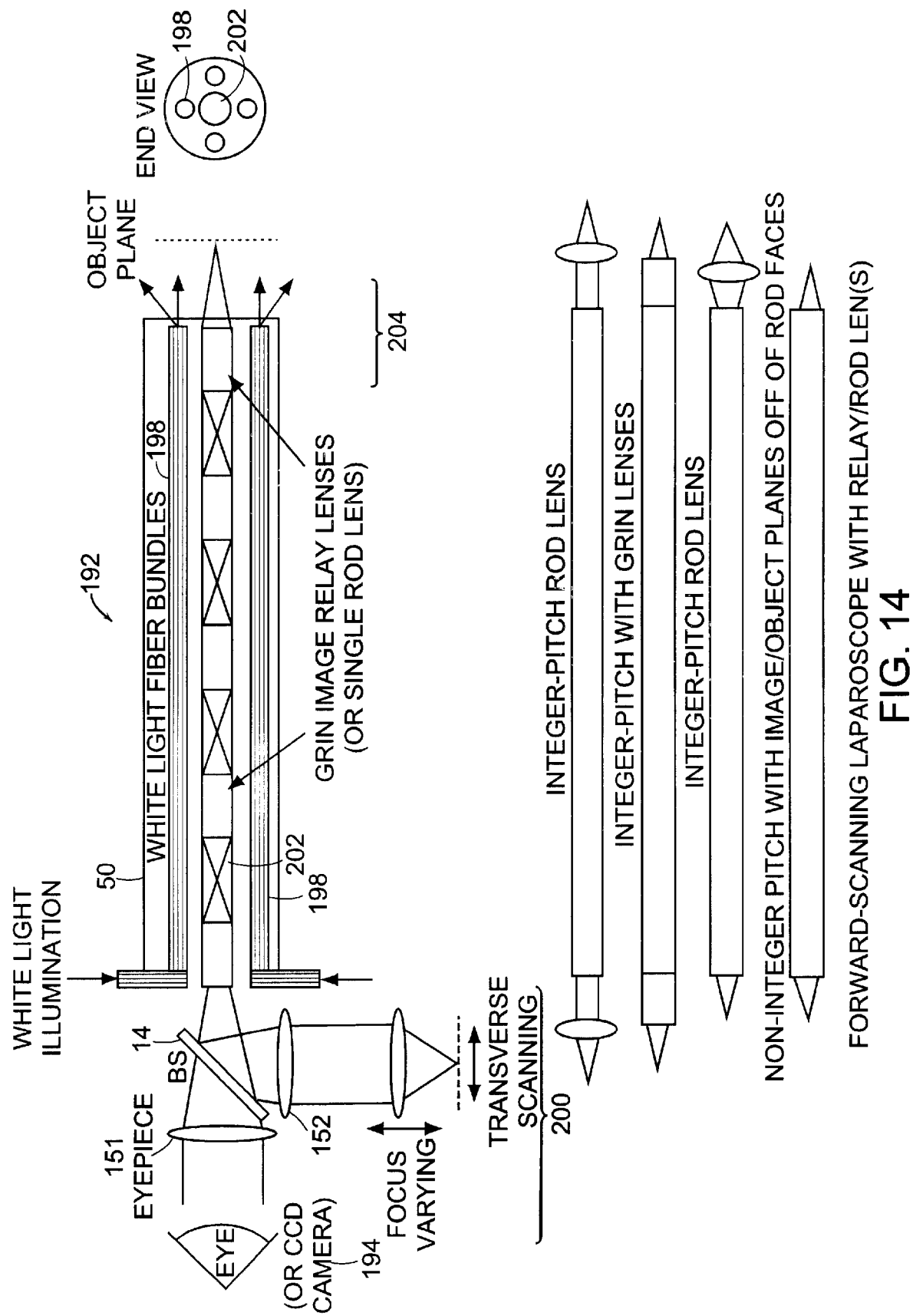
FIG. 14 is a longitudinal sectional view of an embodiment of a forward-scanning laparoscope with relay/rod len(s).

The design of the forward-scanning hand-held probe represents a general method of transverse displacement that is modular in design. Using the probe to transversely displace a focus in a forward-imaging plane is useful in other optical instruments such as a rigid endoscope or laparoscope. A laparoscope is an optical device that is used typically in medical applications to visualize tissue surfaces with magnification at a remote internal site. The concept of laparoscopic surgery has contributed to minimally invasive surgery; the idea that surgical procedures can be performed without large incisions and without exposing internal tissues during an open-field surgical procedure. As shown in FIG. 14, the laparoscope 192 consists of a rigid cylindrical enclosure 50 1–2 cm in diameter and 10–50 cm in length. The proximal end 200 contains optics that permit the operator to visualize the tissue surface located at the distal end 204. Alternatively, a CCD camera 194 can be mounted at the proximal end 200 with the en face image of the tissue appearing on a video monitor (not shown). Optics contained within the laparoscope 192 relay the image of the tissue in the object plane to an image plane at the proximal end 200. Additionally, there are white-light fiber-optic bundles (198) that run parallel to the imaging optics which provide illumination of the tissue surface. Typical surgical procedures using laparoscopes involve inflating the human abdominal cavity with a gas to provide space to visualize internal organs and to manipulate various surgical instruments within the cavity.

The integration of OCT forward-directed imaging into the laparoscope design offers the possibility of sub-surface imaging of intra-abdominal and other internal organs and structures. Sub-surface imaging can significantly complement the en face imaging that is currently performed with laparoscopes and white-light illumination. Additionally, the en face imaging significantly complements the sub-surface OCT imaging by allowing the user to simultaneously visualize the OCT scan location at a remote internal site. FIG. 14 illustrates the optical design of a forward-scanning laparoscope. At the proximal end 200 are optics which permit the simultaneous en face viewing and OCT imaging utilizing the same optics along the length of the laparoscope. A transverse scanning mechanism (not shown) is employed based on either those described in FIGS. 4–8, galvanometer scanners, or the modular concept of the forward scanning probe. These proximally located scanning elements can be extended to two dimensions and permit arbitrary scan patterns at the distal end 204 of the laparoscope. This arbitrary pattern can be observed and controlled by the operator through the laparoscope via the coincident visible aiming beam. Alternatively, the CCD imaging camera 194 can display the scan location, pattern, and direction. In the design shown in FIG. 14, a transversely scanned beam is focused by a lens 152 and fully reflected by a beam splitter 14 which transmits visible wavelengths, but reflects near infrared wavelengths. The OCT imaging beam is focused at the image plane of the laparoscope relay optics 202. The relay optics 202 consists of either a series of GRIN or relay lenses or a single GRIN rod lens, or other type of lens as is known in the art. In either arrangement, the result is a relay of the image plane to the object plane located distal to the end of the laparoscope. Hence, translations of the OCT beam focus in the image plane are relayed as translations in the object plane where the tissue sample is located. As stated above, an alternative to transverse scanning is to locate a angular scanning device(s) in a pupil plan at the distal end of the laparoscope.

The use of a series of GRIN or short rod lenses separated by air spacings often limits the wavelengths that are able to be transmitted through the laparoscope. Using a single rod lens with a gradient index profile, multiple wavelengths can be propagated through the rod. The effect would be separate object and image planes for large differences in wavelength. Rod lenses are typically defined by their pitch length. An integral pitch length rod lens will relay a non-inverted image from one face to the other. In this case, a beam which is focused into the proximal end of the rod lens will be focused at the distal end as if the rod was of zero length. For rod lenses that are of n/2 path lengths, where n is an odd integer, the image at the opposite rod face will be inverted. For rod lenses of other pitch lengths, the system resembles a focusing lens plus additional distances and hence, constructs an image at image/object planes located given distances away from the faces of the rod lens. Typically, these non-integral pitch length rod lenses are used in conjunction with additional focusing/collimating lenses. These lenses can be small standard lenses, ball lens, or additional GRIN lenses which can be attached directly to the rod lens.

The magnification of the lens/rod lens of the laparoscope sets the resolution and depth-of-field as well as the magnification of the displacement of the scanned beam. As was described earlier, techniques of focus varying can be performed by adjusting the separation between various optical components and hence varying the magnification. Focus positioning can be performed by displacing a distal focusing lens in the axial direction if the beam exiting the rod lens is collimated.

Referring again to FIG. 14 for simultaneous visualization of the scan location, an eyepiece lens 151 is used to image the image plane, through the beam splitter 14, on to either the human eye or a CCD 194 camera. White-light illumination is delivered through multi-mode fibers 198 located radially around the relay optics 202. The difference in wavelengths between the OCT imaging beam (e.g. 1300 nm) and the visible wavelengths ($\approx 650 \mu$m) when passed through the same relay optics 202 results in non-coincident image/object planes. This, however, can be compensated for by adjusting the location of the eyepiece 151 and focusing lens 152 located at the proximal end. To effectively image and visualize the tissue, the object planes for the two wavelengths are made to coincide. At the proximal end, however, there will be two image planes, one for each wavelength. By positioning the eyepiece 151 and OCT imaging beam focusing lens 152, each wavelength can effectively be relayed down the laparoscope 192 to a single coplanar object plane. Alternatively, a chromatic optical element(s) can be used in the common path to maintain a common image plane.

Figure 15:
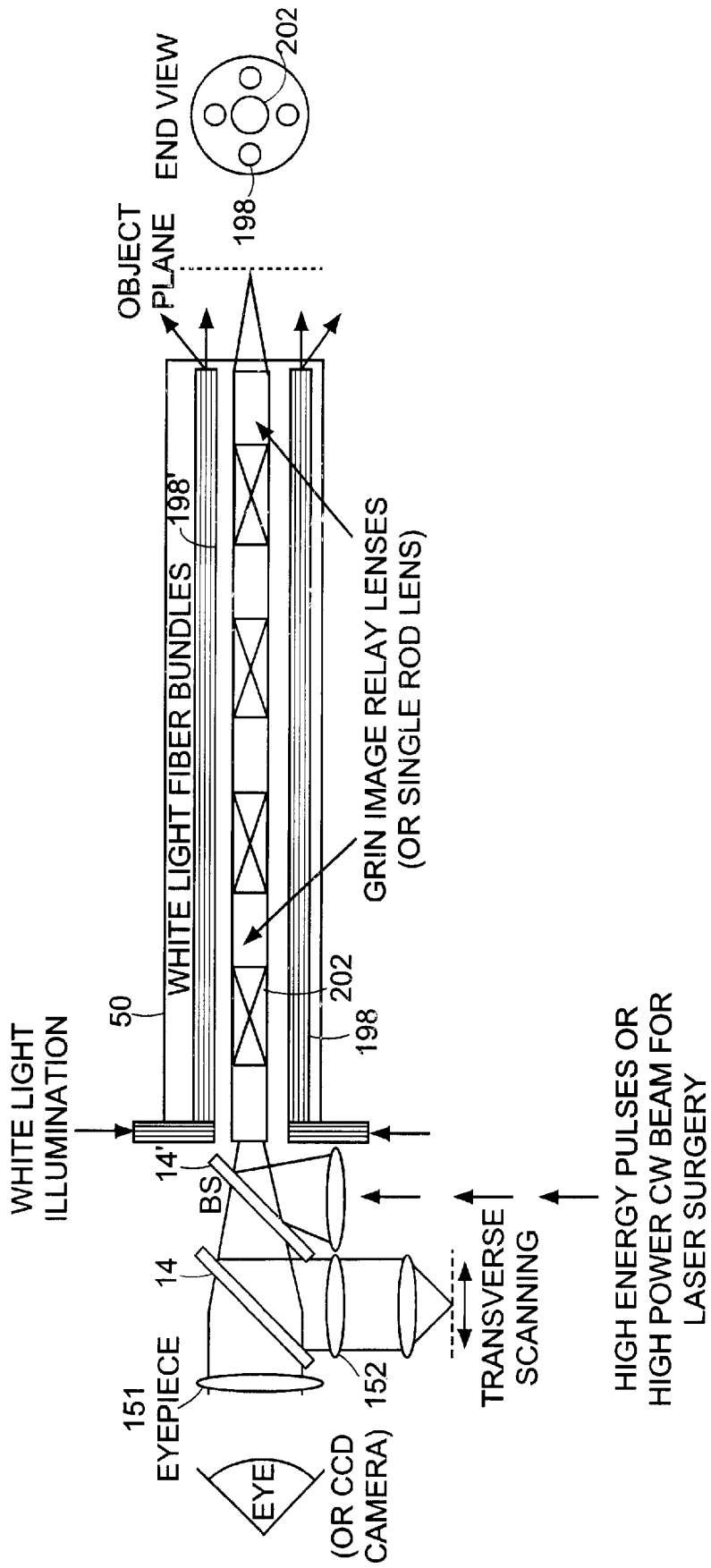
FIG. 15 is a longitudinal sectional view of an embodiment of a forward-scanning laser surgical laparoscope.

Just as modifications were implemented in the hand-held probe to permit the delivery of high-energy/high-power laser light, similar modifications can be implemented in the forward-scanning laparoscope. Shown in FIG. 15, one modification includes the addition of a second beamsplitter 14' to allow the high-energy/power light to enter the relay optics 202 and be delivered to the distal end and the tissue. To allow room for this additional beamsplitter 14', the focal lengths of the eyepiece 151 and image beam focusing lens 152 are lengthened. An alternate design maintains the locations of the proximal optics but replaces one of the white-light fiber bundles 198' with the multi-mode fiber which will deliver the high-energy/power light. Alternate optical embodiments that provide for the visualization, transverse scanning, and high power laser ports can be used as is known in the art. We note also that non-scanning OCT or other optical imaging technologies, such as parallel detection using an area-imager, can be used in this laparoscope application in place of a transverse scanning approach shown. Finally, we note that yet another embodiment has the surgical laser integrated into the OCT imaging port. For example, when one of the embodiments in FIGS. 4–8 are used for the OCT port, the surgical laser can be integrated via a WDM coupler (or other means) to deliver the surgical light to the exact spot being imaged. Thus good alignment is assured using this method since both the OCT and surgical light emanate from the same single-mode fiber.

This integrated laparoscope design will combine the ability to visualize intra-abdominal contents or other internal body structures via minimally invasive surgical procedures with sub-surface OCT imaging of architectural morphology and the ability to thermally or mechanically disrupt tissue using laser surgery.

Surgical Microscope

Forward-directed scanning can be integrated with existing surgical or dissecting microscopes to permit imaging of an arbitrarily oriented sub-surface tomographic plane to be performed simultaneously with en face visualization. Dissecting or stereo microscopes are typically binocular microscopes with long working distances (low numerical aperture (NA)) and large confocal parameters. They are frequently used in the research environment for low magnification of large samples that cannot be placed on the stage of a high-magnification, high NA microscope. Surgical microscopes with long working distances and long depths-of-fields are utilized in microsurgical techniques to enable the surgeon to visualize small structures such as arteries, veins, tendons, and nerves. Use of these microscopes is critical during procedures involving the reattachment of severed hands, feet, and limbs as well as the reconstruction of delicate structures around the face, head, and neck.

In all of these microsurgical procedures, visualization of the small structures is crucial for success. Because most surgical microscopes only provide the en face surface profile of tissue and structures, the integration of OCT for subsurface, cross-sectional or en face imaging of these structures offers an improved degree of visualization and information in order to perform a successful operation. The integration of forward-directed scanning with a surgical/stereo microscope, however, is not only limited to medical applications, but is useful when acquiring images at high-resolution. If the object to be imaged has dimensions that are difficult to view with the naked eye, then positioning the optical imaging beam on the sample will be equally difficult. Use of an integrated stereo microscope will enable the user to view the precise scan location on the sample. Because most surgical/stereo microscopes offer accessory ports for the attachment of CCD video cameras, the en face view, along with a visible aiming beam coincident with the near infrared imaging beam, can be captured and stored on either video tape or digitized and stored on computer storage media.

The concept of the forward-scanning surgical microscope 210 is illustrated in FIG. 16. Three scan methods are shown. In FIG. 16a, the optical fiber 57 from the sample arm of the OCT imaging engine is inserted into a collimator 67. The collimated beam is directed through a pair of galvanometer scanners 206 before passing through a focusing lens 152. The orthogonal scanners enable the forward-directed imaging beam to be scanned in arbitrary patterns on the specimen or sample. This arbitrary pattern also enables the acquisition of multiple cross-sectional planes for 3-D image acquisition. As the beam is converging to a focus, a beamsplitter 14 mounted at 45° redirects the near infrared imaging beam and the visible aiming beam downward and coincident with the field of view of the microscope optics. The beam splitter 14 is coated to reflect the imaging and aiming beam wavelengths while allowing other visible wavelengths to transmit. The focusing lens 152 will focus the imaging and aiming beams at two different locations. Since the visible aiming beam is only used to trace the location of the imaging beam, its focal position is relatively insignificant.

A second method for forward-scanning is shown in FIG. 16b. This concept reiterates the modularity of the forward-scanning instruments. The methods previously can be used to perform forward-directing scanning beneath a surgical/dissecting microscope. The cylindrical enclosure 50 or probe 164 can be attached to the scope 210 to place the forward imaging plane on the sample which is positioned for viewing by the microscope 210. One of the advantages of this method is arbitrary positioning of the probe 164 around the microscope 210 with quick removal for hand-held operation. To avoid the field-of-view of the microscope 210, however, the probe 164 can be positioned at an angle with respect to the imaging axis of the microscope 210. This implies that the cross-sectional image obtained with the imaging probe 164 will not be in the same orientation as the en face view. However, because of the large working distance and long depth of field, the probe 164 can be placed within 10–20° of the microscope axis if the dimensions of the probe 164 are minimized. Alternatively, a fold mirror (not shown), similar to the beamsplitter in FIG. 16a can be used to allow a freely held probe to be positioned horizontally to access the specimen from along the microscope visual axis. Linear scans at arbitrary angles can be obtained by rotating the forward-directed imaging probe 164 about its axis. If the scanning probe is attached to the microscope 210 and specimen is placed on translation stage 217, the stage 217 and/or and imaging probe 164 can be rotated about a fixed point on the specimen to provide various angles for imaging. As in the other devices, two-dimensional scanning can be performed by incorporating multi-axis cantilevers or other two-dimensional displacement mechanisms. Although the confocal parameter of this device is large, focus varying and focus positioning can be incorporated to improve the flexibility of the device and its ease-of-use when integrated with the microscope 210.

A visible aiming laser could be included in the probe unit 164 to easily facilitate registration of the en face microscope view and the OCT image. The visible aiming light would enable the operator to visualize where the scan of the sample is being made. In addition, the microscope can be designed with a small monitor 167 to allow the OCT image to be seen directly through the eyepiece 218 so a surgeon/operator may remove the probe 164 and freely move it about the sample while observing the scan along the surface via the visible aiming beam and see the tomographic projection below the surface via the OCT image in the eyepiece 218. Furthermore, the hand-held probe 164 may contain a therapeutic device such as discussed with respect to FIGS. 12 and 13.

An alternative to the modular probe concept which permits cross-sectional imaging along the same axis of the microscope 210 is shown in FIG. 16c. This design utilizes the piezoelectric cantilever 74 described in earlier sections. The cantilever 74 is attached to a translation stage 214 so that flexure of the cantilever 74 results in an arc swept out in the direction orthogonal to the stage 214 translation. At the end of the cantilever 74, a fiber/GRIN lens unit 63 is attached so the optical imaging beam is directed downward toward specimen. This unit can be positioned beneath the imaging optics of the microscope. A second stage (not shown)can be used to position the focus at given depths within a specimen. As a voltage ramp waveform is applied to the cantilever, the focus is swept in an arc through the specimen. The translation stage 214 can be used to acquire multiple arcs and construct a 3-D data set. Positioning this design beneath a stereo-microscope does limit the view of the sample or specimen to be imaged. However, the profile of the cantilever 74 and GRIN lens 63 can be made very thin and if placed far enough away from the focus of the microscope imaging optics, then the cantilever 74 will not be distracting to the user.

As mentioned previously an additional key feature of this invention is that the cross-sectional image obtained with the OCT or other type of imaging engine can be overlaid or otherwise combined so that a human user can simultaneously view both images through the eye piece(s) 218 or by other means. This includes the method where the probe 164 can be removed from the microscope 210 and freely held during a procedure or where a separate hand-held probe which is integrated with a mechanical or laser scalpel is used.

Note that the surgical microscope described in this section can be modified as described with respect to FIG. 2 to enable imaging in non-retroreflected modes.

High Numerical Aperture Microscope

Forward-directed imaging methods can be integrated with a high numerical aperture (NA) microscope. These microscopes are commonly used for research laboratory investigation of biological specimens as well as small, microscopic, material samples. Magnifications in these microscopes are higher than in the surgical/dissecting microscopes, typically between 50–400×. High magnifications imply short confocal parameters or depths-of-field for the microscope objectives. The numerical apertures for these objectives is higher ranging from 0.1 to 0.5 and higher. The principle advantage of integrating forward-directed optical imaging techniques with a high NA microscope is to allow the precise positioning of the imaging beam on the specimen or sample, particularly when the specimen is on the microscopic scale (100–1000 µm). In this device, focal position and beam characteristics are typically fixed, however, focus varying and positioning techniques may be incorporated. More importantly, focus tracking is critical for high NA embodiments as this distinguishes this scanning technology from all others. Focus tracking permits the coherence envelope of the OCT source to be continuously aligned with the focal region of the microscope objective and hence, collect image information only within the confocal parameter (the region of highest and relatively constant transverse resolution). As the sample is translated under the beam or the beam translated through the sample, inhomogeneities in the index of refraction of the sample will displace the predicted location of the coherence envelope as well as vary the focusing and beam properties of the OCT imaging beam. All of this can be corrected for as stated earlier. In general, the focus depth in the specimen is not simply related to any mechanical tracking parameter. Thus, custom generated waveforms will be generated to focus track inside a specimen. A high speed dynamic feedback system can be used to compensate as imaging is performed.

Figure 17:
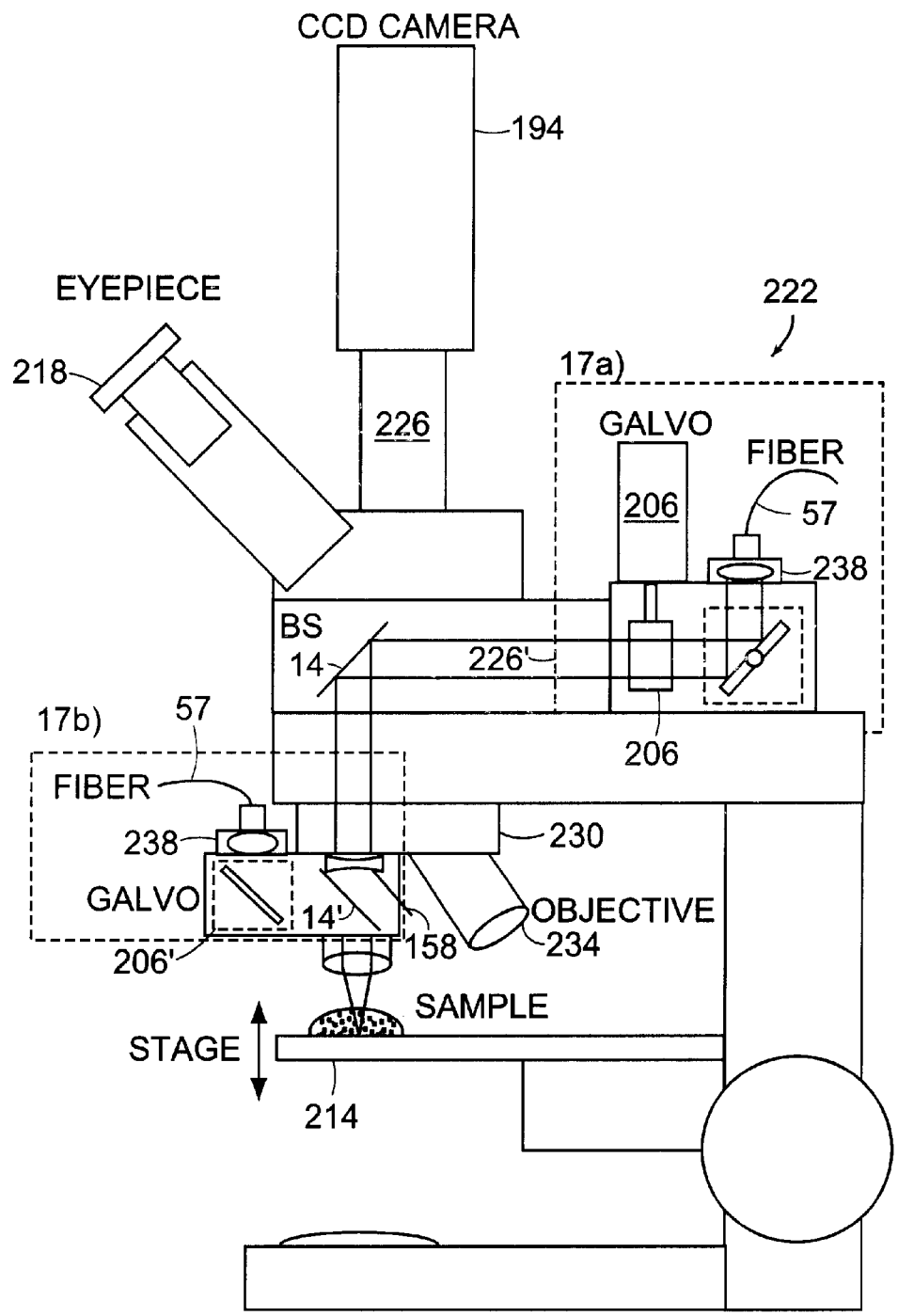
FIG. 17 is a longitudinal sectional view of an embodiment of a high numerical aperture OCT a microscope.

FIG. 17 illustrates the integration of forward-directed imaging with a high NA microscope 222. Commercial microscopes have been designed to provide several access ports which can be utilized for forward-directed OCT imaging. Typical ports include the camera port 226 used for CCD 194 or 35 mm cameras (not shown), the port 226' designed for direct illumination, and access to the optical path via the objective mount 230 . The microscope implementation in FIG. 17a demonstrates a CCD camera 194 attached to the camera port 226, a galvanometer scanning mechanism 206 to scan the imaging beam through the direct illumination port 226'. In FIG. 17b a galvanometer-based scanning mechanism 206' in an objective mount 230 which is inserted into the optical path of the microscope, prior to the microscope objective 234. The sample to be imaged is placed on the stage 214 of the microscope 222. The stage 214 is raised or lowered to position the focus of the imaging beam within the sample as well as to focus the image for visualization through the eyepieces 218. A monitor could also be added analogous to 167 in FIG. 16.

With respect to FIG. 17a the optical fiber 57 from the sample arm of the OCT imaging engine is attached to a connectorized fiber collimator 238 which collimates the imaging beam before being reflected off a pair of orthogonal galvanometer mirrors 206. The orthogonal galvanometers 206 allow arbitrary scan patterns at the object plane of the microscope 222 as well as for acquiring multiple image planes for 3-D data set acquisition. The collimated beam passes through the illumination port 226' and enters the optical path of the microscope by way of a beamsplitter 14 designed to reflect both the OCT imaging beam and the visible aiming beam while transmitting all other visible wavelengths. The collimated imaging beam is focused by an infinity-corrected microscope objective 234 which is antireflection coated for the wavelength of the imaging beam. The advantage of this implementation is the inconspicuous location of the forward-scanning device and its access via previously incorporated microscope ports. A limitation of this design is evident if direct illumination is desired. In this case, multiple illumination ports must be incorporated into the microscope design.

The second implementation shown in FIG. 17 utilizes micro-galvanometer scanners 206', or other forward-directed scanning methods (such as those described in FIGS. 4–8) in a similar configuration as described for FIG. 17. However, the entire unit is compact and small enough to insert between the microscope objective and the objective mount. This implementation also incorporates a beam splitter 14' designed to reflect the imaging and the aiming beams. If the microscope utilizes fixed-tube length optics and objectives, rather than infinity-corrected optics, a negative lens 158 can be placed within the optical path of the microscope to correct for the additional separation due to the insertion of the scanning mechanism housing. The advantage of this implementation is the ease of access for a wide variety of microscopes and the rapid installation prior to use. In both implementations, because the imaging wavelength is out of the visible spectrum, specially coated optics and objective lenses are required. These, however, should not be any more expensive than existing high-quality objectives available today.

In the previous high NA microscope forward-scanning designs incorporated with the OCT imaging engines, scanning is performed with depth priority. That is, the beam is positioned at one location via a two-dimensional scanning mechanism while the OCT engine varies the effective path length between the sample and reference arms of the interferometer in order to collect data in depth (z direction). The scanning mechanism then repositions the beam and another axial depth scan is performed. Imaging can also be performed with transverse priority by keeping the axial position fixed during a single transverse scan and then stepping in depth as subsequent transverse scans are acquired. In a three-dimensional mode, this is equivalent to the optical sectioning characteristics of a confocal microscope. The advantage of transverse priority scanning is a potential increase in speed and simpler focus tracking implementation hardware and software. Rapid transverse scanning can readily be performed with galvanometers and mirrors. The focus, as in focus tracking, or the axial position, cannot be varied as quickly. Additionally, high rates of transverse scanning can be performed if only a single fiber is displaced. If the fiber is attached to additional lenses or components, high speeds is more difficult due to the inertia of the lenses.

As mentioned above, the OCT imaging embodiment can be extended to include non-retroreflected imaging embodiments as described with respect to FIG. 2. For example the illumination could be scanned from above the sample and the detection light could be scanned as shown in FIG. 17 or could be scanned by other means such as locating the detection port below the sample stage. Alternatively, the illumination pattern could be stationary and only the detection port scanned.

Forward-Scanning Flexible Endoscope or Catheter

Figure 18:
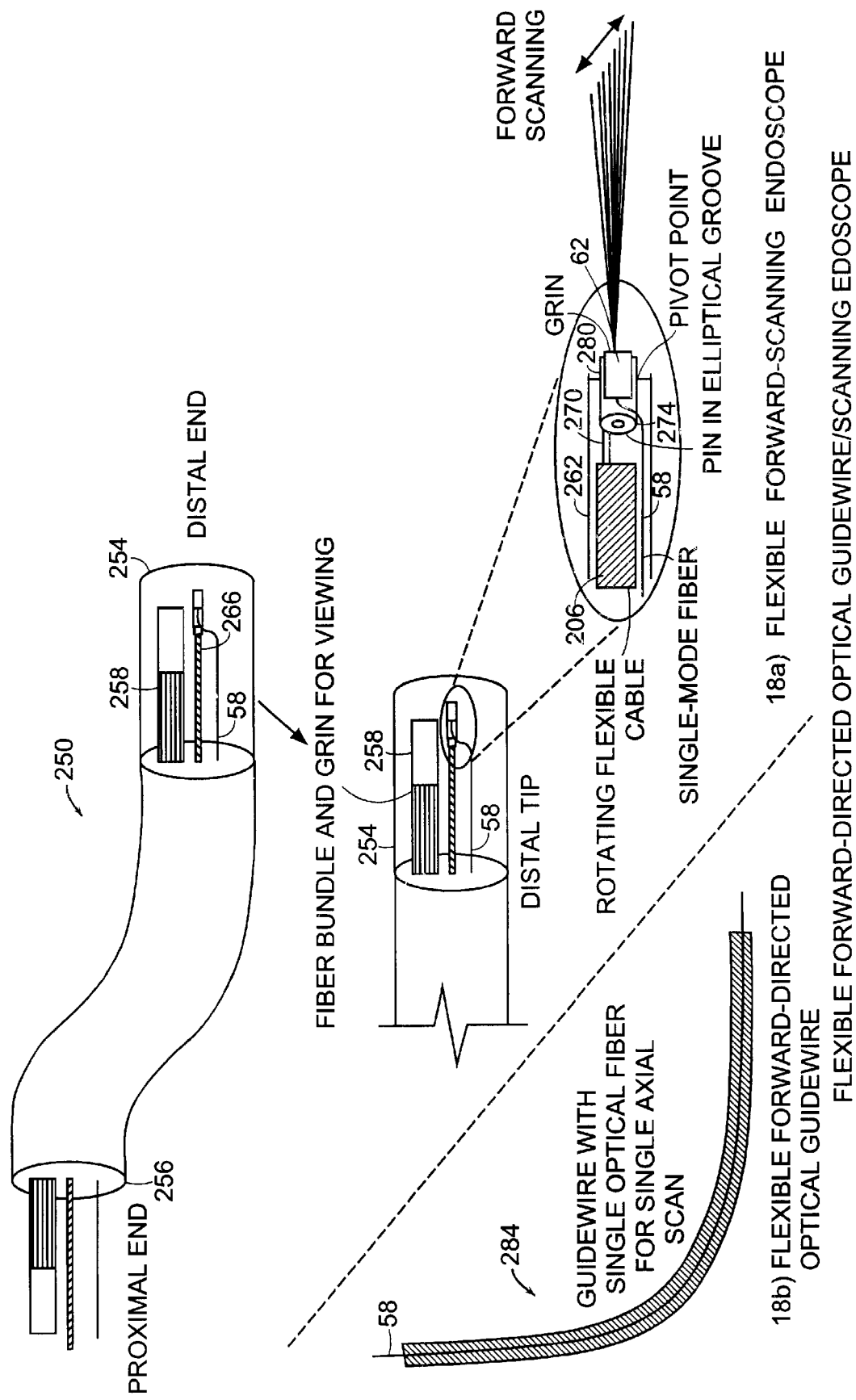
FIGS. 18a–b is a longitudinal sectional view of an embodiment of a flexible forward-directed optical guidewire/scanning endoscope.

A flexible endoscope (a type of laparoscope) can be use to image in non-vascular tissue and a flexible catheter or guidewire can be used for intravascular imaging. The concept of forward-scanning can be extended to devices such as these designed to access remote sites that are inaccessible with straight, rigid, optical instruments such as the handheld probe and the rigid laparoscope. Such sites include internal body lumens or cavities that have narrow and tortuous paths of access. In the industrial setting, internal examination of pipes or tubing with bends or angles requires a forward-looking, flexible imaging device. In addition, inspectors are often required to image sites that are located in tight, confined spaces or that lie "around corners". One design for a forward-scanning flexible endoscope, catheter, or guidewire is illustrated in FIG. 18. Performing optical imaging in the forward direction through a flexible endoscope, catheter, or guidewire incorporates new concepts. Housed within the flexible endoscope, catheter, or guidewire sheath are two imaging techniques which are used to provide both an en face and cross-sectional view of the specimen or sample.

The first imaging technique contained within the flexible endoscope 250, catheter or sheath is designed for en face imaging and is performed through a sealed transparent tip 254 located at the distal end 254 of the device. A fiber bundle and lens combination 258 is used both for white-light illumination and en face viewing of the specimen. This imaging technique is used to guide the endoscope 250, catheter, or guidewire through the tortuous path to the site to be imaged with OCT. Once at the site, this fiber bundle 258 is used to visualize where OCT imaging is being performed by observing where the visible scanning beam is located.

The second imaging technique contained within the sheath is designed for OCT or other laser-based optical imaging of the specimen. Contained within an inner, second sheath 262 is a rotating metal or rigid-material cable 266. A metal pin 270 is located at the distal end of the cable and is displaced from the center of the cable axis. This metal pin 270 inserts into a groove 274 at the base of a pivoting GRIN, ball, or small lens housing 280. The GRIN lens 62 is located at the distal end of the housing 280, over the site where the housing pivots. In one embodiment a single-mode fiber 58 runs parallel to the sheath 262 and cable 266 and inserts into the GRIN lens housing 280 where it is fixed to the GRIN lens 62 at a given distance. Alternatively the fiber 58 may run inside the speedometer cable with appropriate sheathing to protect it (not shown). The fiber/lens separation and the lens characteristics determine the beam focusing properties of the endoscope, catheter, or guidewire and can be varied as in focus varying techniques. As noted, the GRIN lens housing 280 is free to pivot about an axis located at the GRIN lens 62. As the cable 266 is rotated at the proximal end 256 of the endoscope 250, catheter, or guidewire, the rotation is translated to the distal end to drive the GRIN lens housing 280. The displaced, rotating pin 270 on the cable 266, which is inserted into the groove 274 of the GRIN lens housing 280, causes the GRIN lens housing 280 to pivot back and forth.

There are a variety of designs for the pin and groove that influence the resulting scan pattern. For instance, the appropriately shaped elliptical grove will achieve a linear sweep of the forward-scanning light. Alternative groove designs may be circular and implement sinusoidal forward scanning of the emitted light from the endoscope. The linear (transverse) scanning of the forward-directed light is preferred since the dwell time (and hence signal-to-noise) on each transverse pixel is constant. One method to achieve this is to have the cable 266 rotated at the proximal end 256 at a constant angular velocity. The off-axis metal pin 270, from the perspective of the GRIN lens housing 280, is translated in one plane in a sinusoidal manner. To convert this sinusoidal displacement to a linear displacement, an elliptical groove is machined into the base of the GRIN lens housing 280 permitting linear pivoting of the GRIN lens 62. Forward-directed imaging using this method will result in a pie-shaped image in one cross-sectional plane. Multi-dimensional data sets can be acquired by rotating the entire endoscope 250, catheter, or guidewire within the lumen or cavity and collecting multiple pie-shaped cross-sections about a single central axis.

Forward-directed optical image data can be acquired without transverse displacement by using a flexible, forward-directed optical guidewire 284 shown in FIG. 18*b*.

A single-mode optical fiber 58 is located within the core of a metal guidewire or guidewire 284 made of other material. The distal end of the fiber 58 has some means of focusing the light into the specimen either by a molded, integrated, fiber lens or an attached micro-GRIN lens (not shown). This device permits collection of a single axial scan as the guidewire 284 is inserted into the lumen or cavity. Guidewires are used in nearly every catheter-based procedure to define the path of the catheter through the lumen. Often, the procedure is performed without visualizing via ultrasound or x-ray where the tip of the guidewire is located. The insertion of the guidewire is extremely critical when approaching sensitive tissue such as thin lumen walls or atherosclerotic plaques which are prone to rupture or dislodge and cause a potentially fatal thrombotic or embolic event. Although a cross-sectional image cannot be acquired using such an optical guidewire, the single axial ranging data can provide information regarding the tissue type and structural morphology distal to the end of the guidewire and reduce the likelihood of forcing the guidewire through sensitive areas. Note that in addition to this design housing only one single-mode fiber, multiple fibers bundled packed in a line or in two dimensions could be utilized to provide some imaging in parallel without any transverse scanning mechanism at distal end of the device. Each fiber could be connected to a separate imaging engine or scanned sequentially (using an optical switch or angular scanning optics) at the distal end.

Note that although GRIN lenses were discussed in this section describing FIGS. 18*a* and 18*b*, the use of other optical elements such as polished fiber up-tapers, spherical lenses, glass-molded aspheric lenses can be used. Furthermore, we describe the use of a rotating speedometer (or torque) cable 266, however, there are other actuation embodiment that can be used to pivot the distal optical module such as those described with respect to FIGS. 2–8. In general, this design is not restricted to pivoting the distal optics, but is possible with any of the previously described forward-scanning methods, if made small enough to be housed at the distal end of the flexible endoscope, catheter, or guidewire.

Figure 19:
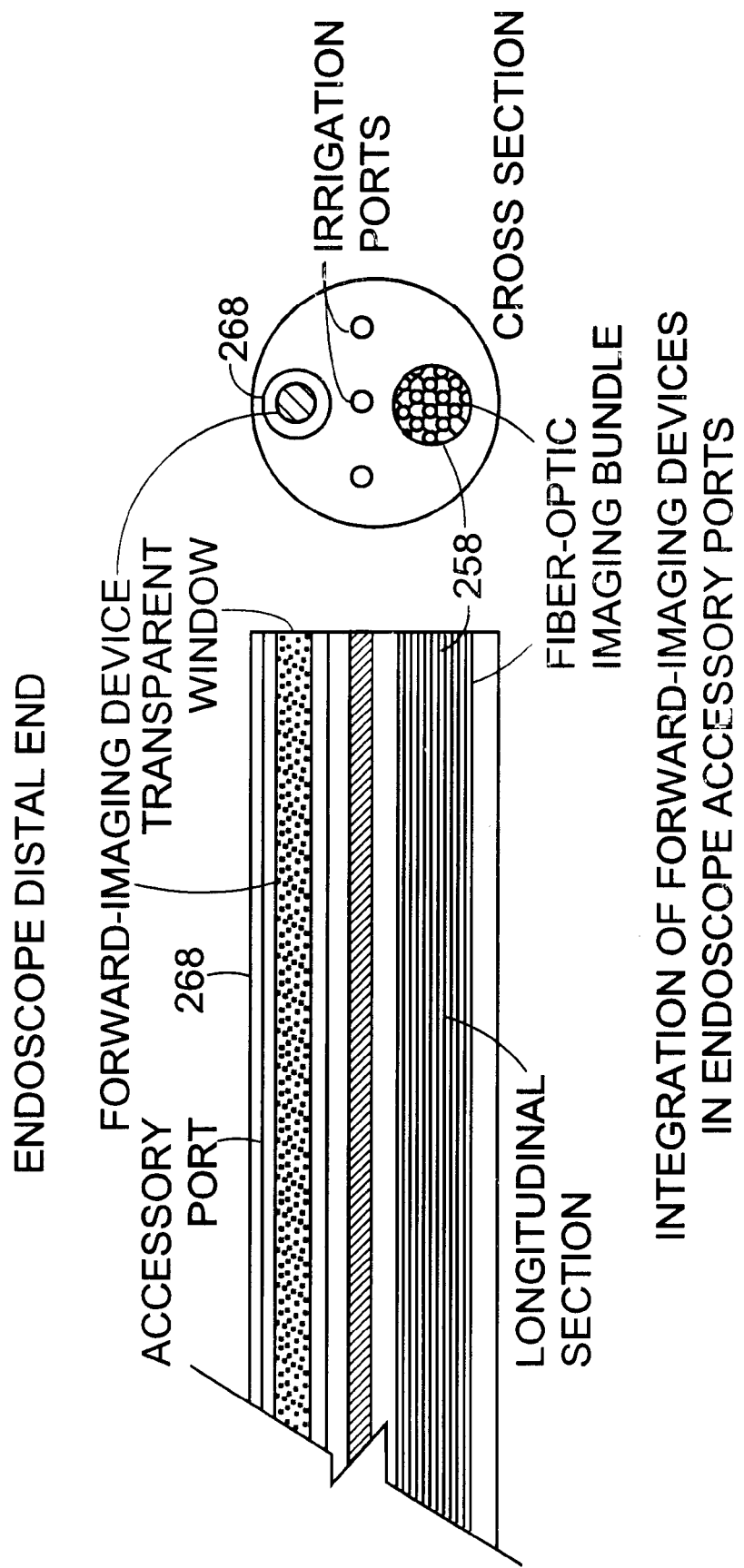
FIG. 19 is a longitudinal sectional view and a cross-sectional view of an embodiment of the integration of forward-imaging devices with endoscope accessory ports.

A recurrent point to note is the ability of these forward-scanning imaging devices to be implemented with existing medical/industrial imaging instruments. Because of the fiber-based design, outer diameters range from 1–3 mm for the flexible forward-scanning endoscope, catheter, or guidewire down to several hundred microns for the optical guidewire. These outer diameters permit the device to be inserted into the accessory ports 268 of current flexible endoscopes or catheters or guidewires as illustrated in FIG. 19 in longitudinal and cross-sectional views of the distal end. By integrating these instruments, OCT or laser-based imaging can be improved by utilizing the various additional ports for irrigation, micro-manipulation, and white-light illumination already implemented in the clinical instruments.

Forward-Scanning Fiber Bundle

Figure 20:
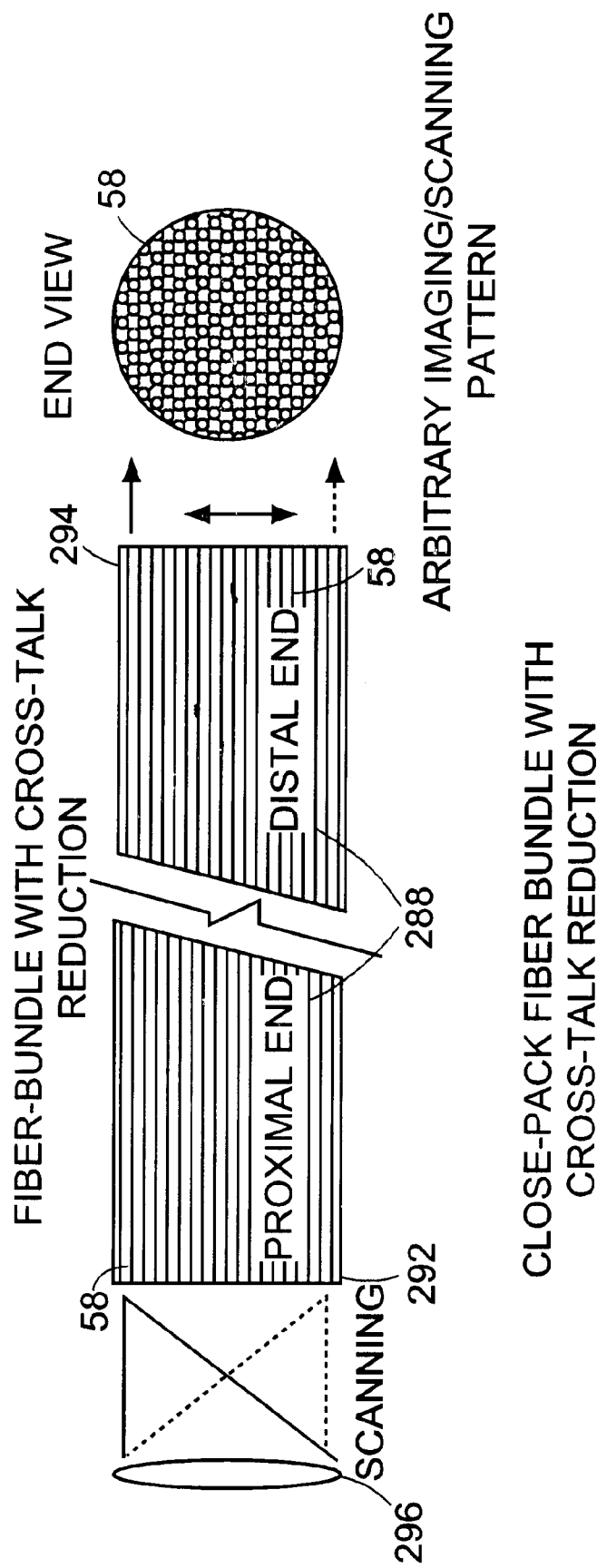
FIG. 20 is a longitudinal sectional view of an embodiment of a close-pack fiber bundle with cross-talk reduction.

Forward-directed imaging using a flexible fiber bundle 288 is another embodiment of this invention and is shown in FIG. 20. The flexible bundle 288 is composed of a large number of close-packed single-mode optical fibers 58. The orientation of the individual fibers at the proximal 292 and distal 294 ends of the bundle are maintained which implies that a scan pattern at the proximal end 292 is accurately represented at the distal end 294 of the bundle. A previous attempt to perform forward-directed imaging through a fiber bundle using low-coherence interferometry resulted in moderate to significant inter-fiber mode coupling which increased the transverse point-spread-function. This effect would lower the transverse resolution of the image. However, to address this limitation in previous approaches, in this design a highly absorbing material is inserted into the bundle 288 to surround each individual fiber 58. One possible material is a liquid suspension of carbon particles; or each individual fiber can be coated during the fiber manufacturing process. An alternative approach and/or complementary approach to using the cross-talk reduction material is to use signal processing algorithms. If the degree of mode-coupling is known or is predictable, image processing routines can be used to remove the artifacts induced by the cross-coupling.

With such a fiber bundle 288, forward-directed scanning can be performed in arbitrary patterns at the proximal face 292 of the bundle. A microscope objective or high numerical aperture lens 296 is used to focus the OCT imaging beam on to the proximal face 292 and to individually and sequentially address in time each fiber 58. At the distal end 294, the propagating light is focused at the object plane, distal to the end of the bundle, by an integrated fiber lens (not shown). Fiber lenses integrated into each fiber eliminate the need for additional, larger focusing lenses at the distal end and eliminate the aberrations induced with this type of optical setup. Alternatively, microlens arrays or a bulk optical lens group similar to that used at the proximal face could be used to relay and magnify or de-magnify the image. Transverse translation is accomplished at the proximal end 292 by placing either the microscope objective of the proximal end 292 of the bundle on a translation stage (not shown) that has sufficient resolution and precision to address each individual fiber 58 or by using a combination of angle scanning devices and lenses. Alternatively, a direct parallel detection of the image can be utilized.

As with previous designs, the flexible-endoscope can be integrated to guide or autonomously control laser and other surgical devices. For instance a single or multi-mode optical fiber could be integrated into the center of the imaging bundle.

Even with thousands of single-mode fibers, each only tens of microns in diameter, the overall diameter of the fiber bundle is on the order of 1–2 mm. Such a small, flexible device is ideal for integration in endoscope accessory ports or used independently for vascular access of small arteries and veins.

Atherectomy/Grinding Imaging Endoscope, Catheter, or Guidewire

Various atherectomy and grinding catheters and endoscopes have been designed and used to remove tissue or material at a remote site or close to highly sensitive structures. Many of these designs are small and integrated into rigid probes or flexible catheters. Typical applications include rigid forward or side-directed removal of vitreal strands at the vitreal/retinal interface and the forward and side-directed removal of atherosclerotic plaques within the human coronary arteries. In the first example, visualization is poor because of the small, nearly transparent structures that are being removed. In the second example, visualization is nearly impossible because of the location of the catheter within the blood-filled human coronary arteries. Because visualization is critical for distinguishing between normal and abnormal tissue, forward-directed imaging methods can be integrated with forward and radial-directed rotating blade/grinding catheters in order to image the tissue prior to grinding and removal.

Figure 21A:
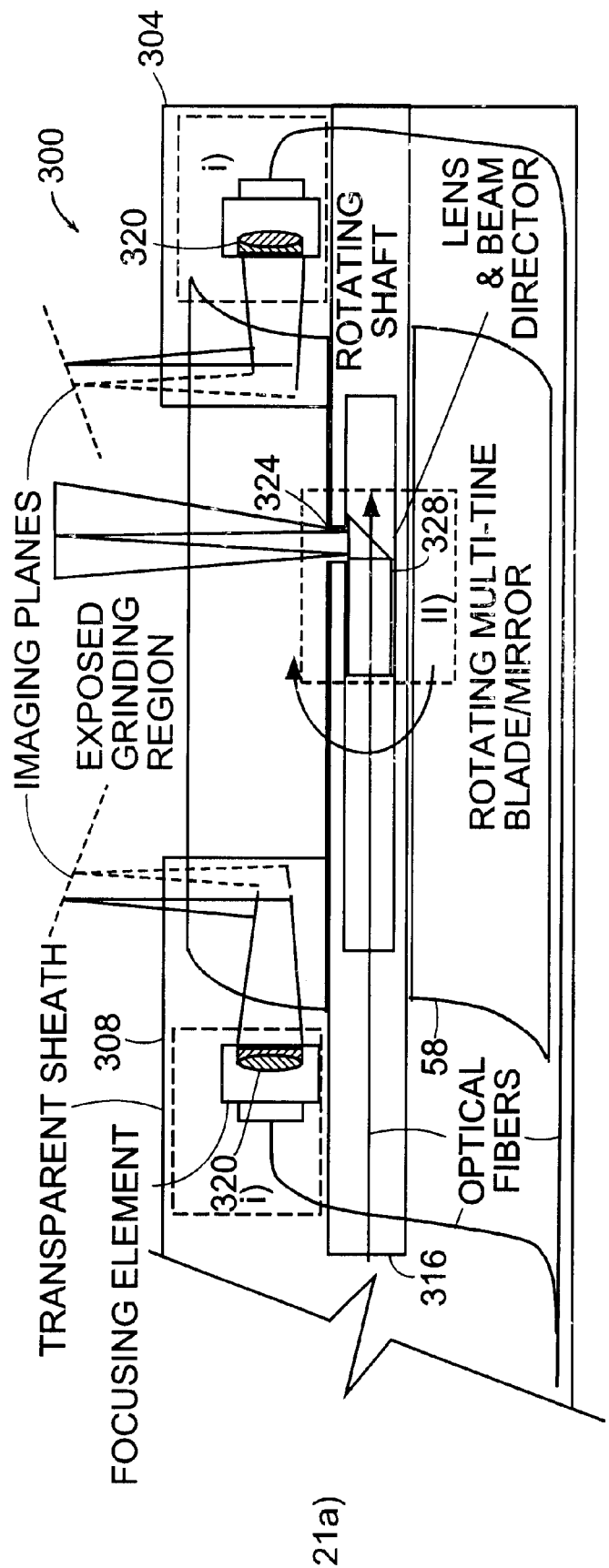
FIGS. 21a–c is a longitudinal sectional view of an embodiment of an imaging surgical grinding catheter.

One concept of an image-guided rotating blade catheter 300 is illustrated in FIG. 21a. FIG. 21ai shows the distal end 304 of a radial-directed rotating blade catheter 300 with additional imaging optics. The catheter 300 used for this procedure is flexible and of small diameter (<3 mm). The distal end 304 has a region of the outer sheath 308 removed to expose the rotating blades 312. This is the region where grinding or tissue removal occurs. Along the axis of the catheter is a rotating shaft 316 which is used to rotate the blade 312 at the distal end 304. In one embodiment the curved, rotating blades 312 also provide a mirror-like surface off of which the OCT imaging beam is reflected. The area of the blade 312 where the imaging beam is incident can be physically isolated from the grinding region in applications where the accumulation of contaminants or the deposition of blood which would decrease the reflectivity of the surface. One or a pair of single-mode optical fibers 58 run along the length of the catheter sheath 308. Each is attached to a focusing element 320 which focuses the beam at the object plane located outside of the catheter sheath 308 in the region to be removed by the rotating blades 312. To perform forward-directed scanning of the beam, the blades are machined at a precise angle and pitch (e.g. a helix) so that as the blade rotates in front of the beam, the reflected beam is directed to a different location along the imaging plane. The imaging plane may not necessarily be a single line and hence a straight cross-section. This cross-section can provide useful information about the tissue morphology and composition prior to removal by the rotating blades. We note that the device used in FIG. 21 could be used solely for diagnostics. That is the device could be completely sealed (eliminating problems with debris clouding the field of view) and the rotating helical blades used simply for performing lateral imaging.

Alternatively, in FIG. 21aii an imaging port 324 could be located within the rotating shaft 316. The optical fiber 58 could run along or within the axis of the rotating shaft 316 and a small beam director 328 (e.g. GRIN lens attached to a small prism) could be used to direct light to the specimen. The essential design feature is that the rotation used to drive the cutting blade is used to simultaneously drive and scan the optical radiation pattern. Multiple imaging ports (not shown) could also be used. Alternatively, the optical imaging port could be designed so as to allow automated or manual adjustment of the location of the beam director element along the axis of the rotating shaft as shown by arrow in FIG. 18aii. Normally the imaging optics in the beam director would be arranged to achieve a circular spot of the appropriate diameter and confocal parameter as is known in the art and indicated. In some applications it is desirable to cover a wider area while sacrificing resolution. For instance, if the primary goal is simply to perform ranging to the closest feature to the tissue wall, one possible enhancement to the optical design is to use a cylindrical lens to widen the footprint of the beam along the axis of the rotating shaft as indicated.

Figure 21B:
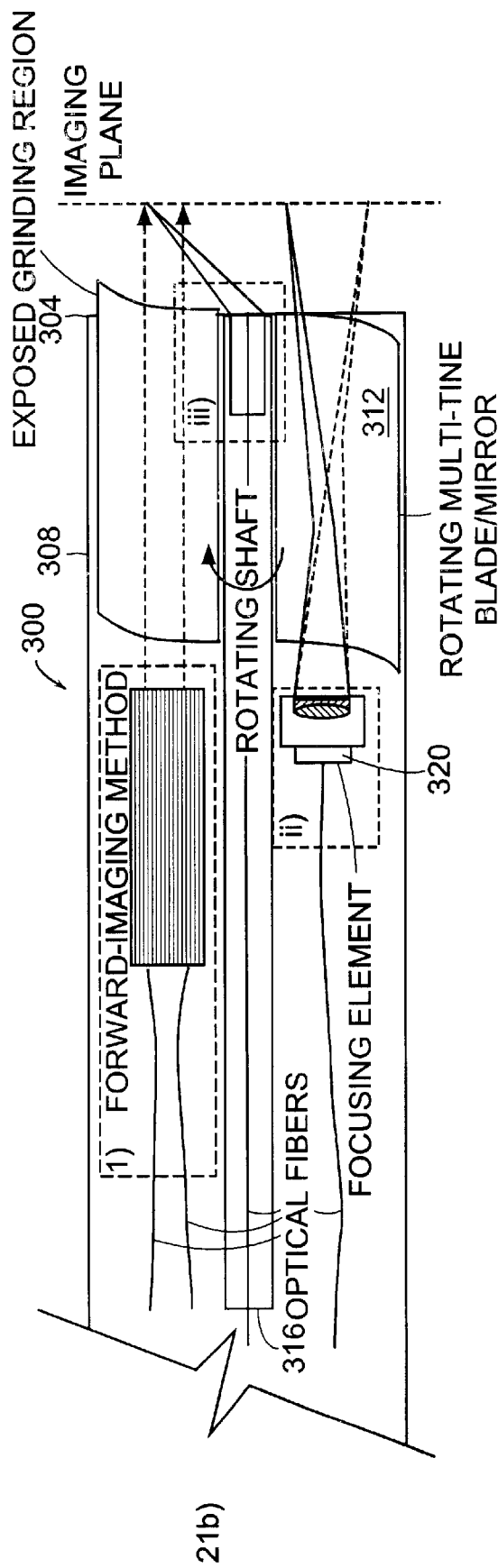

A forward-directed rotating blade with forward-directed imaging is shown in FIG. 21b. The concepts are similar to those described above except here the distal face 304 of the catheter 300 is open and is the site of tissue removal. Three forward-imaging concepts are illustrated. In FIG. 21bi, various forward-directed scanning mechanisms can be implemented as was shown in FIGS. 4–8. Imaging is performed through the rotating blades 312 with the imaging plane located distal to the end 304 of the catheter 300. If the pitch of the rotating blades 312 is small, the duty cycle for imaging will be large. There will only be brief periods when imaging cannot be performed because the blade 312 is in the beam path. Acquisition can also be gated to only occur when the blade 312 is out of the beam path. The second method in FIG. 21b.ii uses a single focusing element 320 and relies on the curvature or pitch of the blades 312 to reflect the imaging beam. As the blades 312 rotate, the focus of the beam is translated across the imaging plane and is used to acquire a cross-sectional image of the tissue prior to removal. As stated above, this type of deflecting technique can be used solely for diagnostics.

Alternatively or in addition, in FIG. 21biii, an imaging port 324 could be located within the distal portion of the rotation shaft 316. As described in reference to FIG. 8 and other previous figures, a small spinning beam director 328 can be used to sweep out a conical section in front of the rotating grinding region. One of the attractive features of this embodiment is again that the spinning shaft which drives the multi-tine blade is also used to scan the optical radiation pattern. We note that a variety of designs exist to optimize the shape of the distal portion of the cutting blade and the illumination pattern of the optical port to ensure optimal real-time imaging of the tissue prior to and during cutting.

Figure 21C:
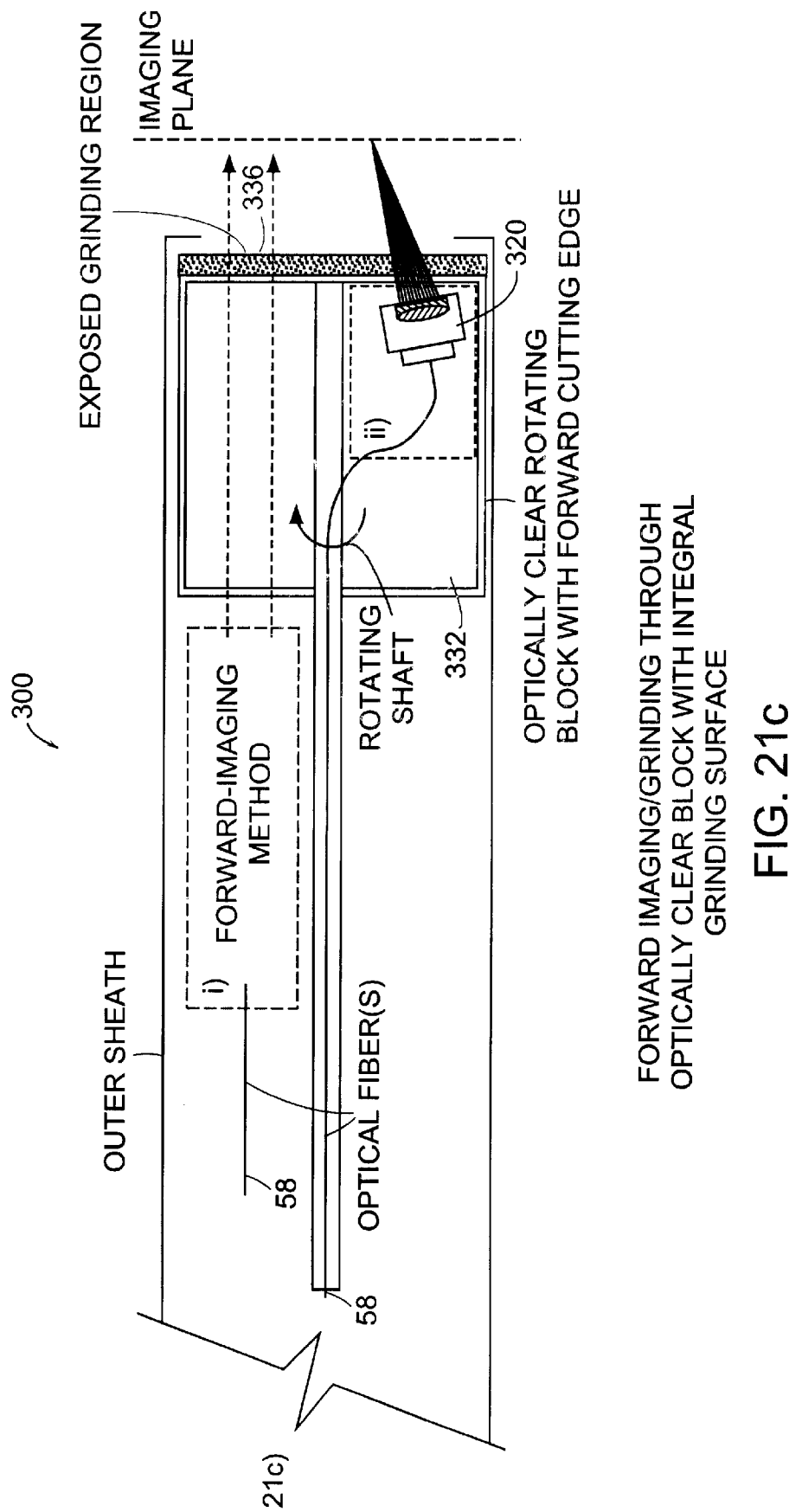

FIG. 21ci shows another embodiment of a forward grinding catheter/endoscope 300. In this embodiment an optically clear block 332 with an integral grinding surface is rotated. The OCT or other laser imaging system is used to image through the grinding element 332 and into the tissue/specimen of interest. In the embodiment shown, only part 336 of the forward surface of the grinder 332 is open to interface with the tissue. Alternate designs can convert the circular motion of the rotating shaft 316 to a gearing mechanism that rotates the clear grinding block 332 whose spinning axis is rotated 90° with respect to the block shown in FIG. 21C.

Alternatively or in addition, in FIG. 21cii, an optical beam director element could be located offset from the axis of rotation but within or attached to the spinning grinding block 332 itself. The offset radius and the emission angle with respect to the axis of rotation can be tailored for the application of interest. The concept in FIG. 21cii of a spinning element with a grinding surface and an internal or external optical imaging port can be extended to include a transverse grinder as well.

One of the central concepts of this aspect of the invention is the use of the mechanical motion of rotational or reciprocal cutting tools to also drive the optical imaging port which can be coupled physically with the cutting tool so that motion of the cutting tool is used to simultaneously perform scanning thereby maintaining registration of the cutting tool surface and the image field of view.

Inherent to these and other designs of image guided therapeutic devices related to this invention is the fact that imaging is performed simultaneously with an invasive cutting tool. This increases the likelihood that tissue or blood may contaminate the instrument and reduce the ability to acquire images. The limitations can be addressed by implementing either irrigation or aspiration ports within the catheter or endoscope to remove unwanted blood or tissue as is known in the art.

Integrated Microchip for Image Acquisition

In all of the previous forward-directed imaging techniques, the distal end of the probe or device was used primarily for scanning, beam delivery, and collection. With the ever increasing ability to micro-fabricate electrical and optical components on silicon or semiconductor substrates, it will be possible to perform optical or OCT imaging with a single microchip located at the distal end of a probe or flexible catheter.

Figure 22:
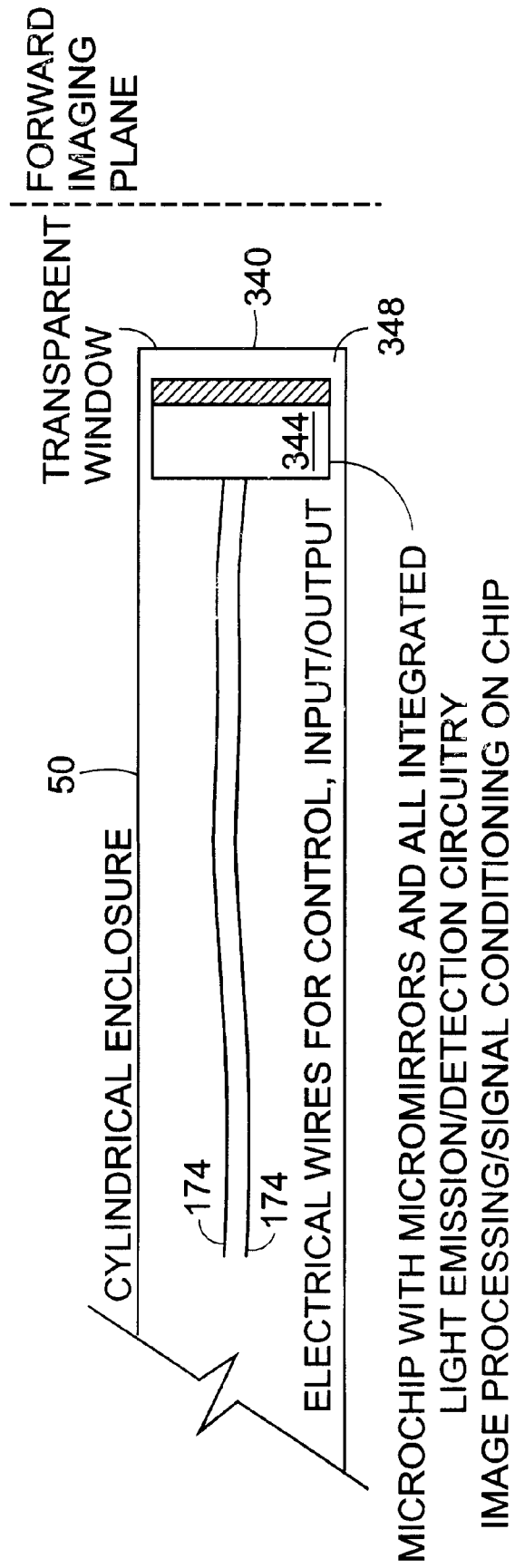
FIG. 22 is a longitudinal sectional view of an embodiment of the distal end of a device with an integrated microchip for image acquisition.

As shown in FIG. 22, the catheter sheath or cylindrical enclosure consists of a distal transparent window 340 and is only a few millimeters in diameter. The connections between the integrated microchip 344 and the remaining instrumentation consists of only a few electrical wires 174 for control, input, and output of data.

Located on the microchip 344 are the necessary microfabricated components for the light sources, interferometers, beam focusing optics, beam directing or scanning, light detection, and detection, filtering, and signal processing electronics. Interferometer arm path length changes are performed with micro-mechanical components or with non-mechanical means as described previously for the OCT imaging engines. Although illustrated in a small, forward-facing chip in FIG. 22, the integrated components could occupy the entire distal end 348 of the flexible catheter or probe. Input to the microchip 344 include power, control for source output, wavelength, tuning, etc., as well as parameters for image scan length and beam focusing characteristics. Output from the chip includes any feedback signals for control and the data stream used to display the image.

Since all of the components used in the OCT imaging engines and forward-directed imaging can be implemented on a microchip, future reductions in micro-fabricated components will only lead to additional implementation in existing optical instruments or as autonomous imaging robots.

Optical Phased Arrays

Figure 23:
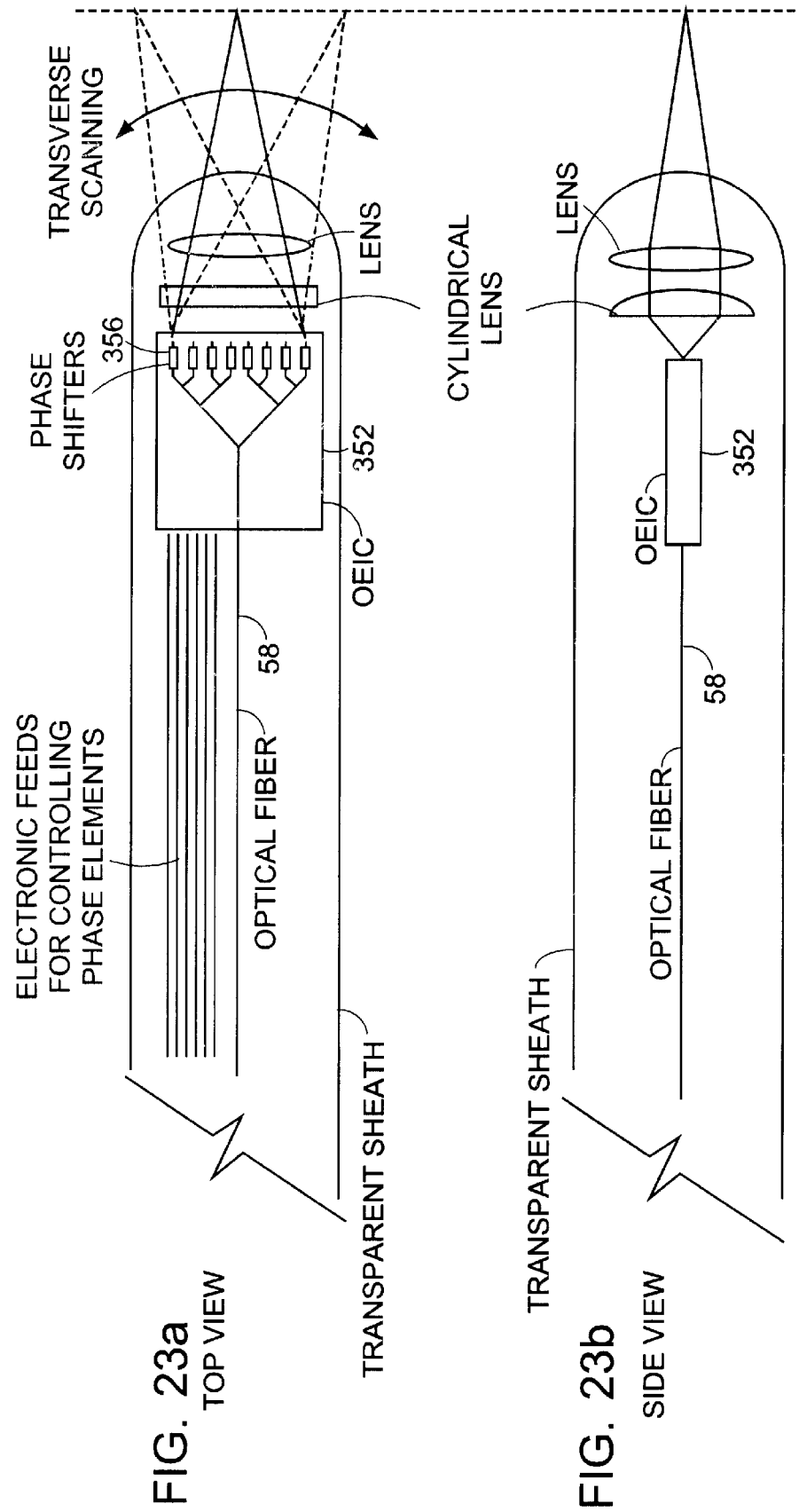
FIGS. 23a–b is a longitudinal sectional top and side view of an embodiment of optical phased array for forward imaging.

Another embodiment of this invention for scanning the radiation pattern from a probe module is to use a phase array as shown in FIG. 23. Phased arrays have the advantage that they contain no moving parts and thus can be scanned quickly. They rely on the precise relative optical phase of the emitted light from each array element which either constructively or destructively interferes with the emitted light from other array elements. By modulating the phase between individual elements, it is possible to arbitrarily position the location of the constructive interference (and hence, the focal spot) in a defined region surrounding the array. There are a variety of types of phased arrays that are known and regularly used in RF radar and communication devices. One example of an extension of this technology to the optical probe unit of this invention is to have a single-mode optical fiber 58 connected to an opto-electric integrated circuit (OEIC) 352. This OEIC 352 contains one or a series of beam dividers (not shown) which split the optical signal into N channels. The OEIC 352 may be made of silica on silicon ($SiO_2$/Si), $LiNbO_3$, InGaAsP, or other elements commonly used for creating optical waveguides and/or phase shifting elements. Each of the N channels contains an electro-optic or thermo-optic phase shifter 356. This phase shifter 356 may be on the same optical substrate as the beam divider waveguides or on a separate element optimized for phase shifting. By controlling the relative phase in between elements, arbitrary illumination patterns can be obtained. In particular if a time varying linear phase shift is implemented in between elements, the beam will be scanned off-axis as shown. The relative spacing between elements of the phase shifters 356 and the number of elements determine the amount of angle that can be scanned over and the far-field pattern. Note that a one-dimensional scanning pattern would require cylindrical or anamorphic optics to achieve the appropriate depth-of-field and scan pattern in the sample as shown. Note that semiconductor or solid-state optical amplifiers could be integrated onto the phased array to reduce the effect of absorption and splitting losses in the OEIC. In addition to the embodiment where one fiber feeds an OEIC it is possible to have N fibers feed the probe module 352 where the phasing and OEIC is implemented at the proximal end of the probe. However, this is much more difficult as perturbations along the individual fibers must be compensated for. By placing the elements along the axis of the probe, side scanning phased array embodiment is also possible. Note that for both the side-scanning and forward scanning embodiments it is important to minimize loss and maintain near equal path lengths (to less than approximately $1/10$ the system resolution) among the various elements. Otherwise the longitudinal point-spread-function and system resolution will be degraded. We note that although an end-fire 1-D phased array is shown, extensions to side imaging and 2-D phased arrays are a straight forward extension of this approach.

Another embodiment (not shown) for the phased array is to utilize multiple (e.g. 100) individual fibers arranged in either a linear format or as a two-dimensional array. Focusing optics may not be required for the array although beam conditioning optics may be necessary to optimize the performance of the array and to reduce the focal region of the array. For operation, the proximal end of the device must include piezoelectric or mechanical fiber stretchers which vary the length and/or rotate each fiber (and hence change the phase of the light) by several hundred microns, or enough to sufficiently vary the phase by 360°. In addition, since this requires beams to be propagated down each fiber as well as back-scattered light to be detected, the imaging engine must perform all of these operations in parallel. We note that this approach to control the phase in individual fibers despite catheter bending and fiber stretching must be done precisely.

Diagnostic and Therapeutic Applications of Forward-Scanning

Important components of this invention include designs and applications in connection with guiding or assessing the effects of therapeutic instruments which disrupt or remove tissue via abrasion, compression, blade excision, heat, shockwaves, or laser light. This guidance includes procedures which destroy tissue (as opposed to removing it from the site) such as applying RF, laser, or toxin additions to the site. Some of these designs have already been illustrated (e.g. FIGS. 12, 13, and 21). Others are straight forward extensions of the designs and methods already illustrated. This section will present some examples of methods and designs for additional diagnostic and therapeutic applications of this invention.

Implantation Devices

Figure 24:
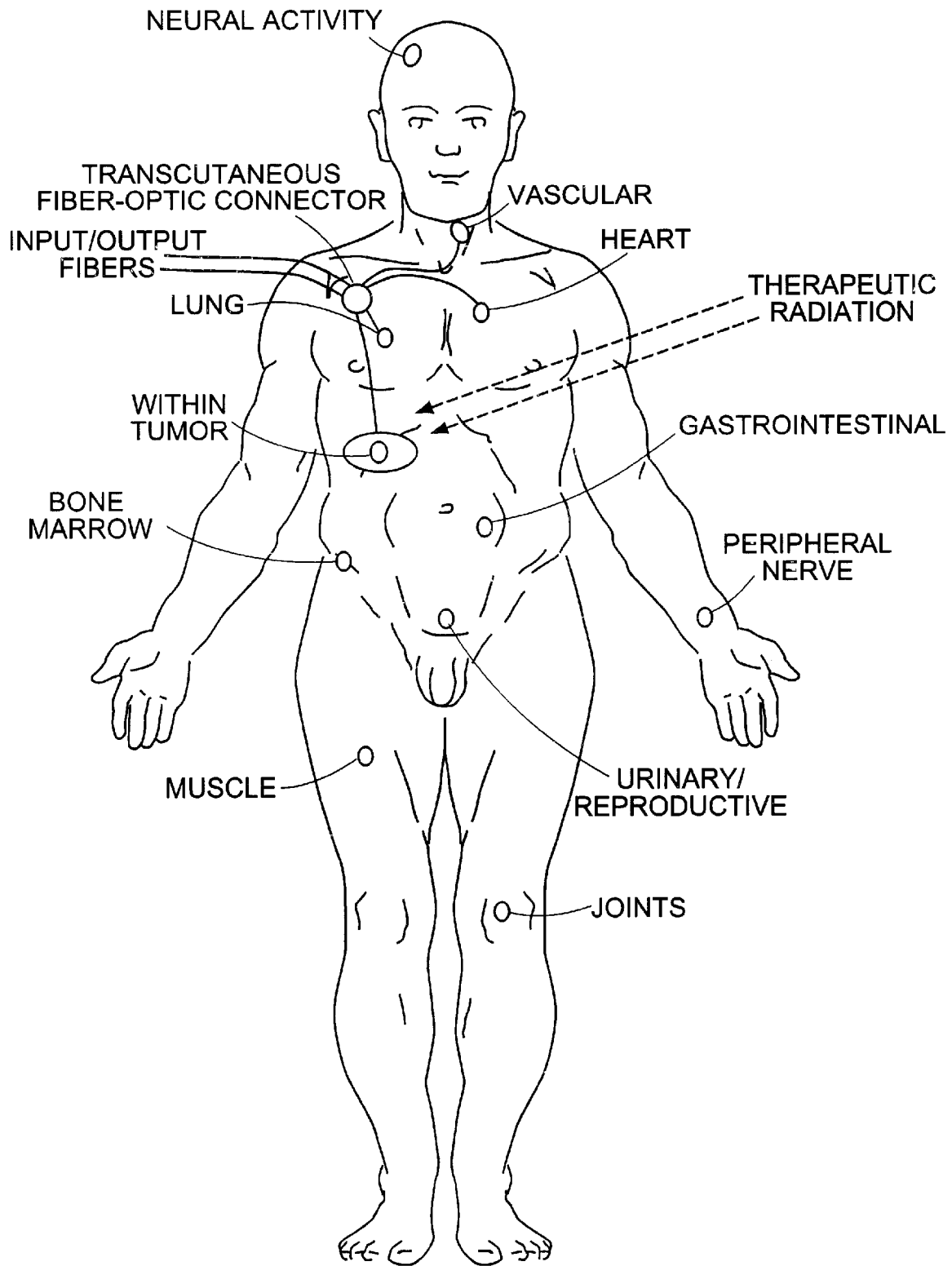
FIG. 24 is a frontal view of anatomical sites for implantable probes.

One embodiment of this invention is the concept of implantable or embeddable probes (or other devices) in living biological tissues or other structures/specimens such as a structural composite to allow continuous or periodic extraction information on the tissue or specimen that otherwise would be inaccessible or difficult to obtain. These probes could be implanted during a surgical procedure and left permanently attached or removed at some distant time point in the future when the concern of disease is eliminated or reduced to an acceptable level, or in other situations where the implant is no longer needed. An example of using implantable probes is shown in FIG. 24. The implanted fibers may consist of a single fiber or fiber bundles and they may work in retro-reflection mode, transillumination mode, or any relative location of transmitters and receivers as described with respect to FIG. 2. The number of transmission fibers may be different from the number of receiver fibers. The receiver processing unit can have a mechanical switch to address the separate detection required of each individual receiver fiber or multiple receivers may be used or the fibers may be wavelength or time division multiplexed. Multiple fibers can have any orientation with respect to one another around the tissue of interest so as to optimize the detection of salient features necessary for diagnosis of disease state, structural integrity, or other parameters. The interface between the OCT system and implanted probes may be present within the body (for instance a small distance below the surface of the skin such that transcutaneous illumination is possible) or outside the body (for instance a small fiber optic connector is secured to the external surface of the body). There is a wide range of medical applications and methods that this embodiment of the invention will enable. These include:

Toxin:

The implanted device can be used to monitor the effect of radiation, chemicalibiological toxin, or other therapeutic procedures as illustrated in FIG. 24. Fibers oriented around and/or within the tissue of interest can be used to detect structural and/or metabolic changes indicative of response or toxicity of the agent of interest. This diagnostic information can be used in real-time to coordinate the therapeutic procedure or in non-real time where the effects of the therapeutic agent are gathered over a long period of time and continuously or periodically assessed to guide further treatment.

Nerve:

The implanted device may be used to assess neural activity. Fiber(s) may be placed in direct contact or in close proximity of either peripheral or central myelinated or unmyelinated nerves. Neural activity may be monitored by either changes in nerve size, spectral properties (absorption, polarization, etc.), or response to exogenous probe.

Solute:

In one embodiment, chemical concentrations (such as solute, gas, or metabolite concentrations) may be measured in organ parenchyma (such as the myocardium), lumen (such as the urinary tract or blood), support structures (such as fascia), or free space (such as in lungs or other cavities) via the direct placement of single or multiple fibers.

Vascular:

The implanted device may be used to assess regional or whole body vascular function. Probes, for example, may be placed in both external cerebral and lower extremity vessels (combine with or without Doppler imaging ability) to assess changes in relative blood flow during postural changes or high G maneuvers associated with air flight.

Blood Cell:

The implantable device may be implanted within and/or in the general vicinity of the bone marrow for the purpose of monitoring the production of both normal and abnormal blood cells.

Phenotypic Expression:

The implanted device may be placed in the organ of interest for the assessment, with or without the addition of other biological probes, of phenotypic changes such as cell size, cell number, muscle strain/contraction, nuclear concentration, or cell surface maker concentration.

Regional Lung Function:

In one embodiment, the device will be placed within or in the vicinity of the lung for the purpose of assessing regional lung function such as changes in alveolar size or local gas concentrations.

Transillumination

Forward directed imaging can be performed with the source fiber or fibers proximal to the tissue of interest and the receiving fiber/detector distal to the tissue of interest. This is a special case of the concepts previously described with respect to FIG. 2. The procedure would be of particular use for assessing or surgically manipulating vessels, nerves, and lymph nodes. The illumination beam and/or receiver aperture can be scanned with any of the previously described methods. The receiving element can consist of a single fiber or detector (aperture scanned or not) or a fiber or detector array could be used and demodulated as described above. A single housing (open on three sides) could allow the probe/device to be placed in the tissue of interest while allowing rigid metering between source and detector planes.

Transurethral Prostatectomy

Forward, axial, or cross-sectional directed imaging can be performed during transurethral prostatectomy procedures such as: transurethral resection of the prostate (TURP), suprapubic prostatectomy, transurethral incision of the prostate (TUIP), transurethral laser incision of the prostate (TULIP), visual laser ablation (VLAP), and open prostate surgery. Guiding the prostatectomy procedure with OCT and other optical imaging modalities and devices of this invention can dramatically improve patient outcome. In prostatectomy procedures that involve cutting with a surgical blade, one or more fibers can be placed within, adjacent, or on the struts of the retractable blades (similar to that discussed with respect to FIG. 12). Fibers will extend to sites from the distal to proximal end of the blade. A flush port may be included on the guide catheter surface adjacent to the blade for the purpose of flushing blood and/or tissue debris. In prostatectomy procedures that involve laser incision or laser ablation the high power laser light can be coupled into the OCT fiber (via time or wavelength division multiplexing techniques as described previously) or to an adjacent fiber as described with respect to FIG. 13.

Open Field Surgical Tools

Forward directed backscattering or transillumination imaging can be used with instruments used in the surgical field including scissors, forceps, hemostats, and snares. Uses will include preventing iatrogenic injury, assessing/guiding nerve and vascular repair, and open field tissue diagnostics. The probes could be used for one-dimensional ranging and thus do not require scanning or could be of any of the scanning embodiments described previously.

FIG. 25 shows some examples. FIG. 25a shows a simple hand held surgical probe 340 that could be used in a wide variety of general purpose medical procedures and fields. A fiber 57 runs down the center of the surgical probe 340 and contains the imaging and scanning optics 346 as a simple lens such as GRIN lens 62 (or no lens) at the distal end 344. FIG. 25b shows an example of medical scissors or hemostat device 348. In this example the optical imaging and scanning module 346 is mounted near the hinge 352 and aligned so as to illuminate the region near where the tip of the two blades 356 meet upon closing. FIG. 25c shows a similar example of forceps 358 with the optical imaging and scanning module 346 mounted so as to illuminate the region between the tips of the two forcep prongs 360. FIG. 25d shows an example where the optical imaging and scanning module 346 is used to illuminate the region near the end of a snare 364. The integration with the OCT or other optical imaging engine can include single or multiple fibers and utilize the wide variety of scanning techniques described earlier or can use simple 1D (longitudinally only) scanning to minimize the cost and complexity of the probe module.

Endoscopic/Laparoscopic Surgical Tools

Figure 26A:
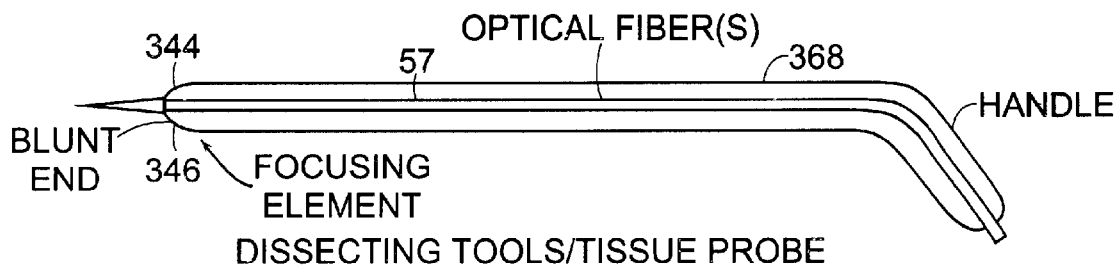
FIGS. 26a–c is a longitudinal sectional view of an embodiment of laparoscopic and endoscopic surgical tools/probes.
Figure 26B:
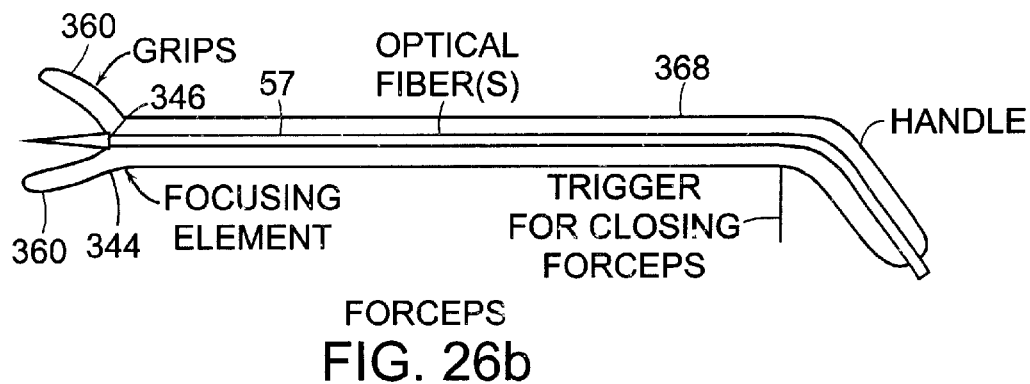
Figure 26C:
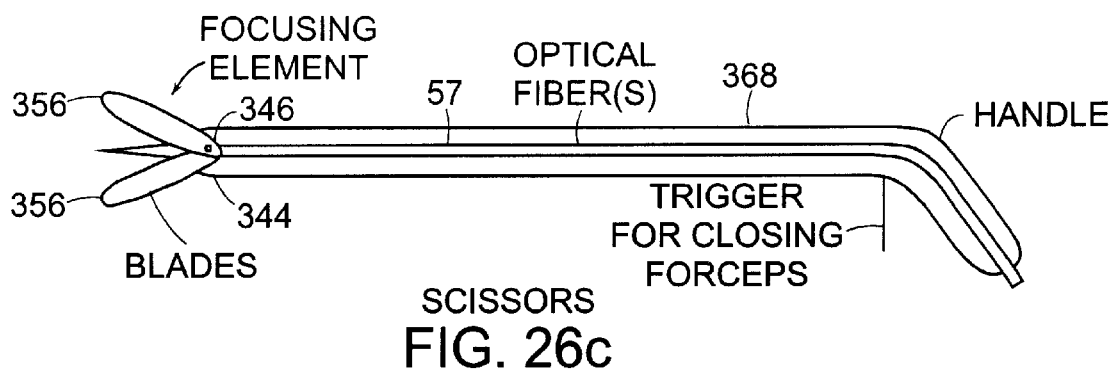

Forward-directed backscattering or transillumination imaging also can be used with instruments used in laparoscopy/endoscopy including scissors, forceps, snares, or dissecting probes similar to those described with respect to FIG. 25 and shown in FIG. 26. Devices used in laparoscopic and endoscopic procedures have a much longer rigid shaft 368 to allow the medical specialist to perform the required procedures through small incisions which are distant from the location of interest. Due to the minimally invasive nature of these devices it is preferable that the imaging and scanning optics be located within the long smooth body of the tool as opposed to outside the body of the device as in FIG. 25. The devices can have a simple single fiber 57 for performing longitudinal ranging and 1-D imaging, can contain a fiber bundle (not shown) for multi-dimensional imaging, or contain a small scanning mechanism at the distal end 344 for multi-dimensional imaging as described previously. Uses will include preventing iatrogenic injury, assessing/guiding nerve and vascular repair, and tissue diagnostics. The integration with the OCT system can include single or multiple fibers.

Biopsy Punch Tissue Extraction

Figure 27:
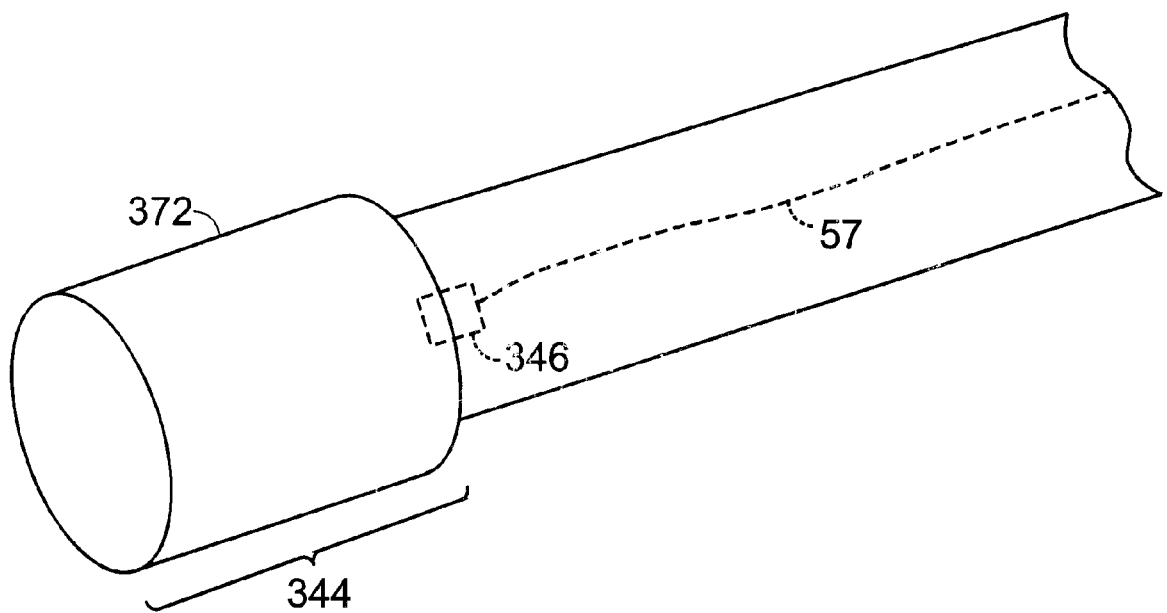
FIG. 27 is a longitudinal sectional view of an embodiment of a surgical biopsy punch tool.

Punch biopsies of tissue can be guided with the use of forward, lateral, or cross-sectional OCT and other optical imaging techniques as described in this invention. As shown in FIG. 27 punch biopsy tools typically consist of small (1–5 mm diameter) cylindrical blades 372 at the distal end 344 that cut a core of tissue that is retained in the bore of the cylindrical blade 372. Optical fibers and beam focusing optics can be located within the cylindrical blade or, in the case of excisional grippers (pinchers) (not shown), can be located at the pivot-point of the instrument similar to what is shown for scissors in FIG. 25b. Obtaining punch biopsies at remote sites within the body is extremely difficult if not guided by some imaging technology. The use of forward-directed OCT or other optical imaging techniques will permit sub-surface imaging and identification of tissue and tissue morphology prior to extraction and reduce the high error rates and morbidity associated with random or unguided sampling.

Rotational Tissue Extraction or Disruption

Tissue extraction or disruption (performed with rotating spurs, blades, or similar devices, compression, heat, shockwave, RF, toxin, or laser illumination) can be guided with forward, lateral, or cross-sectional OCT or other optical imaging techniques, devices, and methods of this invention. Single fibers or fiber bundles may be used to perform ranging or imaging as required. Tissue extraction or disruption may be performed in an antegrade or retrograde direction. In addition, extraction or disruption can be performed in a cross-sectional direction or parallel to the axis of the catheter/endoscope. Tissue extraction or disruption may be guided with feedback from the OCT system, thereby changing, for example, regional blade speed or pressure or in the event that several spinning or cutting mechanisms are used simultaneously (for instance along the shaft); the devices can be individually controlled by separate OCT imaging engines.

Uterine Cervical Imaging

Forward or lateral tissue imaging, in addition to imaging along the axis of the catheter, can be used for uterine cervical diagnostics or guiding surgical interventions of the cervix (FIG. 28). Several embodiments and scanning patterns are possible such as imaging in a circular/oval pattern radiating from the lumen of the cervix or imaging in a linear manner extending from the orifice of the cervix to the vaginal interface of the cervix. FIG. 25a in side and end view provides an example where imaging is accomplished using a fiber bundle 288 that is arranged in a series of one or more symmetric rings of fibers at the distal end as shown. Each fiber can be coupled (not shown) to a small lens, an integral fiber up-taper, or a single lens group. At the proximal end the fibers 57 can be scanned sequentially using a free space beam steering mirror and lenses, coupled to a fast 1:N fiber optic switch matrix, or coupled to separate imaging engines (not shown). Shown in FIG. 28*b* is a radial/circular scanning embodiment similar to that previously described with respect to FIG. 18*c*. The output of fiber 57 is collinated using lens 152 and reflected off mirror 154 and adjustable fold mirror 158. The radial distance or angle of fold mirror 158 can be adjusted to accommodate different scan radii. Shown in FIG. 28*c* is a linear scanning embodiment that may use any of the methods previously described.

What is claimed is:

1. An optical imaging system comprising:
   a light source;
   a sample illuminator in communication with said light source and positioned to illuminate a sample;
   a probe having a housing, said housing having a longitudinal axis, a first end and a second end, said sample illuminator at least partially located within said housing;
   a scanning mechanism at least partially positioned in said probe housing, said scanning mechanism causing a beam of light emitted from said sample illuminator to scan said sample;
   a reference arm adjustable to select a predetermined depth within said sample;
   a beam splitter positioned to direct light from said light source to both said sample illuminator and said reference arm;
   a sample light collector disposed apart from said illuminator and positioned to collect reflected light altered by said sample from said predetermined depth within said sample;
   a detector generating a signal in response to incident light;
   a beam combiner positioned to direct light from said sample light collector and said reference arm to said detector, said detector generating a signal in response to said combined light; and
   a processor in electrical communication with said detector, said processor producing an image in response to said signal from said detector.

2. An optical imaging system comprising:
   a light source;
   a sample illuminator in communication with said light source and positioned to illuminate a sample;
   a probe having a housing, said housing having a longitudinal axis, a first ends a second end, and an outer surface, said sample illuminator at least partially located within said housing;
   a scanning mechanism at least partially positioned in said probe housing and comprising a scanning device selected from the group consisting of a rotating elliptical knob, a wire controlled pivot, a pneumatic device, a rigid tube under tension or an electrostatic device, wherein said device is in communication with an optical element, said optical element selected from a group consisting of a lens, a fiber, said lens and fiber, and a beam deflection element such that actuation of the device causes a beam of light emitted from said sample illuminator to scan said sample;
   a reference arm adjustable to select a predetermined depth within said sample;
   a beam splitter positioned to direct light from said light source to both said sample illuminator and said reference arm;
   a sample light collector disposed apart from said sample illuminator and positioned to collect reflected light altered by said sample from said predetermined depth within said sample;
   a detector generating a signal in response to incident light;
   a beam combiner positioned to direct light from said sample light collector and said reference arm to said detector, said detector generating a signal in response to said combined light; and
   a processor in electrical communication with said detector, said processor producing an image in response to said signal from said detector.

3. The optical system of claim 2 wherein said scanning mechanism comprises:
   a position sensitive roller located adjacent to said outer surface of said housing and permitting said housing to move at a substantially fixed distance along a surface in communication with said position sensitive roller.

4. An optical imaging system comprising:
   a light source;
   a sample illuminator in communication with said light source and positioned to illuminate a sample;
   a probe having a housing, said housing having a longitudinal axis, a first end and a second end, said sample illuminator at least partially located within said housing;
   a scanning mechanism at least partially positioned in said probe housing and comprising at least one lens and an electro-optic beam deflector, said scanning mechanism causing a beam of light emitted from said sample illuminator to scan said sample;
   a reference arm adjustable to select a predetermined depth within said sample;
   a beam splitter positioned to direct light from said light source to both said sample illuminator and said reference arm;
   a sample light collector disposed apart from said sample illuminator and positioned to collect reflected light altered by said sample from said-predetermined depth within said sample;
   a detector generating a signal in response to incident light;
   a beam combiner positioned to direct light from said sample light collector and said reference arm to said detector, said detector generating a signal in response to said combined light; and
   a processor in electrical communication with said detector, said processor producing an image in response to said signal from said detector.

5. An optical imaging system comprising:
   a light source;
   a sample illuminator in communication with said light source and positioned to illuminate a sample;
   a probe having a housing, said housing having a longitudinal axis, a first end and a second end, said sample illuminator at least partially located within said housing;
   a scanning mechanism at least partially positioned in said probe housing and comprising a mirror movable in at least one axis, said scanning mechanism causing a beam of light emitted from said sample illuminator to scan said sample;
   a reference arm adjustable to select a predetermined depth within said sample;
   a beam splitter positioned to direct light from said light source to both said sample illuminator and said reference arm;

a sample light collector disposed apart from said sample illuminator and positioned to collect reflected light altered by said sample from said-predetermined depth within said sample;

a detector generating a signal in response to incident light;

a beam combiner positioned to direct light from said sample light collector and said reference arm to said detector, said detector generating a signal in response to said combined light; and a processor in electrical communication with said detector, said processor producing an image in response to said signal from said detector.

6. An optical imaging system comprising:

a light source;

a sample illuminator in communication with said light source and positioned to illuminate a sample;

a probe having a housing, said housing having a longitudinal axis, a first end and a second end, said sample illuminator at least partially located within said housing and being attached to a surgical instrument having an operating tip;

a scanning mechanism at least partially positioned in said probe housing and comprising a scanning device selected from the group consisting of a rotating elliptical knob, a piezoelectric transducer, a wire-controlled pivot, a pneumatic device, a rigid tube under tension or an electrostatic device, wherein said device is in communication with an optical element, said optical element selected from a group consisting of a lens, a fiber, said lens and fiber, and a beam deflection element such that actuation of the device causes a beam of light emitted from said sample illuminator to scan said sample;

a reference arm adjustable to select a predetermined depth within said sample;

a beam splitter positioned to direct light from said light source to both said sample illuminator and said reference arm;

a sample light collector disposed apart from said sample illuminator and positioned to collect reflected light altered by said sample from said predetermined depth within said sample;

a detector generating a signal in response to incident light;

a beam combiner positioned to direct light from said sample light collector and said reference arm to said detector, said detector generating a signal in response to said combined light; and a processor in electrical communication with said detector, said processor producing an image of the region of said operating tip scanned by light emitted from said probe in response to said signal from said detector.

7. An optical imaging system comprising:

a light source;

a sample illuminator in communication with said light source and positioned to illuminate a sample;

a probe having a housing, said housing having a longitudinal axis, a first end and a second end, said sample illuminator at least partially located within said housing;

a scanning mechanism at least partially positioned in said probe housing and comprising a scanning device selected from the group consisting of a rotating elliptical knob, a piezoelectric transducer, a wire-controlled pivot, a pneumatic device, a rigid tube under tension or an electrostatic device, wherein said device is in communication with an optical element, said optical element selected from a group consisting of a lens, a fiber, said lens and fiber, and a beam deflection element such that actuation of the device causes a beam of light emitted from said sample illuminator to scan said sample;

a surgical laser fiber located within said probe housing, said surgical laser capable of incising, coagulating, or disrupting a portion of the sample;

a reference arm adjustable to select a predetermined depth within said sample;

a beam splitter positioned to direct light from said light source to both said sample illuminator and said reference arm;

a sample light collector disposed apart from said sample illuminator and positioned to collect reflected light altered by said sample from said predetermined depth within said sample;

a detector generating a signal in response to incident light;

a beam combiner positioned to direct light from said sample light collector and said reference arm to said detector, said detector generating a signal in response to said combined light; and a processor in electrical communication with said detector, said processor producing an image of the region to be illuminated by said surgical laser in response to said signal from said detector.

8. An optical imaging system comprising:

a light source;

a sample illuminator in communication with said light source and positioned to illuminate a sample, said sample illuminator comprising:
  a housing defining a bore;
  an illumination optical fiber having a first end and a second end, said first end located within said bore and said second end in optical communication with said light source;
  an optical train having a first and second end and located within said bore;
  a beam splitter positioned adjacent said second end of said optical train;
  one or more viewing optical components positioned to receive light passing through said beam splitter from said optical train; and
  scanning optics positioned to receive light reflected by said beam splitter from said optical train;

a probe having a housing comprising a laparoscope defining a bore, said sample illuminator at least partially located within said housing;

a scanning mechanism at least partially positioned in said probe housing, said scanning mechanism causing a beam of light emitted from said sample illuminator to scan said sample;

a reference arm;

a sample light collector positioned to collect light altered by said sample;

a detector generating a signal in response to incident light;

a beam combiner positioned to direct light from said sample light collector and said reference arm to said detector, said detector generating a signal in response to said combined light; and a processor in electrical communication with said detector, said processor producing an image in response to said signal from said detector.

9. The optical imaging system of claim 8, further comprising a surgical laser source in optical communication with said optical train, wherein said processor produces an image of the region to be illuminated by said surgical laser.

* * * * *